US007960141B2

(12) United States Patent
Ryu et al.

(10) Patent No.: US 7,960,141 B2
(45) Date of Patent: Jun. 14, 2011

(54) SYSTEMS FOR THE EXPRESSION OF ORTHOGONAL TRANSLATION COMPONENTS IN EUBACTERIAL HOST CELLS

(75) Inventors: Youngha Ryu, San Diego, CA (US); Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 1128 days.

(21) Appl. No.: 11/715,672

(22) Filed: Mar. 7, 2007

(65) Prior Publication Data
US 2007/0281335 A1    Dec. 6, 2007

Related U.S. Application Data

(60) Provisional application No. 60/780,973, filed on Mar. 9, 2006, provisional application No. 60/783,497, filed on Mar. 17, 2006, provisional application No. 60/855,336, filed on Oct. 29, 2006.

(51) Int. Cl.
*C12N 15/70* (2006.01)
*C12N 1/00* (2006.01)
*C07H 21/00* (2006.01)

(52) U.S. Cl. .................... 435/69.1; 435/243; 435/252.1; 435/252.8

(58) Field of Classification Search ........................ None
See application file for complete search history.

(56) References Cited

U.S. PATENT DOCUMENTS

| | | | |
|---|---|---|---|
| 5,024,939 A | 6/1991 | Gorman | |
| 6,927,042 B2 | 8/2005 | Schultz et al. | |
| 7,045,337 B2 | 5/2006 | Schultz et al. | |
| 7,083,970 B2 | 8/2006 | Schultz et al. | |
| 7,129,333 B2 | 10/2006 | Schultz et al. | |
| 7,183,082 B2 | 2/2007 | Schultz et al. | |
| 7,199,222 B2 | 4/2007 | Shultz et al. | |
| 7,217,809 B2 | 5/2007 | Schultz et al. | |
| 7,238,510 B2 | 7/2007 | Schultz et al. | |
| 7,262,040 B2 | 8/2007 | Schultz et al. | |
| 7,399,619 B2 * | 7/2008 | Xie et al. | 435/193 |
| 7,432,092 B2 * | 10/2008 | Schultz et al. | 435/183 |
| 2004/0198637 A1 | 10/2004 | Schultz et al. | |
| 2004/0265952 A1 | 12/2004 | Deiters et al. | |
| 2005/0009049 A1 | 1/2005 | Chin et al. | |
| 2005/0136513 A1 | 6/2005 | Zhang et al. | |
| 2005/0208536 A1 | 9/2005 | Schultz et al. | |
| 2005/0227318 A1 | 10/2005 | Alfonta et al. | |
| 2005/0272121 A1 | 12/2005 | Xie et al. | |
| 2006/0063244 A1 | 3/2006 | Schultz et al. | |
| 2006/0068478 A1 | 3/2006 | Schultz et al. | |
| 2006/0073507 A1 | 4/2006 | Deiters et al. | |
| 2006/0110784 A1 | 5/2006 | Deiters et al. | |
| 2006/0110796 A1 | 5/2006 | Schultz et al. | |
| 2006/0134746 A1 | 6/2006 | Deiters et al. | |
| 2006/0160175 A1 | 7/2006 | Anderson et al. | |
| 2006/0177900 A1 | 8/2006 | Anderson et al. | |
| 2006/0234367 A1 | 10/2006 | Schultz et al. | |
| 2006/0246509 A1 | 11/2006 | Deiters et al. | |
| 2007/0009990 A1 | 1/2007 | Alfonta et al. | |
| 2007/0020634 A1 | 1/2007 | Anderson et al. | |
| 2007/0042461 A1 | 2/2007 | Anderson et al. | |
| 2007/0111193 A1 | 5/2007 | Zhang et al. | |
| 2007/0154952 A1 | 7/2007 | Chin et al. | |
| 2007/0166791 A1 | 7/2007 | Chin et al. | |
| 2007/0172915 A1 | 7/2007 | Schultz et al. | |
| 2007/0178448 A1 | 8/2007 | Tsao et al. | |
| 2007/0184517 A1 | 8/2007 | Schultz et al. | |
| 2007/0238152 A1 | 10/2007 | Wang et al. | |

FOREIGN PATENT DOCUMENTS

| | | |
|---|---|---|
| WO | WO 2006/110182 | 12/2006 |
| WO | WO 2007/103490 | 9/2007 |

OTHER PUBLICATIONS

Sakamoto et al (Site-specific incorporation of an unnatural amino acid into proteins in mammalian cells, Nucleic Acids Research, 2002, vol. 30, No. 21 4692-4699.*
Wang et al. (Expanding the Genetic Code of *Escherichia coli* .Science Apr. 20, 2001: vol. 292. No. 5516, pp. 498-500).*
Komine et al. (1990) "Genomic Organization and Physical Mapping of the Transfer RNA Genes in *Escherichia coli* K12." *Journal of Molecular Biology*, 212: 579-598.
Kuchino et al. (1985) "Structure and transcription of the $tRNA_1^{Pro}$ gene from *Escherichia coli*." *Nucleic Acids Research*, 13(9): 3213-3220.
Muskhelishvili et al. (1997) "FIS activates sequential steps during transcription initiation at a stable RNA promoter." *The EMBO Journal*, 16(12): 3655-3665.
Ryu and Schultz (2006) "Efficient incorporation of unnatural amino acids into proteins in *Escherichia coli*." *Nature Methods*, 3(4): 263-265.
Hsu et al. (1984) "Structure of an *Escherichia coli* tRNA operon containing linked genes for arginine histidine, leucine, and proline tRNAs." *Journal of Bacteriology*, 158:934-942.
Alfonta et al. (2003) "Site-Specific Incorporation of a Redox-Active Amino Acid into Proteins." *Journal of the American Chemistry Society*, 125: 14662-14663.
Chin et al. (2002) "Addition of a photocrosslinking amino acid to the genetic code of *Escherichia coli*." *Proceedings of the National Academy of Sciences*, USA, 99(17): 11020-11024.
Wang and Schultz (2005) "Expanding the Genetic Code," *Angewandte Chemie Int. Ed.*, 44(1): 34-66.
Wang and Schultz (2001) "A general approach for the generation of orthogonal tRNAs." *Chemistry & Biology*, 8: 883-890.
Wang et al. (2006) "Expanding the Genetic Code," *Annual Review of Biophysics & Biomolecular Structure*, 35: 225-249.
Wang et al. (2003) "Addition of the keto functional group to the genetic code of *Escherichia coli*." *Proceedings of the National Academy of Sciences*, USA, 100(1): 56-61.

(Continued)

*Primary Examiner* — Manjunath N Rao
*Assistant Examiner* — Kagnew H Gebreyesus
(74) *Attorney, Agent, or Firm* — Quine Intellectual Property Law Group, P.C.; Stacy Landry; Brian E. Davy

(57) ABSTRACT

The invention relates to compositions and methods for the in vivo production of polypeptides comprising one or more unnatural amino acids. Specifically, the invention provides plasmid systems for the efficient eubacterial expression of polypeptides comprising one or more unnatural amino acids at genetically-programmed positions.

20 Claims, 13 Drawing Sheets

OTHER PUBLICATIONS

Wu et al. (2004) "A Genetically Encoded Photocaged Amino Acid." *Journal of the American Chemistry Society*, 126: 14306-14307.
Xie and Schultz (2005) "Adding Amino Acids to the Genetic Repertoire." *Current Opinion in Chemical Biology*, 9(6): 548-554.
Xie and Schultz (2005) "An Expanding Genetic Code," *Methods*, 36(3): 227-238.
Zhang et al. (2004) "A New Strategy for the Synthesis of Glycoproteins." *Science*, 303: 371-373.

* cited by examiner

Nucleotide and Amino Acid Sequences

| SEQ ID NO: | Description | SEQUENCE |
|---|---|---|
| 1 | Methanococcus jannaschii - suppressor tyrosyl-tRNA$_{CUA}$ aka MjtRNA-Tyr(CUA) or mutRNA$^{Tyr}_{CUA}$ | CCGGCGGUAGUUCAGCAGGGCAGAACGGCGGACUCUAAAUCCG CAUGGCGCUGGUUCAAAUCCGGCCCGCCGGACCA |
| 2 | Wild-type Methanococcus jannaschii tyrosyl-tRNA synthetase (MjTyrRS) amino acid sequence | MDEFEMIKRNTSEIISEEELREVLKKDEKSAYIGFEPSGKIHL GHYLQIKKMIDLQNAGFDIIILLADLHAYLNQKGELDEIRKIG DYNKKVFEAMGLKAKYVYGSEFQLDKDYTLNVYRLALKTTLKR ARRSMELIAREDENPKVAEVIYPIMQVNDIHYLGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |
| 3 | Wild-type Methanococcus jannaschii tyrosyl-tRNA synthetase (MjTyrRS) nucleotide sequence | ATGGACGAATTTGAAATGATAAAGAGAAACACATCTGAAATTATCAGC GAGGAAGAGTTAAGAGAGGTTTTAAAAAAAGATGAAAAATCTGCTTAC ATAGGTTTTGAACCAAGTGGTAAAATACATTTAGGGCATTATCTCCAA ATAAAAAAGATGATTGATTTACAAAATGCTGGATTTGATATAATTATA TTGTTGGCTGATTTACACGCCTATTTAAACCAGAAAGGAGAGTTGGAT GAGATTAGAAAAATAGGAGATTATAACAAAAAAGTTTTTGAAGCAATG GGGTTAAAGGCAAAATATGTTTATGGAAGTGAATTCCAGCTTGATAAG GATTATACACTGAATGTCTATAGATTGGCTTTAAAAACTACCTTAAAA AGAGCAAGAAGGAGTATGGAACTTATAGCAAGAGAGGATGAAAATCCA AAGGTTGCTGAAGTTATCTATCCAATAATGCAGGTTAATGATATTCAT TATTTAGGCGTTGATGTTGCAGTTGGAGGGATGGAGCAGAGAAAAATA CACATGTTAGCAAGGGAGCTTTTACCAAAAAAGGTTGTTTGTATTCAC AACCCTGTCTTAACGGGTTTGGATGGAGAAGGAAAGATGAGTTCTTCA AAAGGGAATTTTATAGCTGTTGATGACTCTCCAGAAGAGATTAGGGCT AAGATAAAGAAAGCATACTGCCCAGCTGGAGTTGTTGAAGGAAATCCA ATAATGGAGATAGCTAAATACTTCCTTGAATATCCTTTAACCATAAAA AGGCCAGAAAAATTTGGTGGAGATTTGACAGTTAATAGCTATGAGGAG TTAGAGAGTTTATTTAAAAATAAGGAATTGCATCCAATGGATTTAAAA AATGCTGTAGCTGAAGAACTTATAAAGATTTTAGAGCCAATTAGAAAG AGATTA |
| 4 | p-benzoyl-L-phenylalanine aminoacyl-tRNA synthetase (BpaRS) amino acid sequence (derived from wild-type Methanococcus jannaschii tyrosyl tRNA-synthetase) | MDEFEMIKRNTSEIISEEELREVLKKDEKSAGIGFEPSGKIHL GHYLQIKKMIDLQNAGFDIIILLADLHAYLNQKGELDEIRKIG DYNKKVFEAMGLKAKYLYGSPFQLDKDYTLNVYRLALKTTLKR ARRSMELIAREDENPKVAEVIYPIMQVNTSHYLGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMRLKNAVAEELIKILEP IRKRL |

Fig. 8

| SEQ ID NO: | Description | SEQUENCE |
|---|---|---|
| 5 | p-benzoyl-L-phenylalanine aminoacyl-tRNA synthetase nucleotide sequence | ATGGACGAATTTGAAATGATAAAGAGAAACACATCTGAAATTA TCAGCGAGGAAGAGTTAAGAGAGGTTTTAAAAAAAGATGAAAA ATCTGCTGGTATAGGTTTTGAACCAAGTGGTAAAATACATTTA GGGCATTATCTCCAAATAAAAAAGATGATTGATTTACAAAATG CTGGATTTGATATAATTATATTGTTGGCTGATTTACACGCCTA TTTAAACCAGAAGGAGAGTTGGATGAGATTAGAAAAATAGGA GATTATAACAAAAAAGTTTTTGAAGCAATGGGGTTAAAGGCAA AATATCTTTATGGAAGTCCTTTCCAGCTTGATAAGGATTATAC ACTGAATGTCTATAGATTGGCTTTAAAAACTACCTTAAAAAGA GCAAGAAGGAGTATGGAACTTATAGCAAGAGAGGATGAAAATC CAAAGGTTGCTGAAGTTATCTATCCAATAATGCAGGTTAATAC GAGTCATTATTTAGGCGTTGATGTTGCAGTTGGAGGGATGGAG CAGAGAAAAATACACATGTTAGCAAGGGAGCTTTTACCAAAAA AGGTTGTTTGTATTCACAACCCTGTCTTAACGGGTTTGGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGAGAGTTTATTTAAAAATAAGGAATTGCATCCAATGGATTT AAAAAATGCTGTAGCTGAAGAACTTATAAAGATTTTAGAGCCA ATTAGAAAGAGATTA |
| 6 | p-acetyl-L-phenylalanine aminoacyl-tRNA synthetase (pAcPheRS) amino acid sequence (derived from wild-type Methanococcus jannaschii tyrosyl tRNA-synthetase) | MDEFEMIKRNTSEIISEEELREVLKKDEKSALIGFEPSGKIHL GHYLQIKKMIDLQNAGFDIIILLADLHAYLNQKGELDEIRKIG DYNKKVFEAMGLKAKYVYGSEFQLDKDYTLNVYRLALKTTLKR ARRSMELIAREDENPKVAEVIYPIMQVNGCHYRGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |
| 7 | p-acetyl-L-phenylalanine aminoacyl-tRNA synthetase nucleotide sequence | ATGGACGAATTTGAAATGATAAAGAGAAACACATCTGAAATTA TCAGCGAGGAAGAGTTAAGAGAGGTTTTAAAAAAAGATGAAAA ATCTGCTCTGATAGGTTTTGAACCAAGTGGTAAAATACATTTA GGGCATTATCTCCAAATAAAAAAGATGATTGATTTACAAAATG CTGGATTTGATATAATTATATTGTTGGCTGATTTACACGCCTA TTTAAACCAGAAGGAGAGTTGGATGAGATTAGAAAAATAGGA GATTATAACAAAAAAGTTTTTGAAGCAATGGGGTTAAAGGCAA AATATGTTTATGGAAGTGAATTCCAGCTTGATAAGGATTATAC ACTGAATGTCTATAGATTGGCTTTAAAAACTACCTTAAAAAGA GCAAGAAGGAGTATGGAACTTATAGCAAGAGAGGATGAAAATC CAAAGGTTGCTGAAGTTATCTATCCAATAATGCAGGTTAATGG TTGTCATTATAGGGGCGTTGATGTTGCTGTTGGAGGGATGGAG CAGAGAAAAATACACATGTTAGCAAGGGAGCTTTTACCAAAAA AGGTTGTTTGTATTCACAACCCTGTCTTAACGGGTTTGGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGAGAGTTTATTTAAAAATAAGGAATTGCATCCAATGGATTT AAAAAATGCTGTAGCTGAAGAACTTATAAAGATTTTAGAGCCA ATTAGAAAGAGATTA |

Fig. 8 cont.

| SEQ ID NO: | Description | SEQUENCE |
|---|---|---|
| 8 | p-azido-L-phenylalanine aminoacyl-tRNA synthetase (pAzPheRS) amino acid sequence (derived from wild-type *Methanococcus jannaschii* tyrosyl tRNA-synthetase) | MDEFEMIKRNTSEIISEEELREVLKKDEKSALIGFEPSGKIHL GHYLQIKKMIDLQNAGFDIIILLADLHAYLNQKGELDEIRKIG DYNKKVFEAMGLKAKYVYGSPFQLDKDYTLNVYRLALKTTLKR ARRSMELIAREDENPKVAEVIYPIMQVNQIHSSGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |
| 9 | p-azido-L-phenylalanine aminoacyl-tRNA synthetase nucleotide sequence | ATGGACGAATTTGAAATGATAAAGAGAAACACATCTGAAATTA TCAGCGAGGAAGAGTTAAGAGAGGTTTTAAAAAAAGATGAAAA ATCTGCTCTGATAGGTTTTGAACCAAGTGGTAAAATACATTTA GGGCATTATCTCCAAATAAAAAAGATGATTGATTTACAAAATG CTGGATTTGATATAATTATATTGTTGGCTGATTTACACGCCTA TTTAAACCAGAAAGGAGAGTTGGATGAGATTAGAAAAATAGGA GATTATAACAAAAAGTTTTTGAAGCAATGGGGTTAAAGGCAA AATATGTTTATGGAAGTCCGTTCCAGCTTGATAAGGATTATAC ACTGAATGTCTATAGATTGGCTTTAAAAACTACCTTAAAAAGA GCAAGAAGGAGTATGGAACTTATAGCAAGAGAGGATGAAAATC CAAAGGTTGCTGAAGTTATCTATCCAATAATGCAGGTTAATCA GATTCATTCTAGTGGCGTTGATGTTGCAGTTGGAGGGATGGAG CAGAGAAAAATACACATGTTAGCAAGGGAGCTTTTACCAAAAA AGGTTGTTTGTATTCACAACCCTGTCTTAACGGGTTTGGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGAGAGTTTATTTAAAAATAAGGAATTGCATCCAATGGATTT AAAAAATGCTGTAGCTGAAGAACTTATAAAGATTTTAGAGCCA ATTAGAAAGAGATTA |
| 10 | p-iodo-L-phenylalanine aminoacyl-tRNA synthetase (pIPheRS) amino acid sequence (derived from wild-type *Methanococcus jannaschii* tyrosyl tRNA-synthetase) | MDEFEMIKRNTSEIISEEELREVLKKDEKSALIGFEPSGKIHL GHYLQIKKMIDLQNAGFDIIILLADLHAYLNQKGELDEIRKIG DYNKKVFEAMGLKAKYVYGSSFQLDKDYTLNVYRLALKTTLKR ARRSMELIAREDENPKVAEVIYPIMQVNPLHYEGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |

Fig. 8 cont.

| SEQ ID NO: | Description | SEQUENCE |
|---|---|---|
| 11 | p-iodo-L-phenylalanine aminoacyl-tRNA synthetase nucleotide sequence | ATGGACGAATTTGAAATGATAAAGAGAAACACATCTGAAATTA TCAGCGAGGAAGAGTTAAGAGAGGTTTTAAAAAAAGATGAAAA ATCTGCTCTGATAGGTTTTGAACCAAGTGGTAAAATACATTTA GGGCATTATCTCCAAATAAAAAAGATGATTGATTTACAAAATG CTGGATTTGATATAATTATATTGTTGGCTGATTTACACGCCTA TTTAAACCAGAAAGGAGAGTTGGATGAGATTAGAAAAATAGGA GATTATAACAAAAAAGTTTTTGAAGCAATGGGGTTAAAGGCAA AATATGTTTATGGAAGTTCGTTCCAGCTTGATAAGGATTATAC ACTGAATGTCTATAGATTGGCTTTAAAAACTACCTTAAAAGA GCAAGAAGGAGTATGGAACTTATAGCAAGAGAGGATGAAAATC CAAAGGTTGCTGAAGTTATCTATCCAATAATGCAGGTTAATCC TCTTCATTATGAGGGCGTTGATGTTGCAGTTGGAGGGATGGAG CAGAGAAAAATACACATGTTAGCAAGGGAGCTTTTACCAAAAA AGGTTGTTTGTATTCACAACCCTGTCTTAACGGGTTTGGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGAGAGTTTATTTAAAAATAAGGAATTGCATCCAATGGATTT AAAAAATGCTGTAGCTGAAGAACTTATAAAGATTTTAGAGCCA ATTAGAAAGAGATTA |
| 12 | mutant *E. coli* glnS promoter, which has a TATC sequence in place of GATC at the -10 region (identified in Plumbridge and Söll, *Biochimie* 69:539-541 [1987]) | CGATTATCAATTTTAAAAAACTAACAGTTGTCAGCCTGTCCCG CTTATAATATCATACGCC |
| 13 | modified mutant *E. coli* glnS promoter TRN | CGATTATCAATTTTAAAAAACTAACAGTTGTCAGCCTGTCCCG CTTTAATATCATACGCC |
| 14 | tRNA linker sequence between the *E. coli* valU and valX genes | ACTACTTTATGTAGTCTCCGCCGTGTAGCAAGAAATTGAGAAG T |
| 15 | tRNA linker sequence between the *E. coli* ileT and alaT genes | AATTTGCACGGCAAATTTGAAGAGGTTTTAACTACATGTTAT |
| 16 | tRNA linker sequence between the *E. coli* serV and argV genes | TTT |
| 17 | tRNA linker sequence between the *E. coli* valV and valW genes | TCCT |
| 18 | tRNA linker sequence between the *E. coli* glyT and thrT genes | AGATGT |
| 19 | tRNA linker sequence between the *E. coli* metT and leuW genes | TCTTTTTTT |
| 20 | tRNA linker sequence between the *E. coli* glnW and metU | TCGAAGAAACAATCT |
| 21 | tRNA linker sequence between the *E. coli* hisR and leuT | TTATTAGAAGTTGTGACAAT |
| 22 | tRNA linker sequence between the *E. coli* glnU and glnW genes | TCTTCTTCGAGTAAGCGGTTCACCGCCCGGTTAT |
| 23 | tRNA linker sequence between the *E. coli* leuP and leuV genes | AACGAGGCGATATCAAAAAAAGTAAGATGACTGT |

Fig. 8 cont.

| SEQ ID NO: | Description | SEQUENCE |
|---|---|---|
| 24 | tRNA linker sequence between the E. coli glnV and glnX genes | ATTTATTCAAGACGCTTACCTTGTAAGTGCACCCAGT |
| 25 | tRNA linker sequence between the E. coli alaW and alaX genes | AATTTTGCACCCAGCAAACTTGGTACGTAAACGCATCGT |
| 26 | tRNA linker sequence between the E. coli ileU and alaU genes | AATTTGCACGGCAAATTTGAAGAGGTTTTAACTACATGTTAT |
| 27 | tRNA linker sequence between the E. coli ileV and alaV genes | AATTTGCACGGCAAATTTGAAGAGGTTTTAACTACATGTTAT |
| 28 | tRNA linker sequence between the E. coli metU and glnV genes | AATTCTGAATGTATCGAATATGTTCGGCAAATTCAAAACCAATTTGT |
| 29 | tRNA linker sequence between the E. coli glyW and cysT genes | GTTTAAAAGACATCGGCGTCAAGCGGATGTCTGGCTGAAAGGCCTGAAGAATTT |
| 30 | tRNA linker sequence between the E. coli argX and hisR genes | TTTAGTCCCGGCGCTTGAGCTGCGGTGGTAGTAATACCGCGTAACAAGATTTGTAGT |
| 31 | tRNA linker sequence between the E. coli argY and argZ genes | TCTCTTACTTGATATGGCTTTAGTAGCGGTATCAATATCAGCAGTAAAATAAATTTCCCGAT |
| 32 | E. coli proK promoter | AGGCATTTTGCTATTAAGGGATTGACGAGGGCGTATCTGCGCAGTAAGATGCGCCCCGCATT |
| 33 | E. coli proK terminator | AATTCGAAAAGCCTGCTCAACGAGCAGGCTTTTTT |
| 34 | E. coli proL promoter | ATCAGTTAGCGAAATATCTTACTTGCAATCGGTGTGGAAAACGGTAGTATTAGCAGCCACGAGT |
| 35 | E. coli proL terminator | AAAATCCCAAGAAAAAACCAACCCTTACGGTTGGTTTTTTT |
| 36 | E. coli proM terminator | ATTTTGAACCCCGCTTCGGCGGGGTTTTTT |
| 37 | primer proK P1 | GTGCACGGCTAACTAAGCGGCCTGCTGACTTTCTCGCCGATCAAAAGGC |
| 38 | primer proK T1 | CTTTCTCGCCGATCAAAAGGCATTTTGCTATTAAGGGATTGACGAGGGCGTATCTGCGCAGTAAGATGCGCCCCGCATTCCGGCGGTAGTTCAGCAGGGC |
| 39 | primer proK T2 | CTTTCTCGCCGATCAAAAGGCATTTTGCTATTAAGGGATTGACGAGGGCGTATCTGCGCAGTAAGATGCGCCCCGCATTCCGGCGGTAGTTCAGCAGGGC |
| 40 | primer proK P2 | GCATAAGCTTATGCAAAAAAGCCTGCTCGTTGAGCAGGCTTTTCG |
| 41 | primer proK-F | AGTCTGATCAGTGCACGGCTAACTAAGCGG |
| 42 | primer proK-R | GCATCTCGAGATGCAAAAAAGCCTGCTCGTTG |
| 43 | primer glnS P1 | CCGAGCTCCCGGGTCATC |
| 44 | primer glnS T1 | CCGAGCTCCCGGGTCATCAATCATCCCCATAATCCTTGTTAGATTATCAATTTTAAAAAACTAACAGTTGTCAGCCTGTC |
| 45 | primer glnS T2 | GTCCATATGGGATTCCTCAAAGCGTAAACAACGTATAACGGCGTATGATATTATAAGCGGGACAGGCTGACAACTGTTAG |
| 46 | primer glnS P2 | GTCCATATGGGATTCCTC |
| 47 | primer Linker P1 | GTGCACGGCTAACTAAGCGGCCTGCTGACTTTCTCGCCGATCAAAAGGC |
| 48 | primer Linker P2 | TACACGGCGGAGACTACATAAAGTAGTTGGTCCGGCGGGCCGGATTTG |
| 49 | primer Linker P3 | GTAGTCTCCGCCGTGTAGCAAGAAATTGAGAAGTCCGGCGGTAGTTCAGCAG |
| 50 | primer Linker P4 | AAACCTCTTCAAATTTGCCGTGCAAATTTGGTCCGGCGGGCCGGATTTG |

Fig. 8 cont.

| SEQ ID NO: | Description | SEQUENCE |
|---|---|---|
| 51 | primer Linker P5 | GCAAATTTGAAGAGGTTTTAACTACATGTTATCCGGCGGTAGTTCAGCAG |
| 52 | primer proK-R | GCATCTCGAGATGCAAAAAAGCCTGCTCGTTG |
| 53 | primer Tandem P1 | ATCAGTGCACGGCTAACTAAGCGG |
| 54 | primer Tandem P2 | GCTGGCATGCATGCAAAAAAGCCTGCTCGTTGAGC |
| 55 | primer Tandem P3 | ATCAGCATGCGGCTAACTAAGCGGCCTGCTG |
| 56 | primer Tandem P4 | GCTGCTCGAGATGCAAAAAAGCCTGC |
| 57 | leader sequence | MDPLVTAASVLEFGLFET |
| 58 | Northern Analysis Probe | CCCTGCTGAACTACCGCC- |

Fig. 8 cont.

SEQUENCE LISTING

<160> NUMBER OF SEQ ID NOS: 58

<210> SEQ ID NO 1
<211> LENGTH: 77
<212> TYPE: RNA
<213> ORGANISM: Artificial
<220> FEATURE:
<223> OTHER INFORMATION: suppressor tyrosyl-tRNA CUA derived from
      Methanococcus jannaschii

<400> SEQUENCE: 1
ccggcgguag uucagcaggg cagaacggcg gacucuaaau ccgcauggcg cugguucaaa     60
uccggcccgc cggacca                                                   77

<210> SEQ ID NO 2
<211> LENGTH: 306
<212> TYPE: PRT
<213> ORGANISM: Methanococcus jannaschii

<400> SEQUENCE: 2

Met Asp Glu Phe Glu Met Ile Lys Arg Asn Thr Ser Glu Ile Ile Ser
1               5                  10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
        290                 295                 300

Arg Leu
305

<210> SEQ ID NO 3
<211> LENGTH: 918
<212> TYPE: DNA
<213> ORGANISM: Methanococcus jannaschii

<400> SEQUENCE: 3

```
atggacgaat ttgaaatgat aaagagaaac acatctgaaa ttatcagcga ggaagagtta      60
agagaggttt taaaaaaaga tgaaaaatct gcttacatag gttttgaacc aagtggtaaa     120
atacatttag ggcattatct ccaaataaaa aagatgattg attacaaaa tgctggattt     180
gatataatta tattgttggc tgatttacac gcctatttaa accagaaagg agagttggat     240
gagattagaa aaataggaga ttataacaaa aaagttttg aagcaatggg gttaaaggca     300
aaatatgttt atggaagtga attccagctt gataaggatt atacactgaa tgtctataga     360
ttggctttaa aaactacctt aaaaagagca agaaggagta tggaacttat agcaagagag     420
gatgaaaatc caaaggttgc tgaagttatc tatccaataa tgcaggttaa tgatattcat     480
tatttaggcg ttgatgttgc agttggaggg atggagcaga aaaaataca catgttagca     540
agggagcttt taccaaaaaa ggttgtttgt attcacaacc ctgtcttaac gggtttggat     600
ggagaaggaa agatgagttc ttcaaaaggg aattttatag ctgttgatga ctctccagaa     660
gagattaggg ctaagataaa gaaagcatac tgcccagctg gagttgttga aggaaatcca     720
ataatggaga tagctaaata cttccttgaa tatccttaa ccataaaaag gccagaaaaa     780
tttggtggag atttgacagt aatagctat gaggagttag agagtttatt taaaaataag     840
gaattgcatc caatggattt aaaaaatgct gtagctgaag aacttataa gattttagag     900
ccaattagaa agagatta                                                    918
```

<210> SEQ ID NO 4
<211> LENGTH: 306
<212> TYPE: PRT
<213> ORGANISM: Artificial
<220> FEATURE:
<223> OTHER INFORMATION: p-benzoyl-L-phenylalanine aminoacyl-tRNA
      synthetase

<400> SEQUENCE: 4

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Leu Tyr Gly Ser Pro Phe Gln Leu Asp Lys
            100                 105                 110

Asp Tyr Thr Leu Asn Val Tyr Arg Leu Ala Leu Lys Thr Thr Leu Lys

```
                    115                 120                 125
Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 5
<211> LENGTH: 918
<212> TYPE: DNA
<213> ORGANISM: Artificial
<220> FEATURE:
<223> OTHER INFORMATION: p-benzoyl-L-phenylalanine aminoacyl-tRNA
      synthetase

<400> SEQUENCE: 5
atggacgaat tgaaatgat  aaagagaaac acatctgaaa ttatcagcga ggaagagtta      60
agagaggttt taaaaaaaga tgaaaaatct gctggtatag gttttgaacc aagtggtaaa     120
atacatttag gcattatctc caaataaaaa agatgattg  atttacaaaa tgctggattt     180
gatataatta tattgttggc tgatttacac gcctatttaa accagaaagg agagttggat     240
gagattagaa aaataggaga ttataacaaa aaagtttttg aagcaatggg gttaaaggca     300
aaatatcttt atggaagtcc tttccagctt gataaggatt atacactgaa tgtctataga     360
ttggctttaa aaactacctt aaaaagagca agaaggagta tggaacttat agcaagagag     420
gatgaaaatc caaggttgc  tgaagttatc tatccaataa tgcaggttaa tacgagtcat     480
tatttaggcg ttgatgttgc agttggaggg atggagcaga aaaaatacac atgttagca      540 agggagcttt taccaaaaaa ggttgtttgt attcacaacc ctgtcttaac gggtttggat     600
ggagaaggaa agatgagttc ttcaaaaggg aattttatag ctgttgatga ctctccagaa     660
gagattaggg ctaagataaa gaaagcatac tgcccagctg gagttgttga aggaaatcca     720
ataatggaga tagctaaata cttccttgaa tatccttttaa ccataaaaag gccagaaaaa     780
tttggtggag atttgacagt taatagctat gaggagttag agagtttatt taaaaataag     840
gaattgcatc caatggattt aaaaaatgct gtagctgaag aacttataaa gattttagag     900
ccaattagaa agagatta                                                   918
```

<210> SEQ ID NO 6
<211> LENGTH: 306
<212> TYPE: PRT
<213> ORGANISM: Artificial
<220> FEATURE:
<223> OTHER INFORMATION: p-acetyl-L-phenylalanine aminoacyl-tRNA
      synthetase

<400> SEQUENCE: 6

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 7
<211> LENGTH: 918
<212> TYPE: DNA
<213> ORGANISM: Artificial
<220> FEATURE:
<223> OTHER INFORMATION: p-acetyl-L-phenylalanine aminoacyl-tRNA
      synthetase

<400> SEQUENCE: 7

```
atggacgaat tgaaatgat aaagagaaac acatctgaaa ttatcagcga ggaagagtta      60
agagaggttt taaaaaaga tgaaaaatct gctctgatag gttttgaacc aagtggtaaa     120
atacatttag ggcattatct ccaaataaaa aagatgattg atttacaaaa tgctggattt     180
gatataatta tattgttggc tgatttacac gcctatttaa accagaaagg agagttggat     240
gagattagaa aataggaga ttataacaaa aaagtttttg aagcaatggg gttaaaggca     300
aaatatgttt atggaagtga attccagctt gataaggatt atacactgaa tgtctataga     360
ttggctttaa aaactacctt aaaaagagca agaaggagta tggaacttat agcaagagag     420
gatgaaaatc caaggttgc tgaagttatc tatccaataa tgcaggttaa tggttgtcat     480
tatagggcg ttgatgttgc tgttggaggg atggagcaga gaaaaataca catgttagca     540
agggagcttt taccaaaaaa ggttgtttgt attcacaacc ctgtcttaac gggtttggat     600
ggagaaggaa agatgagttc ttcaaaaggg aattttatag ctgttgatga ctctccagaa     660
gagattaggg ctaagataaa gaaagcatac tgcccagctg gagttgttga aggaaatcca     720
ataatggaga tagctaaata cttccttgaa tatcctttaa ccataaaaag gccagaaaaa     780
tttggtggag atttgacagt taatagctat gaggagttag agagtttatt taaaaataag     840
gaattgcatc caatggattt aaaaaatgct gtagctgaag aacttataaa gattttagag     900
ccaattagaa agagatta                                                    918
```

```
<210> SEQ ID NO 8
<211> LENGTH: 306
<212> TYPE: PRT
<213> ORGANISM: Artificial
<220> FEATURE:
<223> OTHER INFORMATION: p-azido-L-phenylalanine aminoacyl-tRNA
      synthetase
```

<400> SEQUENCE: 8

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gln Ile His
145                 150                 155                 160

Ser Ser Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
```

```
                    180              185              190
Asn Pro Val Leu Thr Gly Leu Asp Gly Glu Gly Lys Met Ser Ser Ser
                195              200              205
Lys Gly Asn Phe Ile Ala Val Asp Asp Ser Pro Glu Glu Ile Arg Ala
210              215              220
Lys Ile Lys Lys Ala Tyr Cys Pro Ala Gly Val Val Glu Gly Asn Pro
225              230              235              240
Ile Met Glu Ile Ala Lys Tyr Phe Leu Glu Tyr Pro Leu Thr Ile Lys
                245              250              255
Arg Pro Glu Lys Phe Gly Gly Asp Leu Thr Val Asn Ser Tyr Glu Glu
            260              265              270
Leu Glu Ser Leu Phe Lys Asn Lys Glu Leu His Pro Met Asp Leu Lys
                275              280              285
Asn Ala Val Ala Glu Glu Leu Ile Lys Ile Leu Glu Pro Ile Arg Lys
            290              295              300
Arg Leu
305

<210> SEQ ID NO 9
<211> LENGTH: 918
<212> TYPE: DNA
<213> ORGANISM: Artificial
<220> FEATURE:
<223> OTHER INFORMATION: p-azido-L-phenylalanine aminoacyl-tRNA
      synthetase

<400> SEQUENCE: 9
atggacgaat tgaaatgat  aaagagaaac acatctgaaa ttatcagcga ggaagagtta        60
agagaggttt taaaaaaga  tgaaaaatct gctctgatag gttttgaacc aagtggtaaa       120
atacatttag gcattatct  ccaaataaaa aagatgattg atttacaaaa tgctggattt       180
gatataatta tattgttggc tgatttacac gcctatttaa accagaaagg agagttggat       240
gagattagaa aaataggaga ttataacaaa aaagttttg  aagcaatggg gttaaaggca       300
aaatatgttt atggaagtcc gttccagctt gataaggatt atactactga tgtctataga       360
ttggctttaa aaactacctt aaaaagagca agaaggagta tggaacttat agcaagagag       420
gatgaaaatc caaggttgc  tgaagttatc tatccaataa tgcaggttaa tcagattcat       480
tctagtggcg ttgatgttgc agttggaggg atggagcaga gaaaaataca catgttagca       540
agggagcttt taccaaaaaa ggttgttgt  attcacaacc ctgtcttaac gggtttggat       600
ggagaaggaa agatgagttc ttcaaaaggg aattttatag ctgttgatga ctctccagaa       660
gagattaggg ctaagataaa gaaagcatac tgcccagctg gagttgttga aggaaatcca       720
ataatggaga tagctaaata cttccttgaa tatcctttaa ccataaaaag gccagaaaaa       780
tttggtggag atttgacagt taatagctat gaggagttag agagtttatt taaaaataag       840
gaattgcatc caatggattt aaaaaatgct gtagctgaag aacttataaa gattttagag       900
ccaattagaa agagatta                                                     918

<210> SEQ ID NO 10
<211> LENGTH: 306
<212> TYPE: PRT
<213> ORGANISM: Artificial
<220> FEATURE:
<223> OTHER INFORMATION: p-iodo-L-phenylalanine aminoacyl-tRNA
      synthetase

<400> SEQUENCE: 10
```

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile
    50                  55                  60

Leu Leu Ala Asp Leu His Ala Tyr Leu Asn Gln Lys Gly Glu Leu Asp
65              70                  75                  80

Glu Ile Arg Lys Ile Gly Asp Tyr Asn Lys Lys Val Phe Glu Ala Met
            85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130             135                 140

Lys Val Ala Glu Val Ile Tyr Pro Ile Met Gln Val Asn Pro Leu His
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 11
<211> LENGTH: 918
<212> TYPE: DNA
<213> ORGANISM: Artificial
<220> FEATURE:
<223> OTHER INFORMATION: p-iodo-L-phenylalanine aminoacyl-tRNA
      synthetase

<400> SEQUENCE: 11
atggacgaat tgaaatgat aaagagaaac acatctgaaa ttatcagcga ggaagagtta      60
agagaggttt taaaaaaga tgaaaaatct gctctgatag ttttgaacc aagtggtaaa     120 atacatttag gcattatct ccaaataaaa agatgattg atttacaaa tgctggattt     180 gatataatta tattgttggc tgatttacac gcctattta accagaaagg agagttggat     240
gagattagaa aataggaga ttataacaaa aaagtttttg aagcaatggg gttaaaggca     300
```

-continued

```
aaatatgttt atggaagttc gttccagctt gataaggatt atacactgaa tgtctataga      360
ttggctttaa aaactacctt aaaaagagca agaaggagta tggaacttat agcaagagag      420
gatgaaaatc caaaggttgc tgaagttatc tatccaataa tgcaggttaa tcctcttcat      480
tatgagggcg ttgatgttgc agttggaggg atggagcaga gaaaaataca catgttagca      540
agggagcttt taccaaaaaa ggttgtttgt attcacaacc ctgtcttaac gggtttggat      600
ggagaaggaa agatgagttc ttcaaagggg aattttatag ctgttgatga ctctccagaa      660
gagattaggg ctaagataaa gaaagcatac tgcccagctg gagttgttga aggaaatcca      720
ataatggaga tagctaaata cttccttgaa tatcctttaa ccataaaaag gccagaaaaa      780
tttggtggag atttgacagt taatagctat gaggagttag agagtttatt taaaaataag      840
gaattgcatc caatggattt aaaaaatgct gtagctgaag aacttataaa gattttagag      900
ccaattagaa agagatta                                                   918

<210> SEQ ID NO 12
<211> LENGTH: 61
<212> TYPE: DNA
<213> ORGANISM: Artificial
<220> FEATURE:
<223> OTHER INFORMATION: mutant E. coli glnS promoter

<400> SEQUENCE: 12
cgattatcaa ttttaaaaaa ctaacagttg tcagcctgtc ccgcttataa tatcatacgc      60
c                                                                     61

<210> SEQ ID NO 13
<211> LENGTH: 60
<212> TYPE: DNA
<213> ORGANISM: Artificial
<220> FEATURE:
<223> OTHER INFORMATION: modified mutant E. coli glnS promoter TRN

<400> SEQUENCE: 13
cgattatcaa ttttaaaaaa ctaacagttg tcagcctgtc ccgctttaat atcatacgcc      60

<210> SEQ ID NO 14
<211> LENGTH: 44
<212> TYPE: DNA
<213> ORGANISM: Escherichia coli

<400> SEQUENCE: 14
actactttat gtagtctccg ccgtgtagca agaaattgag aagt                      44

<210> SEQ ID NO 15
<211> LENGTH: 42
<212> TYPE: DNA
<213> ORGANISM: Escherichia coli

<400> SEQUENCE: 15
aatttgcacg gcaaatttga agaggtttta actacatgtt at                        42

<210> SEQ ID NO 16
<211> LENGTH: 3
<212> TYPE: DNA
<213> ORGANISM: Escherichia coli

<400> SEQUENCE: 16 ttt                                                                   3
```

```
<210> SEQ ID NO 17
<211> LENGTH: 4
<212> TYPE: DNA
<213> ORGANISM: Escherichia coli

<400> SEQUENCE: 17 tcct                                                                       4

<210> SEQ ID NO 18
<211> LENGTH: 6
<212> TYPE: DNA
<213> ORGANISM: Escherichia coli

<400> SEQUENCE: 18 agatgt                                                                     6

<210> SEQ ID NO 19
<211> LENGTH: 9
<212> TYPE: DNA
<213> ORGANISM: Escherichia coli

<400> SEQUENCE: 19 tcttttttt                                                                  9

<210> SEQ ID NO 20
<211> LENGTH: 15
<212> TYPE: DNA
<213> ORGANISM: Escherichia coli

<400> SEQUENCE: 20
tcgaagaaac aatct                                                          15

<210> SEQ ID NO 21
<211> LENGTH: 20
<212> TYPE: DNA
<213> ORGANISM: Escherichia coli

<400> SEQUENCE: 21
ttattagaag ttgtgacaat                                                     20

<210> SEQ ID NO 22
<211> LENGTH: 34
<212> TYPE: DNA
<213> ORGANISM: Escherichia coli

<400> SEQUENCE: 22
tcttcttcga gtaagcggtt caccgcccgg ttat                                     34

<210> SEQ ID NO 23
<211> LENGTH: 34
<212> TYPE: DNA
<213> ORGANISM: Escherichia coli

<400> SEQUENCE: 23
aacgaggcga tatcaaaaaa agtaagatga ctgt                                     34

<210> SEQ ID NO 24
<211> LENGTH: 37
<212> TYPE: DNA
<213> ORGANISM: Escherichia coli

<400> SEQUENCE: 24
atttattcaa gacgcttacc ttgtaagtgc acccagt                                  37
```

```
<210> SEQ ID NO 25
<211> LENGTH: 39
<212> TYPE: DNA
<213> ORGANISM: Escherichia coli

<400> SEQUENCE: 25
aattttgcac ccagcaaact tggtacgtaa acgcatcgt                    39

<210> SEQ ID NO 26
<211> LENGTH: 42
<212> TYPE: DNA
<213> ORGANISM: Escherichia coli

<400> SEQUENCE: 26
aatttgcacg gcaaatttga agaggtttta actacatgtt at                42

<210> SEQ ID NO 27
<211> LENGTH: 42
<212> TYPE: DNA
<213> ORGANISM: Escherichia coli

<400> SEQUENCE: 27
aatttgcacg gcaaatttga agaggtttta actacatgtt at                42

<210> SEQ ID NO 28
<211> LENGTH: 47
<212> TYPE: DNA
<213> ORGANISM: Escherichia coli

<400> SEQUENCE: 28
aattctgaat gtatcgaata tgttcggcaa attcaaaacc aatttgt           47

<210> SEQ ID NO 29
<211> LENGTH: 54
<212> TYPE: DNA
<213> ORGANISM: Escherichia coli

<400> SEQUENCE: 29
gtttaaaaga catcggcgtc aagcggatgt ctggctgaaa ggcctgaaga attt   54

<210> SEQ ID NO 30
<211> LENGTH: 57
<212> TYPE: DNA
<213> ORGANISM: Escherichia coli

<400> SEQUENCE: 30
tttagtcccg gcgcttgagc tgcggtggta gtaataccgc gtaacaagat ttgtagt  57

<210> SEQ ID NO 31
<211> LENGTH: 62
<212> TYPE: DNA
<213> ORGANISM: Escherichia coli

<400> SEQUENCE: 31
tctcttactt gatatggctt tagtagcggt atcaatatca gcagtaaaat aaatttcccg  60
at                                                            62

<210> SEQ ID NO 32
<211> LENGTH: 62
<212> TYPE: DNA
<213> ORGANISM: Escherichia coli

<400> SEQUENCE: 32
aggcattttg ctattaaggg attgacgagg gcgtatctgc gcagtaagat gcgccccgca  60
``` tt                                                                    62

<210> SEQ ID NO 33
<211> LENGTH: 35
<212> TYPE: DNA
<213> ORGANISM: Escherichia coli

<400> SEQUENCE: 33
aattcgaaaa gcctgctcaa cgagcaggct ttttt                                35

<210> SEQ ID NO 34
<211> LENGTH: 64
<212> TYPE: DNA
<213> ORGANISM: Escherichia coli

<400> SEQUENCE: 34
atcagttagc gaaatatctt acttgcaatc ggtgtggaaa acggtagtat tagcagccac    60
gagt                                                                  64

<210> SEQ ID NO 35
<211> LENGTH: 41
<212> TYPE: DNA
<213> ORGANISM: Escherichia coli

<400> SEQUENCE: 35
aaaatcccaa gaaaaaacca acccttacgg ttggtttttt t                         41

<210> SEQ ID NO 36
<211> LENGTH: 30
<212> TYPE: DNA
<213> ORGANISM: Escherichia coli

<400> SEQUENCE: 36
attttgaacc ccgcttcggc ggggttttt                                      30

<210> SEQ ID NO 37
<211> LENGTH: 49
<212> TYPE: DNA
<213> ORGANISM: Artificial
<220> FEATURE:
<223> OTHER INFORMATION: synthetic oligonucleotide primer

<400> SEQUENCE: 37
gtgcacggct aactaagcgg cctgctgact ttctcgccga tcaaaaggc                 49

<210> SEQ ID NO 38
<211> LENGTH: 100
<212> TYPE: DNA
<213> ORGANISM: Artificial
<220> FEATURE:
<223> OTHER INFORMATION: synthetic oligonucleotide primer

<400> SEQUENCE: 38
ctttctcgcc gatcaaaagg catttttgcta ttaagggatt gacgagggcg tatctgcgca   60
gtaagatgcg ccccgcattc cggcggtagt tcagcagggc                           100

<210> SEQ ID NO 39
<211> LENGTH: 100
<212> TYPE: DNA
<213> ORGANISM: Artificial
<220> FEATURE:
<223> OTHER INFORMATION: synthetic oligonucleotide primer

<400> SEQUENCE: 39

```
ctttctcgcc gatcaaaagg cattttgcta ttaagggatt gacgagggcg tatctgcgca    60
gtaagatgcg ccccgcattc cggcggtagt tcagcagggc                         100
```

<210> SEQ ID NO 40
<211> LENGTH: 45
<212> TYPE: DNA
<213> ORGANISM: Artificial
<220> FEATURE:
<223> OTHER INFORMATION: synthetic oligonucleotide primer

<400> SEQUENCE: 40

```
gcataagctt atgcaaaaaa gcctgctcgt tgagcaggct tttcg                    45
```

<210> SEQ ID NO 41
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 41

```
agtctgatca gtgcacggct aactaagcgg                                     30
```

<210> SEQ ID NO 42
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 42

```
gcatctcgag atgcaaaaaa gcctgctcgt tg                                  32
```

<210> SEQ ID NO 43
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 43

```
ccgagctccc gggtcatc                                                  18
```

<210> SEQ ID NO 44
<211> LENGTH: 80
<212> TYPE: DNA
<213> ORGANISM: Artificial
<220> FEATURE:
<223> OTHER INFORMATION: synthetic oligonucleotide primer

<400> SEQUENCE: 44

```
ccgagctccc gggtcatcaa tcatccccat aatccttgtt agattatcaa ttttaaaaaa    60
ctaacagttg tcagcctgtc                                                80
```

<210> SEQ ID NO 45
<211> LENGTH: 80
<212> TYPE: DNA
<213> ORGANISM: Artificial
<220> FEATURE:
<223> OTHER INFORMATION: synthetic oligonucleotide primer

<400> SEQUENCE: 45

```
gtccatatgg gattcctcaa agcgtaaaca acgtataacg gcgtatgata ttataagcgg    60
gacaggctga caactgttag                                                80
```

<210> SEQ ID NO 46
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 46
gtccatatgg gattcctc                                               18

<210> SEQ ID NO 47
<211> LENGTH: 49
<212> TYPE: DNA
<213> ORGANISM: Artificial
<220> FEATURE:
<223> OTHER INFORMATION: synthetic oligonucleotide primer

<400> SEQUENCE: 47
gtgcacggct aactaagcgg cctgctgact ttctcgccga tcaaaaggc              49

<210> SEQ ID NO 48
<211> LENGTH: 48
<212> TYPE: DNA
<213> ORGANISM: Artificial
<220> FEATURE:
<223> OTHER INFORMATION: synthetic oligonucleotide primer

<400> SEQUENCE: 48
tacacggcgg agactacata aagtagttgg tccggcgggc cggatttg               48

<210> SEQ ID NO 49
<211> LENGTH: 52
<212> TYPE: DNA
<213> ORGANISM: Artificial
<220> FEATURE:
<223> OTHER INFORMATION: synthetic oligonucleotide primer

<400> SEQUENCE: 49
gtagtctccg ccgtgtagca agaaattgag aagtccggcg gtagttcagc ag          52

<210> SEQ ID NO 50
<211> LENGTH: 49
<212> TYPE: DNA
<213> ORGANISM: Artificial
<220> FEATURE:
<223> OTHER INFORMATION: synthetic oligonucleotide primer

<400> SEQUENCE: 50
aaacctcttc aaatttgccg tgcaaatttg gtccggcggg ccggatttg              49

<210> SEQ ID NO 51
<211> LENGTH: 50
<212> TYPE: DNA
<213> ORGANISM: Artificial
<220> FEATURE:
<223> OTHER INFORMATION: synthetic oligonucleotide primer

<400> SEQUENCE: 51
gcaaatttga agaggtttta actacatgtt atccggcggt agttcagcag             50

<210> SEQ ID NO 52
<211> LENGTH: 32
<212> TYPE: DNA
<213> ORGANISM: Artificial
<220> FEATURE:
<223> OTHER INFORMATION: synthetic oligonucleotide primer

```
<400> SEQUENCE: 52
gcatctcgag atgcaaaaaa gcctgctcgt tg                                32

<210> SEQ ID NO 53
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 53
atcagtgcac ggctaactaa gcgg                                        24

<210> SEQ ID NO 54
<211> LENGTH: 35
<212> TYPE: DNA
<213> ORGANISM: Artificial
<220> FEATURE:
<223> OTHER INFORMATION: synthetic oligonucleotide primer

<400> SEQUENCE: 54
gctggcatgc atgcaaaaaa gcctgctcgt tgagc                            35

<210> SEQ ID NO 55
<211> LENGTH: 31
<212> TYPE: DNA
<213> ORGANISM: Artificial
<220> FEATURE:
<223> OTHER INFORMATION: synthetic oligonucleotide primer

<400> SEQUENCE: 55
atcagcatgc ggctaactaa gcggcctgct g                                31

<210> SEQ ID NO 56
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 56
gctgctcgag atgcaaaaaa gcctgc                                      26

<210> SEQ ID NO 57
<211> LENGTH: 18
<212> TYPE: PRT
<213> ORGANISM: Artificial
<220> FEATURE:
<223> OTHER INFORMATION: leader sequence

<400> SEQUENCE: 57

Met Asp Pro Leu Val Thr Ala Ala Ser Val Leu Glu Phe Gly Leu Phe
1               5                   10                  15

Glu Thr

<210> SEQ ID NO 58
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 58
ccctgctgaa ctaccgcc                                               18
```

SYSTEMS FOR THE EXPRESSION OF ORTHOGONAL TRANSLATION COMPONENTS IN EUBACTERIAL HOST CELLS

CROSS-REFERENCE TO RELATED APPLICATIONS

This application claims priority to and benefit of:
U.S. Provisional Patent Appl. Ser. No. 60/780,973, filed Mar. 9, 2006;
U.S. Provisional Patent Appl. Ser. No. 60/783,497, filed Mar. 17, 2006; and
U.S. Provisional Patent Appl. Ser. No. 60/855,336, filed Oct. 29, 2006,
the contents of each of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with U.S. Government support under Contract No. ER46051 from the Department of Energy. The U.S. Government may have certain rights to the invention.

FIELD OF THE INVENTION

The invention relates to the field of protein chemistry, e.g., translation biochemistry. The invention relates to compositions and methods for the in vivo production of polypeptides comprising one or more unnatural amino acids.

BACKGROUND OF THE INVENTION

The study of protein structure and function has historically relied upon the chemical properties that are available using the R-groups of the naturally occurring amino acids. Unfortunately, every known organism, from bacteria to humans, encodes the same twenty common amino acids (with the rare exceptions of selenocysteine (see, e.g., Bock et al., (1991), *Molecular Microbiology* 5:515-20) and pyrrolysine (see, e.g., Srinivasan, et al., (2002), *Science* 296:1459-62). This limited selection of R-groups has restricted the study of protein structure and function, where the studies are confined by the chemical properties of the naturally occurring amino acids.

A general methodology has been developed for the in vivo site-specific incorporation of chemically diverse unnatural amino acids with novel physicochemical and biological properties into proteins in both prokaryotic and eukaryotic organisms (Wang et al., Science 292, 498-500 (2001); Chin, et al. Science 301, 964-967 (2003); Wang and Schultz, Angew. Chem. Int. Ed. 44, 34-66 (2005)). This method relies on a unique codon-tRNA pair and corresponding aminoacyl-tRNA synthetase (aaRS, or simply RS) for each unnatural amino acid that functions efficiently in protein translation, but do not cross-react with any of the endogenous tRNAs, RSs, amino acids or codons in the host organism (i.e., it must be orthogonal). The use of such orthogonal tRNA-RS pairs has made it possible to genetically encode a large number of structurally diverse amino acids including those with unique chemical (Wang et al., *Proc. Natl. Sci. Acad. USA.* 100, 56-61 (2003)) and photochemical reactivity (Chin et al., *Proc. Natl. Acad. Sci. USA* 99, 11020-11024 (2002); Wu et al., J. Am. Chem. Soc., 126, 14306-14307 (2004)) as well as glycosylated (Zhang et al., Science 303, 371-373 (2004)) fluorescent (Wang and Schultz, Angew. Chem. Int. Ed. 44:34-66 (2005)), metal binding (Wang and Schultz, Angew. Chem. Int. Ed. 44:34-66 (2005)) and redox active amino acids (Alfonta et al., J. Am. Chem. Soc. 125:14662-14663 (2003)). One particular mutant MjtRNA-Tyr(CUA)-MjTyrRS pair has been particularly useful for encoding new amino acids in *E. coli* (Wang and Schultz, Chem. Biol. 8:883-890 (2001)).

However, despite the success of this technique in incorporating a diverse array of unnatural amino acids in vivo, the efficiency of the expression system for the production of mutant proteins containing unnatural amino acids has not been optimized, and suppression efficiency of the orthogonal system to overcome the selector codon can be poor. There is a need in the art to develop reagents to improve the suppression efficiency of orthogonal translation systems. The invention described herein fulfills these and other needs, as will be apparent upon review of the following disclosure.

SUMMARY OF THE INVENTION

The invention provides improved expression vector systems useful for the efficient bacterial expression of mutant proteins comprising one or more unnatural amino acid at specific sites genetically coded by selector codons (e.g., amber nonsense codons). These systems result in significantly improved efficiency in the incorporation of unnatural amino acids into proteins in eubacteria (e.g., *E. coli*). The novel expression vector features of the invention are broadly compatible with a variety of *E. coli* expression vector backbones and *E. coli* strains, and are also readily adapted for the expression of other proteins or tRNAs of interest, in addition to the expression of orthogonal aminoacyl-tRNA synthetases or orthogonal suppressor tRNAs.

These orthogonal translation technology utilized by the invention is known in the art. However, the invention is not limited in any aspect with regard to the particular orthogonal translation components that are used (i.e., the particular orthogonal aminoacyl-tRNA synthetase or the particular orthogonal suppressor tRNA). Indeed, the invention provides improved compositions and methods that find broad use in bacterial expression vector systems that are not limited to the expression of orthogonal aminoacyl-tRNA synthetases or suppressor tRNAs.

In some aspects, the invention provides various nucleic acid constructs. These embodiments include, for example:

Construct A: Constructs having promoter and terminator nucleotide sequences derived from an *Escherichia coli* proline tRNA gene and an expressible nucleotide sequence, where the promoter and terminator sequences are both operatively linked to the expressible nucleotide sequence, and wherein the expressible nucleotide sequence is heterologous to the promoter and terminator nucleotide sequences.

Construct B: Constructs having a promoter nucleotide sequence that is a modified *E. coli* glnS promoter having a nucleotide sequence of SEQ ID NO: 13 and an expressible nucleotide sequence, wherein the modified *E. coli* glnS promoter nucleotide sequence is operatively linked to the expressible nucleotide sequence.

In some aspects, the features of constructs A and B are used in the same vector, and where the expressible nucleotide sequences are different.

Construct C: Constructs having a nucleotide sequence encoding an orthogonal tRNA (O-tRNA) and a nucleotide sequence encoding an orthogonal aminoacyl-tRNA synthetase (O-RS), wherein the O-RS preferentially aminoacylates the O-tRNA with an unnatural amino acid.

Construct D: Constructs having a polycistronic operon comprising a plurality of tRNA gene nucleotide sequences, where at least one tRNA gene is separated from at least one adjacent tRNA gene by a heterologous polynucleotide linker derived from a naturally occurring polynucleotide linker from a naturally occurring tRNA operon.

In some embodiments, in the case where constructs A, B and C are simultaneously used, expressible nucleotide sequence in A encodes the O-tRNA, and where the expressible nucleotide sequence in B encodes the O-RS.

In some embodiments of these constructs, the *E. coli* proline tRNA gene is selected from *E. coli* proK, proL and proM tRNA genes. In some embodiments, the *E. coli* proline tRNA promoter and terminator sequences derived from the promoter and terminator sequences of *E. coli* proK provided in SEQ ID NOS: 32 (promoter) and 33 (terminator), respectively. In some embodiments, the expressible nucleotide sequence in construct A is a polycistronic operon comprising a plurality of one or more nucleotide sequences. In some embodiments, the expressible nucleotide sequence in construct A encodes a tRNA, e.g., where the tRNA is derived from one or more Archaea tRNA, or where the tRNA is encoded by a nucleotide sequence of SEQ ID NO: 1 (MjtRNA-Tyr(CUA)). In some embodiments, the expressible nucleotide sequence is a polycistronic operon comprising a plurality of the nucleotide sequence of SEQ ID NO: 1 (MjtRNA-Tyr(CUA)). In some aspects, the expressible nucleotide sequence is a plurality of the polycistronic operon.

When construct B is used, the expressible nucleotide sequence can encode a polypeptide, e.g., an aminoacyl-tRNA synthetase. In some aspects, the expressible nucleotide sequence of construct B encodes an orthogonal aminoacyl-tRNA synthetase (O-RS), where the O-RS preferentially aminoacylates a corresponding O-tRNA with an unnatural amino acid. In some aspects, the O-RS is derived from a *Methanococcus jannaschii* aminoacyl-tRNA synthetase, e.g., a *Methanococcus jannaschii* tyrosyl-tRNA synthetase. In these aspects, optionally the O-RS has an aspartic acid to arginine substitution at amino acid position 286 or at a position analogous to position 286, relative to the amino acid sequence of wild-type *Methanococcus jannaschii* tyrosyl-tRNA synthetase provided in SEQ ID NO: 2 (wild type Mj-tRNA-Tyr RS).

These construct of the invention can be used in a host cell, e.g., a eubacterial host cell such as an *E. coli* cell.

Where construct D is used, the polycistronic operon can comprise a plurality of identical heterologous polynucleotide linkers. In some of these cases, at least two of the heterologous polynucleotide linkers are different. This polycistronic operon of D can comprise a plurality of heterologous polynucleotide linkers. In some embodiments, the heterologous polynucleotide linker of D can comprise a 5' terminal thymidine nucleotide, a 3' terminal adenosine nucleotide, or both a 5' terminal thymidine nucleotide and a 3' terminal adenosine nucleotide. The heterologous polynucleotide linker can be derived from the naturally occurring polynucleotide linker located between the endogenous *Escherichia coli* tRNA genes selected from: valU and valX; ileT and alaT; serV and argV; valV and valW; glyT and thrT; metT and leuW; glnW and metU; hisR and leuT; glnU and glnW; leuP and leuV; glnV and glnX; alaW and alaX; ileU and alaU; ileV and alaV; metU and glnV; glyW and cysT; argX and hisR; and argY and argZ. In some aspects, the heterologous polynucleotide linker of D is derived from the nucleotide sequence of SEQ ID NO: 14 (valU/valX linker) or 15 (ileT/alaT linker).

In other aspects, the invention provides translation systems for the expression of a polypeptide of interest comprising at least one unnatural amino acid at a specified position. These systems of the invention contain:

(a) an unnatural amino acid;
(b) a nucleic acid construct, the construct comprising a nucleotide sequence encoding an orthogonal tRNA (O-tRNA) and a nucleotide sequence encoding an orthogonal aminoacyl-tRNA synthetase (O-RS), where the O-RS preferentially aminoacylates the O-tRNA with the unnatural amino acid; and
(c) a polynucleotide encoding the polypeptide of interest, the polynucleotide comprising at least one selector codon that is recognized by the O-tRNA, where the position of the selector codon in the polynucleotide controls the specified position of the unnatural amino acid in the polypeptide of interest upon expression of the polynucleotide to produce the polypeptide.

In these systems of the invention, the nucleic acid construct can comprise any one or more features listed as follows:

(1) promoter and terminator nucleotide sequences derived from an *Escherichia coli* proline tRNA gene, where the promoter and terminator sequences are both operatively linked to the nucleotide sequence comprising or encoding the O-tRNA, and where the O-tRNA is heterologous to the promoter and terminator nucleotide sequences;

(2) a nucleotide sequence corresponding to a modified *E. coli* glnS promoter having a nucleotide sequence of SEQ ID NO: 13, where the modified *E. coli* glnS nucleotide sequence is operatively linked to the nucleotide sequence encoding the O-RS; or (3) a polycistronic operon comprising a plurality of the O-tRNA gene nucleotide sequences, where at least one O-tRNA gene is separated from at least one adjacent O-tRNA gene by a heterologous polynucleotide linker derived from a naturally occurring polynucleotide linker from a naturally occurring tRNA operon.

In these systems, the *E. coli* proline tRNA gene can be selected from *E. coli* proK, proL and proM tRNA genes. The *E. coli* proline tRNA promoter and terminator sequences can be derived from the promoter and terminator sequences of *E. coli* proK provided in SEQ ID NOS: 32 (promoter) and 33 (terminator), respectively. The polycistronic operon can comprise a plurality of identical heterologous polynucleotide linkers, e.g., where at least two of the heterologous polynucleotide linkers are different. In these systems, the heterologous polynucleotide linker can comprise a 5' terminal thymidine nucleotide, or a 3' terminal adenosine nucleotide, or both a 5' terminal thymidine nucleotide and a 3' terminal adenosine nucleotide. The heterologous polynucleotide linker can be derived from a naturally occurring polynucleotide linker located between the endogenous *Escherichia coli* tRNA genes selected from: valU and valX; ileT and alaT; serV and argV; valV and valW; glyT and thrT; metT and leuW; glnW and metU; hisR and leuT; glnU and glnW; leuP and leuV; glnV and glnX; alaW and alaX; ileU and alaU; ileV and alaV; metU and glnV; glyW and cysT; argX and hisR; and argY and argZ. In some aspects, the heterologous polynucleotide linker is derived from the nucleotide sequence of SEQ ID NO: 14 (valU/valX linker) or 15 (ileT/alaT linker).

In these systems, the O-tRNA can be derived from one or more Archaea tRNA. In some system aspects, the nucleotide sequence encoding an O-tRNA is a polycistronic operon comprising a plurality of nucleotide sequences encoding an O-tRNA. In some aspects, the nucleotide sequence encoding an O-tRNA comprises a nucleotide sequence of SEQ ID NO: 1 (MjtRNA-Tyr(CUA)). In other aspects of the system, the nucleotide sequence encoding an O-tRNA is a polycistronic operon comprising a plurality of the nucleotide sequence of SEQ ID NO: 1 (MjtRNA-Tyr(CUA)).

In other aspects, the translation system can utilize an O-RS that is derived from a *Methanococcus jannaschii* aminoacyl-tRNA synthetase, e.g., a *Methanococcus jannaschii* tyrosyl-tRNA synthetase. In some aspects, this O-RS has an aspartic acid to arginine substitution at amino acid position 286 or at a position analogous to position 286, relative to the amino acid sequence of wild-type *Methanococcus jannaschii* tyrosyl-tRNA synthetase provided in SEQ ID NO: 2 (wild type Mj-tRNA$^{Tyr}$RS).

In some aspects of this systems, the components are contained in a host cell, e.g., a eubacterial host cell such as an *E. coli* cell.

In other aspects, the invention provides methods for producing, in a host cell, a polypeptide of interest comprising an unnatural amino acid at a specified position. These methods have the following steps:
  (a) providing: (i) an unnatural amino acid; (ii) a nucleic acid construct comprising a nucleotide sequence encoding an orthogonal tRNA (O-tRNA) and a nucleotide sequence encoding an orthogonal aminoacyl-tRNA synthetase (O-RS), where the O-RS preferentially aminoacylates the O-tRNA with the unnatural amino acid; and, (iii) a polynucleotide encoding the polypeptide of interest, the polynucleotide comprising at least one selector codon that is recognized by the O-tRNA, and where the position of the selector codon correlates to the specified position of the unnatural amino acid in the polypeptide of interest; (iv) a host cell comprising (i), (ii) and (iii); and
  (b) growing the host cell; and
  (c) incorporating the unnatural amino acid at the specified position in the polypeptide during translation of the polypeptide in the host cell, thereby producing the polypeptide of interest comprising the unnatural amino acid at the specified position.

In these methods, the O-tRNA can be derived from one or more Archaea tRNA. The construct used in the methods can utilize a polycistronic operon comprising a plurality of nucleotide sequences encoding one or more O-tRNA species. The O-tRNA used can comprising a nucleotide sequence of SEQ ID NO: 1 (MjtRNA-Tyr(CUA)), or alternatively, a polycistronic operon comprising a plurality of the nucleotide sequence of SEQ ID NO: 1 (MjtRNA-Tyr(CUA)). In some aspects of this method, the O-RS can be derived from a *Methanococcus jannaschii* aminoacyl-tRNA synthetase, e.g., a *Methanococcus jannaschii* tyrosyl-tRNA synthetase. In some aspects, the O-RS has an aspartic acid to arginine substitution at amino acid position 286 or at a position analogous to position 286, relative to the amino acid sequence of wild-type *Methanococcus jannaschii* tyrosyl-tRNA synthetase provided in SEQ ID NO: 2 (wild type Mj-tRNA$^{Tyr}$RS).

These methods for producing the polypeptides can utilize a variety of nucleic acid constructs, where the constructs can use any of:
  (I) promoter and terminator nucleotide sequences derived from an *Escherichia coli* proline tRNA gene, where the promoter and terminator sequences are both operatively linked to the nucleotide sequence encoding the O-tRNA, and where the nucleotide sequence encoding the O-tRNA is heterologous to the promoter and terminator sequences;
  (II) a promoter nucleotide sequence corresponding to a modified *E. coli* glnS promoter having a nucleotide sequence of SEQ ID NO: 13, where the modified *E. coli* glnS nucleotide sequence is operatively linked to the nucleotide sequence encoding the O-RS; and
  (III) a polycistronic operon comprising a plurality of O-tRNA gene nucleotide sequences, where at least one O-tRNA gene is separated from at least one adjacent O-tRNA gene by a heterologous polynucleotide linker derived from a naturally occurring polynucleotide linker from a naturally occurring tRNA operon.

Where (I) is used, the *E. coli* proline tRNA can be selected from *E. coli* proK, proL and proM tRNA. When the *E. coli* proK is used, SEQ ID NOS: 32 (promoter) and 33 (terminator) can be utilized.

Where a polycistronic operon of (III) is used, a plurality of identical heterologous polynucleotide linkers can be utilized, alternatively where at least two of the heterologous polynucleotide linkers are different. In some aspects, the polycistronic operon of (III) uses a 5' terminal thymidine nucleotide, a 3' terminal adenosine nucleotide, or both a 5' terminal thymidine nucleotide and a 3' terminal adenosine nucleotide. Further, the heterologous polynucleotide linker can be derived from the naturally occurring polynucleotide linker located between the endogenous *Escherichia coli* tRNA genes selected from: valU and valX; ileT and alaT; serV and argV; valV and valW; glyT and thrT; metT and leuW; glnW and metU; hisR and leuT; glnU and glnW; leuP and leuV; glnV and glnX; alaW and alaX; ileU and alaU; ileV and alaV; metU and glnV; glyW and cysT; argX and hisR; and argY and argZ. In particular, the nucleotide sequence of SEQ ID NO: 14 (valU/valX linker) or 15 (ileT/alaT linker) can be used. In some aspects, the host cell is a eubacterial host cell, e.g., an *Escherichia coli* host cell.

In other aspects, the invention provides methods for producing proteins having unnatural amino acids. These methods use novel vector systems of the invention, making possible improved production of the proteins containing the unnatural amino acids. These methods for producing a polypeptide of interest comprising an unnatural amino acid at a specified position are accomplished in a host cell, where the steps of the method include: (a) providing:
  (i) an unnatural amino acid;
  (ii) a nucleic acid construct comprising a nucleotide sequence encoding an orthogonal tRNA (O-tRNA);
  (iii) a nucleic acid construct comprising a nucleotide sequence encoding an orthogonal aminoacyl-tRNA synthetase (O-RS), where the O-RS preferentially aminoacylates the O-tRNA with the unnatural amino acid;
  (iv) a polynucleotide encoding the polypeptide of interest, the polynucleotide comprising at least one selector codon that is recognized by the O-tRNA, and where the position of the selector codon correlates to the specified position of the unnatural amino acid in the polypeptide of interest; and,
  (v) a host cell comprising (i), (ii), (iii) and (iv).

These methods require that the nucleic acid constructs of (ii) and (iii) collectively comprise at least one of the following three features:
  (I) promoter and terminator nucleotide sequences derived from an *Escherichia coli* proline tRNA gene, where the promoter and terminator sequences are both operatively linked to the nucleotide sequence encoding the O-tRNA, and where the nucleotide sequence encoding the O-tRNA is heterologous to the promoter and terminator sequences;
  (II) a promoter nucleotide sequence corresponding to a modified *E. coli* glnS promoter having a nucleotide sequence of SEQ ID NO: 13, where the modified *E. coli* glnS nucleotide sequence is operatively linked to the nucleotide sequence encoding the O-RS; and (III) a polycistronic operon comprising a plurality of O-tRNA gene nucleotide sequences, where at least one O-tRNA gene is separated from at least one adjacent O-tRNA gene by a heterologous polynucleotide linker derived from a naturally occurring polynucleotide linker from a naturally occurring tRNA operon.

The method is accomplished by (b) growing the host cell; and (c) incorporating the unnatural amino acid at the specified position in the polypeptide during translation of the polypeptide in the host cell, thereby producing the polypeptide of interest comprising the unnatural amino acid at the specified position.

Optionally, the nucleotide sequence encoding an O-tRNA is derived from one or more Archaea tRNA. The O-tRNA can be provided in a polycistronic operon comprising a plurality of nucleotide sequences encoding one or more O-tRNA species. In some aspects, the nucleotide sequence encoding an O-tRNA comprises a nucleotide sequence of SEQ ID NO: 1 (MjtRNA-Tyr(CUA)). A polycistronic operon can optionally utilize a plurality of the nucleotide sequence of SEQ ID NO: 1 (MjtRNA-Tyr(CUA)).

In other aspects, the O-RS is derived from a *Methanococcus jannaschii* aminoacyl-tRNA synthetase, such as a *Methanococcus jannaschii* tyrosyl-tRNA synthetase. Optionally, the O-RS has an aspartic acid to arginine substitution at amino acid position 286 or at a position analogous to position 286, relative to the amino acid sequence of wild-type *Methanococcus jannaschii* tyrosyl-tRNA synthetase provided in SEQ ID NO: 2 (wild type Mj-tRNA$^{Tyr}$RS).

In other embodiments of these methods, the nucleic acid construct of (I) comprises an *E. coli* proline tRNA selected from *E. coli* proK, proL and proM tRNA. Further, the construct of (I) can use the promoter and terminator sequences of *E. coli* proK provided in SEQ ID NOS: 32 (promoter) and 33 (terminator), respectively.

In other method embodiments, the nucleic acid construct of (III) uses plurality of identical heterologous polynucleotide linkers. Optionally, at least two of the heterologous polynucleotide linkers are different.

Optionally, the polycistronic operon of (III) in these methods uses a heterologous polynucleotide linker comprising a 5' terminal thymidine nucleotide, a 3' terminal adenosine nucleotide, or both a 5' terminal thymidine nucleotide and a 3' terminal adenosine nucleotide. The heterologous polynucleotide linker used herein can be derived from a naturally occurring polynucleotide linker located between the endogenous *Escherichia coli* tRNA genes selected from: valU and valX; ileT and alaT; serV and argV; valV and valW; glyT and thrT; metT and leuW; glnW and met U; hisR and leuT; glnU and glnW, leuP and leuV; glnV and glnX; alaW and alaX; ileU and alaU; ileV and ala V; metU and glnV; glyW and cysT; argX and hisR; and argY and argZ. For example, the heterologous polynucleotide linker can be derived from the nucleotide sequence of SEQ ID NO: 14 (valU/valX linker) or 15 (ileT/alaT linker). Optionally, these methods are accomplished in a eubacterial host cell such as *Escherichia coli*.

In other aspects, the invention also provides translation systems for the expression of a polypeptide of interest that has at least one unnatural amino acid at a specified position. Essentially, these systems include:

(a) an unnatural amino acid;
(b) a nucleic acid construct, the construct comprising a nucleotide sequence encoding an orthogonal tRNA (O-tRNA) and a nucleotide sequence encoding an orthogonal aminoacyl-tRNA synthetase (O-RS), where the O-RS preferentially aminoacylates the O-tRNA with the unnatural amino acid; and
(c) a polynucleotide encoding the polypeptide of interest, the polynucleotide comprising at least one selector codon that is recognized by the O-tRNA, where the position of the selector codon in the polynucleotide controls the specified position of the unnatural amino acid in the polypeptide of interest upon expression of the polynucleotide to produce the polypeptide.

Optionally, these system components are integrated in a host cell.

In still other embodiments, the invention provides methods for producing a polypeptide of interest having an unnatural amino acid at a specified position. Essentially, these methods use the steps of:

(a) providing a translation system, the translation system comprising:
  (i) an unnatural amino acid;
  (ii) a nucleic acid construct comprising a nucleotide sequence encoding an orthogonal tRNA (O-tRNA) and a nucleotide sequence encoding an orthogonal aminoacyl-tRNA synthetase (O-RS), where the O-RS preferentially aminoacylates the O-tRNA with the unnatural amino acid; and,
  (iii) a polynucleotide encoding the polypeptide of interest, the polynucleotide comprising at least one selector codon that is recognized by the O-tRNA, and where the position of the selector codon correlates to the specified position of the unnatural amino acid in the polypeptide of interest;
  (iv) a host cell comprising (i), (ii) and (iii).

These methods further require (b) growing the host cell; and (c) incorporating the unnatural amino acid at the specified position in the polypeptide during translation of the polypeptide in the host cell, thereby producing the polypeptide of interest comprising the unnatural amino acid at the specified position.

Definitions

Before describing the invention in detail, it is to be understood that this invention is not limited to particular biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes combinations of two or more cells; reference to "a polynucleotide" includes, as a practical matter, many copies of that polynucleotide.

Unless defined herein and below in the reminder of the specification, all technical and scientific terms used herein have the same meaning as commonly understood by one of ordinary skill in the art to which the invention pertains. In describing and claiming the present invention, the following terminology will be used in accordance with the definitions set out below.

Orthogonal: As used herein, the term "orthogonal" refers to a molecule (e.g., an orthogonal tRNA (O-tRNA) and/or an orthogonal aminoacyl-tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) as compared to that of a control, e.g., a corresponding tRNA/RS endogenous pair, or an active orthogonal pair (e.g., a tyrosyl orthogonal tRNA/RS pair).

Orthogonal tyrosyl-tRNA: As used herein, an orthogonal tyrosyl-tRNA (tyrosyl-O-tRNA) is a tRNA that is orthogonal to a translation system of interest, where the tRNA is: (1) identical or substantially similar to a naturally occurring tyrosyl-tRNA, (2) derived from a naturally occurring tyrosyl-tRNA by natural or artificial mutagenesis, (3) derived by any process that takes a sequence of a wild-type or mutant tyrosyl-tRNA sequence of (1) or (2) into account, (4) homologous to a wild-type or mutant tyrosyl-tRNA; (5) homologous to any example tRNA that is designated as a substrate for a tyrosyl-tRNA synthetase, e.g., synthetases of SEQ ID NOS: 2, 4, 6, 8 or 10, (6) a conservative variant of any example tRNA that is designated as a substrate for a tyrosyl-tRNA synthetase in, e.g., the O-tRNA of SEQ ID NO: 1. The tyrosyl-tRNA can exist charged with an amino acid, or in an uncharged state. It is also to be understood that a "tyrosyl-O-tRNA" optionally is charged (aminoacylated) by a cognate synthetase with an amino acid other than tyrosine or leucine, respectively, e.g., with an unnatural amino acid. Indeed, it will be appreciated that a tyrosyl-O-tRNA of the invention is advantageously used to insert essentially any amino acid, whether natural or artificial, into a growing polypeptide, during translation, in response to a selector codon.

Orthogonal tyrosyl amino acid synthetase: As used herein, an orthogonal tyrosyl amino acid synthetase (tyrosyl-O-RS) is an enzyme that preferentially aminoacylates the tyrosyl-O-tRNA with an amino acid in a translation system of interest. The amino acid that the tyrosyl-O-RS loads onto the tyrosyl-O-tRNA can be any amino acid, whether natural, unnatural or artificial, and is not limited herein. The synthetase is optionally the same as or homologous to a naturally occurring tyrosyl amino acid synthetase, or the same as or homologous to a synthetase designated as an O-RS in, e.g., SEQ ID NOS: 4, 6, 8 or 10. For example, the O-RS can be a conservative variant of a tyrosyl-O-RS of e.g., SEQ ID NOS: 4, 6, 8 or 10, and/or can be at least 50%, 60%, 70%, 80%, 90%, 95%, 98%, 99% or more identical in sequence to an O-RS of, e.g., SEQ ID NOS: 4, 6, 8 or 10.

Cognate: The term "cognate" refers to components that function together, e.g., an orthogonal tRNA and an orthogonal aminoacyl-tRNA synthetase. The components can also be referred to as being complementary.

Preferentially aminoacylates: As used herein in reference to orthogonal translation systems, an O-RS "preferentially aminoacylates" a cognate O-tRNA when the O-RS charges the O-tRNA with an amino acid more efficiently than it charges any endogenous tRNA in an expression system. That is, when the O-tRNA and any given endogenous tRNA are present in a translation system in approximately equal molar ratios, the O-RS will charge the O-tRNA more frequently than it will charge the endogenous tRNA. Preferably, the relative ratio of O-tRNA charged by the O-RS to endogenous tRNA charged by the O-RS is high, preferably resulting in the O-RS charging the O-tRNA exclusively, or nearly exclusively, when the O-tRNA and endogenous tRNA are present in equal molar concentrations in the translation system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The O-RS "preferentially aminoacylates an O-tRNA with an unnatural amino acid" when (a) the O-RS preferentially aminoacylates the O-tRNA compared to an endogenous tRNA, and (b) where that aminoacylation is specific for the unnatural amino acid, as compared to aminoacylation of the O-tRNA by the O-RS with any natural amino acid. That is, when the unnatural and natural amino acids are present in equal molar amounts in a translation system comprising the O-RS and O-tRNA, the O-RS will load the O-tRNA with the unnatural amino acid more frequently than with the natural amino acid. Preferably, the relative ratio of O-tRNA charged with the unnatural amino acid to O-tRNA charged with the natural amino acid is high. More preferably, O-RS charges the O-tRNA exclusively, or nearly exclusively, with the unnatural amino acid. The relative ratio between charging of the O-tRNA with the unnatural amino acid and charging of the O-tRNA with the natural amino acid, when both the natural and unnatural amino acids are present in the translation system in equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

Selector codon: The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Suppressor tRNA: A suppressor tRNA is a tRNA that alters the reading of a messenger RNA (mRNA) in a given translation system, e.g., by providing a mechanism for incorporating an amino acid into a polypeptide chain in response to a selector codon. For example, a suppressor tRNA can read through, e.g., a stop codon (e.g., an amber, ocher or opal codon), a four base codon, a rare codon, etc.

Suppression activity: As used herein, the term "suppression activity" refers, in general, to the ability of a tRNA (e.g., a suppressor tRNA) to allow translational read-through of a codon (e.g., a selector codon that is an amber codon or a 4-or-more base codon) that would otherwise result in the termination of translation or mistranslation (e.g., frame-shifting). Suppression activity of a suppressor tRNA can be expressed as a percentage of translational read-through activity observed compared to a second suppressor tRNA, or as compared to a control system, e.g., a control system lacking an O-RS.

The present invention provides various methods by which suppression activity can be quantitated. Percent suppression of a particular O-tRNA and O-RS against a selector codon (e.g., an amber codon) of interest refers to the percentage of activity of a given expressed test marker (e.g., LacZ), that includes a selector codon, in a nucleic acid encoding the expressed test marker, in a translation system of interest, where the translation system of interest includes an O-RS and an O-tRNA, as compared to a positive control construct, where the positive control lacks the O-tRNA, the O-RS and the selector codon. Thus, for example, if an active positive control marker construct that lacks a selector codon has an observed activity of X in a given translation system, in units relevant to the marker assay at issue, then percent suppression of a test construct comprising the selector codon is the percentage of X that the test marker construct displays under essentially the same environmental conditions as the positive control marker was expressed under, except that the test marker construct is expressed in a translation system that also includes the O-tRNA and the O-RS. Typically, the translation system expressing the test marker also includes an amino acid that is recognized by the O-RS and O-tRNA. Optionally, the percent suppression measurement can be refined by comparison of the test marker to a "background" or "negative" control marker construct, which includes the same selector codon as the test marker, but in a system that does not include the O-tRNA, O-RS and/or relevant amino acid recognized by the O-tRNA and/or O-RS. This negative control is useful in normalizing percent suppression measurements to account for background signal effects from the marker in the translation system of interest.

Suppression efficiency can be determined by any of a number of assays known in the art. For example, a β-galactosidase reporter assay can be used, e.g., a derivatived lacZ plasmid (where the construct has a selector codon in the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Translation system: The term "translation system" refers to the components that incorporate an amino acid into a growing polypeptide chain (protein). Components of a translation system can include, e.g., ribosomes, tRNAs, synthetases, mRNA and the like. The O-tRNA and/or the O-RSs of the invention can be added to or be part of an in vitro or in vivo translation system, e.g., in a non-eukaryotic cell, e.g., a eubacteria (such as E. coli), or in a eukaryotic cell, e.g., a yeast cell, a mammalian cell, a plant cell, an algae cell, a fungus cell, an insect cell, and/or the like.

Unnatural amino acid: As used herein, the term "unnatural amino acid" refers to any amino acid, modified amino acid, and/or amino acid analogue, that is not one of the 20 common naturally occurring amino acids or seleno cysteine or pyrrolysine. For example, the unnatural amino acids p-benzoyl-L-phenylalanine (Bpa), para-acetyl-L-phenylalanine (pAcPhe), para-azido-L-phenylalanine (pAzPhe) and para-iodo-L-phenylalanine (pIPhe) find use with the invention.

In response to: As used herein, the term "in response to" refers to the process in which an O-tRNA of the invention recognizes a selector codon and mediates the incorporation of the unnatural amino acid, which is coupled to the tRNA, into the growing polypeptide chain.

Polypeptide: A polypeptide is any oligomer of amino acids (natural or unnatural, or a combination thereof), of any length, typically but not exclusively joined by covalent peptide bonds. A polypeptide can be from any source, e.g., a naturally occurring polypeptide, a polypeptide produced by recombinant molecular genetic techniques, a polypeptide from a cell or translation system, or a polypeptide produced by cell-free synthetic means. A polypeptide is characterized by its amino acid sequence, e.g., the primary structure of its component amino acids. As used herein, the amino acid sequence of a polypeptide is not limited to full-length sequences, but can be partial or complete sequences. Furthermore, it is not intended that a polypeptide be limited by possessing or not possessing any particular biological activity. As used herein, the term "protein" is synonymous with polypeptide. The term "peptide" refers to a small polypeptide, for example but not limited to, from 2-25 amino acids in length.

Conservative variant: As used herein, the term "conservative variant," in the context of a translation component, refers to a translation component, e.g., a conservative variant O-tRNA or a conservative variant O-RS, that functionally performs similar to a base component that the conservative variant is similar to, e.g., an O-tRNA or O-RS, having variations in the sequence as compared to a reference O-tRNA or O-RS. For example, an O-RS, or a conservative variant of that O-RS, will aminoacylate a cognate O-tRNA with an unnatural amino acid, e.g., an amino acid comprising an N-acetylgalactosamine moiety. In this example, the O-RS and the conservative variant O-RS do not have the same amino acid sequences. The conservative variant can have, e.g., one variation, two variations, three variations, four variations, or five or more variations in sequence, as long as the conservative variant is still complementary to the corresponding O-tRNA or O-RS.

In some embodiments, a conservative variant O-RS comprises one or more conservative amino acid substitutions compared to the O-RS from which it was derived. In some embodiments, a conservative variant O-RS comprises one or more conservative amino acid substitutions compared to the O-RS from which it was derived, and furthermore, retains O-RS biological activity; for example, a conservative variant O-RS that retains at least 10% of the biological activity of the parent O-RS molecule from which it was derived, or alternatively, at least 20%, at least 30%, or at least 40%. In some preferred embodiments, the conservative variant O-RS retains at least 50% of the biological activity of the parent O-RS molecule from which it was derived. The conservative amino acid substitutions of a conservative variant O-RS can occur in any domain of the O-RS, including the amino acid binding pocket.

Polynucleotide or nucleic acid: The terms "nucleic acid," "nucleic acid sequence," "nucleotide sequence," "oligonucleotide," "polynucleotide" or "nucleic acid molecule" or similar terms as used herein refer to oligomers of bases typically linked by a sugar-phosphate backbone, such as oligonucleotides or polynucleotides, and fragments or portions thereof, and to DNA or RNA of genomic or synthetic origin which can be single- or double-stranded, and represent a sense or antisense strand. The terms nucleic acid, polynucleotide and nucleotide also specifically include nucleic acids composed of bases other than the five biologically occurring bases (i.e., adenine, guanine, thymine, cytosine and uracil), and also include nucleic acids having non-natural backbone structures, such as PNA molecules.

Nucleic acid molecules (e.g., DNA or RNA) are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Thus, a polynucleotide will typically have one "5' end" comprising a 5' phosphate and one "3' end" comprising a 3' oxygen. A polynucleotide sequence, even if internal to a larger nucleic acid, also can be said to have 5' and 3' directionality. In either a linear or circular DNA molecule, discrete elements are referred to as being "upstream" or 5' of the "downstream" or 3' elements. This terminology reflects the fact that transcription proceeds in a 5' to 3' fashion along the DNA strand.

Gene: As used herein, the term "gene" most generally refers to a combination of polynucleotide elements, that when operatively linked in either a native or recombinant manner, provide some product or function. The term "gene" is to be interpreted broadly herein, encompassing mRNA, cDNA, cRNA and genomic DNA forms of a gene. In some cases, a gene is heritable. In some aspects, genes comprise coding sequences (e.g., an "open reading frame" or "coding region") necessary for the production of a polypeptide, while in other aspects, genes do not encode a polypeptide. Examples of genes that do not encode polypeptides include ribosomal RNA genes (rRNA) and transfer RNA (tRNA) genes.

The term "gene" can optionally encompass non-coding regulatory sequences that reside at a genetic locus. For example, in addition to a coding region of a nucleic acid, the term "gene" also encompasses the transcribed nucleotide sequences of the full-length mRNA adjacent to the 5' and 3' ends of the coding region. These noncoding regions are variable in size, and typically extend on both the 5' and 3' ends of the coding region. The sequences that are located 5' and 3' of the coding region and are contained on the mRNA are referred to as 5' and 3' untranslated sequences (5' UT and 3' UT). Both the 5' and 3' UT may serve regulatory roles, including translation initiation, post-transcriptional cleavage and polyadenylation. The term "gene" encompasses mRNA, cDNA and genomic forms of a gene.

In some aspects, the genomic form or genomic clone of a gene includes the sequences of the transcribed mRNA, as well as other non-transcribed sequences which lie outside of the transcript. The regulatory regions which lie outside the mRNA transcription unit are sometimes called "5' or 3' flanking sequences." A functional genomic form of a gene typically contains regulatory elements necessary for the regulation of transcription. For example, the term "promoter" is usually used to describe a DNA region, typically but not exclusively 5' of the site of transcription initiation, sufficient to confer accurate transcription initiation. In some embodiments, a promoter is constitutively active, while in alternative embodiments, the promoter is conditionally active (e.g., where transcription is initiated only under certain physiological conditions). In prokaryotes, the activity of a promoter can be modulated by an adjacent "operator" sequence. In some embodiments, the 3' flanking region contains additional sequences which regulate transcription termination, sometimes caller "terminator" sequences. Generally, the term "regulatory element" refers to any genetic element that controls some aspect of the expression of nucleic acid sequences.

Expressible nucleotide sequence: As used herein, the term "expressible nucleotide sequence" refers to any nucleotide sequence that is capable of being transcribed (for example, transcribed by a DNA-dependent RNA polymerase) to generate a transcript. The sequence of the transcript is not limited, and can be protein-coding (for example, can encode an aminoacyl-tRNA synthetase) or can be non-protein coding (for example, can encode a tRNA molecule).

Operatively linked: As used herein, the terms "in operable combination," "in operable order," "operatively linked," "operatively joined" and similar phrases, when used in reference to nucleic acids, refer to the linkage of nucleic acid sequences placed in functional relationships with each other. For example, an operatively linked promoter sequence, open reading frame and terminator sequence results in the accurate production of an RNA molecule. In some aspects, operatively linked nucleic acid elements result in the transcription of an open reading frame and ultimately the production of a polypeptide (i.e., expression of the open reading frame).

Operon: As used herein, the term "operon" refers to a genetic unit (e.g., a chromosomal region) that controls gene expression in prokaryotes. An operon typically comprises one or more genes that encode one or more polypeptide(s) or RNA(s) and the adjacent regulatory region (or regions) that controls the transcription of the genes. The regulatory region typically comprises a promoter and an operator. The coding region of a prokaryotic gene is historically termed a "cistron." Operons that contain multiple cistrons are termed "polycistronic." The genes in a polycistronic operon are typically related in function and are typically co-transcribed as a single unit and expressed in a coordinated manner.

Construct: As used herein, the term "construct" is used in reference to any polynucleotide or other molecule that can transfer nucleic acid segment(s) into a cell. The term "vector" or "vehicle" is sometimes used interchangeably with "vector." A vector optionally comprises parts which mediate vector propagation and manipulation (e.g., sequences necessary for replication, genes imparting drug or antibiotic resistance, a multiple cloning site, operably linked promoter/enhancer elements which enable the expression of a cloned gene, etc.). Vectors are often derived from plasmids, bacteriophages, or plant or animal viruses. A "cloning vector" or "shuttle vector" or "subcloning vector" contains operably linked parts that facilitate subcloning steps (e.g., a multiple cloning site containing multiple restriction endonuclease sites).

Expression vector: The term "expression vector" as used herein refers to a recombinant vector comprising operably linked polynucleotide sequences that facilitate expression of a coding sequence in a particular host organism (e.g., a bacterial expression vector). Polynucleotide sequences that facilitate expression in prokaryotes typically include, e.g., a promoter, transcription termination sequences, i.e., terminator sequences, an operator (optional), and a ribosome binding site, often along with other sequences.

Encode: As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In some aspects, the term "encode" describes the process of semiconservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

Heterologous: As used herein, the terms "heterologous" or "exogenous" as applied to polynucleotides or polypeptides refers to molecules that have been rearranged or artificially supplied to a biological system and are not in a native configuration (e.g., with respect to sequence, genomic position or arrangement of parts) or are not native to that particular biological system. The terms indicate that the relevant material originated from a source other than the naturally occurring source, or refers to molecules having a non-natural configuration, genetic location or arrangement of parts. The terms "exogenous" and "heterologous" are sometimes used interchangeably with "recombinant."

Recombinant: The term "recombinant" in reference to a nucleic acid or polypeptide indicates that the material (e.g., a recombinant nucleic acid, gene, polynucleotide, polypeptide, etc.) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates. A gene sequence open reading frame is recombinant if that nucleotide sequence has been removed from it natural context and cloned into any type of artificial nucleic acid vector. The term recombinant can also refer to an organism that harbors recombinant material. Protocols and reagents to produce recombinant molecules, especially recombinant nucleic acids, are common and routine in the art (see, e.g., Maniatis et al. (eds.), Molecular Cloning: A Laboratory Manual, Cold Spring Harbor Laboratory Press, NY, [1982]; Sambrook et al. (eds.), Molecular Cloning: A Laboratory Manual, Second Edition, Volumes 1-3, Cold Spring Harbor Laboratory Press, NY, [1989]; and Ausubel et al. (eds.), Current Protocols in Molecular Biology, Vol. 1-4, John Wiley & Sons, Inc., New York [1994]).

Native or endogenous: In contrast to a heterologous or exogenous molecule, a "native" or "endogenous" molecule is native to the biological system, species or chromosome under study. A "native" or "endogenous" gene is a gene that does not contain nucleic acid elements encoded by sources other than the chromosome on which it is normally found in nature. An endogenous gene, transcript or polypeptide is encoded by its natural chromosomal locus, and not artificially supplied to the cell.

Host cell: The term "host cell" typically refers to a cell that contains a heterologous nucleic acid, such as a vector, and supports the replication and/or expression of the nucleic acid. Host cells may be prokaryotic cells such as *E. coli*, or eukaryotic cells such as yeast, insect, amphibian or mammalian cells. Preferably, host cells are plant cells. In the context of the invention, one particularly preferred host cell is a soybean host cell.

Eukaryote: As used herein, the term "eukaryote" refers to organisms belonging to the Kingdom Eucarya. Eukaryotes are generally distinguishable from prokaryotes by their typically multicellular organization (but not exclusively multicellular, for example, yeast), the presence of a membrane-bound nucleus and other membrane-bound organelles, linear genetic material (i.e., linear chromosomes), the absence of operons, the presence of introns, message capping and poly-A mRNA, and other biochemical characteristics, such as a distinguishing ribosomal structure. Eukaryotic organisms include, for example, animals (e.g., mammals, insects, reptiles, birds, etc.), ciliates, plants (e.g., monocots, dicots, algae, etc.), fungi, yeasts, flagellates, microsporidia, protists, etc.

Prokaryote: As used herein, the term "prokaryote" refers to organisms belonging to the Kingdom Monera (also termed Procarya). Prokaryotic organisms are generally distinguishable from eukaryotes by their unicellular organization, asexual reproduction by budding or fission, the lack of a membrane-bound nucleus or other membrane-bound organelles, a circular chromosome, the presence of operons, the absence of introns, message capping and poly-A mRNA, and other biochemical characteristics, such as a distinguishing ribosomal structure. The Prokarya include subkingdoms Eubacteria and Archaea (sometimes termed "Archaebacteria"). Cyanobacteria (the blue green algae) and mycoplasma are sometimes given separate classifications under the Kingdom Monera.

Bacteria: As used herein, the terms "bacteria" and "eubacteria" refer to prokaryotic organisms that are distinguishable from Archaea. Similarly, Archaea refers to prokaryotes that are distinguishable from eubacteria. Eubacteria and Archaea can be distinguished by a number morphological and biochemical criteria. For example, differences in ribosomal RNA sequences, RNA polymerase structure, the presence or absence of introns, antibiotic sensitivity, the presence or absence of cell wall peptidoglycans adn other cell wall components, the branched versus unbranched structures of membrane lipids, and the presence/absence of histones and histone-like proteins are used to assign an organism to Eubacteria or Archaea.

Examples of Eubacteria include *Escherichia coli, Thermus thermophilus* and *Bacillus stearothermophilus*. Example of Archaea include *Methanococcus jannaschii* (Mj), *Methanosarcina mazei* (Mm), *Methanobacterium thermoautotrophicum* (Mt), *Methanococcus maripaludis, Methanopyrus kandleri, Halobacterium* such as *Haloferax volcanii* and *Halobacterium* species NRC-1, *Archaeoglobus fulgidus* (Af), *Pyrococcus furiosus* (Pf), *Pyrococcus horikoshii* (Ph), *Pyrobaculum aerophilum, Pyrococcus abyssi, Sulfolobus solfataricus* (Ss), *Sulfolobus tokodaii, Aeuropyrum pernix* (Ap), *Thermoplasma acidophilum* and *Thermoplasma volcanium*.

Derived from: As used herein, the term "derived from" refers to a component that is isolated from or made using a specified molecule or organism, or information from the specified molecule or organism. For example, a polypeptide that is derived from a second polypeptide can include an amino acid sequence that is identical or substantially similar to the amino acid sequence of the second polypeptide. In the case of polypeptides, the derived species can be obtained by, for example, naturally occurring mutagenesis, artificial directed mutagenesis or artificial random mutagenesis. The mutagenesis used to derive polypeptides can be intentionally directed or intentionally random, or a mixture of each. The mutagenesis of a polypeptide to create a different polypeptide derived from the first can be a random event (e.g., caused by polymerase infidelity) and the identification of the derived polypeptide can be made by appropriate screening methods, e.g., as discussed herein. Mutagenesis of a polypeptide typically entails manipulation of the polynucleotide that encodes the polypeptide.

Similarly, the term "derived from" can apply to polynucleotides. A polypeptide that is derived from a source polynucleotide can include a nucleotide sequence that is identical or substantially similar to the source nucleotide sequence. In the case of polynucleotides, the derived species can be obtained by, for example, naturally occurring mutagenesis, artificial directed mutagenesis or artificial random mutagenesis. The mutagenesis used to derive polynucleotides can be intentionally directed or intentionally random, or a mixture of each. In some aspects, a derived polynucleotide is generated by placing a source polynucleotide into a heterologous context, i.e., into a context that is different from its native or endogenous context. For example, a gene promoter can be derived from an endogenous gene promoter by removing that endogenous promoter domain and placing it in operable combination with different nucleotide sequences with which it is not normally associated.

Positive selection or screening marker: As used herein, the term "positive selection or screening marker" refers to a marker that, when present, e.g., expressed, activated or the like, results in identification of a cell, which comprises the trait, e.g., a cell with the positive selection marker, from those without the trait.

Negative selection or screening marker: As used herein, the term "negative selection or screening marker" refers to a marker that, when present, e.g., expressed, activated, or the like, allows identification of a cell that does not comprise a selected property or trait (e.g., as compared to a cell that does possess the property or trait).

Selection or screening agent: As used herein, the term "selection or screening agent" refers to an agent that, when present, allows for selection/screening of certain components from a population. For example, a selection or screening agent can be, but is not limited to, e.g., a nutrient, an antibiotic, a wavelength of light, an antibody, an expressed polynucleotide, or the like. The selection agent can be varied, e.g., by concentration, intensity, etc.

Reporter: As used herein, the term "reporter" or equivalent terms refers in a general sense to any component that can be readily detected in a system under study, where the detection of the reporter correlates with the presence or absence of some other molecule or property, or can be used to identify, select and/or screen targets in a system of interest. The choice of the most suitable reporter to use for a particular application depends on the intended use, and other variables known to one familiar with the art. In some aspects, a reporter is a reporter gene.

A wide variety of reporter molecules and genes are known in the art. Each reporter has a particular assay for the detection of that reporter. Some reporter detection assays can be enzymatic assays, while other assays can be immunological in nature (e.g., ELISA or immunohistochemical analysis), or colorimetric, for example. Further still, a reporter can include a protein, e.g., an enzyme, that confers antibiotic resistance or sensitivity (e.g., β-lactamase, chloramphenicol acetyltransferase (CAT), and the like), a fluorescent marker (e.g., a green fluorescent protein such as GFP, YFP, EGFP, RFP, etc.), a luminescent marker (e.g., a firefly luciferase protein), an affinity based screening marker, an enzymatic activity such as lacZ (β-galactosidase), or other positive or negative selectable marker genes such as ADH (alcohol dehydrogenase), his3, ura3, leu2, lys2, or the like.

BRIEF DESCRIPTION OF THE FIGURES

FIG. 8 provides various polynucleotide and polypeptide sequences that find use with the invention.

DETAILED DESCRIPTION OF THE INVENTION

Figure 1:
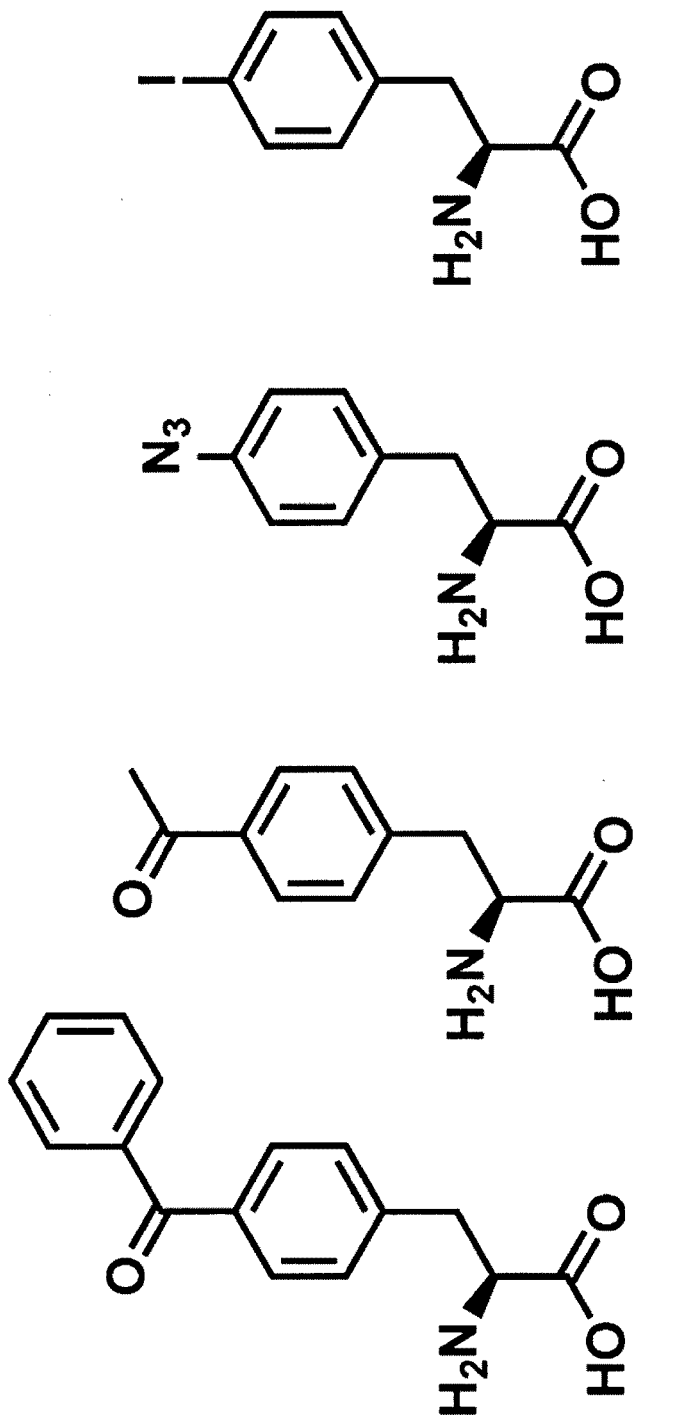
FIG. 1 provides the structures and corresponding names of four unnatural amino acids, which are p-benzoyl-L-phenylalanine (Bpa), para-acetyl-L-phenylalanine (pAcPhe), para-azido-L-phenylalanine (pAzPhe) and para-iodo-L-phenylalanine (pIPhe).

The invention provides improved expression vector systems useful for the efficient bacterial expression of mutant proteins comprising one or more unnatural amino acid at specific sites genetically coded by selector codons (e.g., amber nonsense codons). These systems utilize orthogonal translation technology known in the art for the in vivo incorporation of the unnatural amino acids. The invention is not limited in any aspect with regard to the particular orthogonal translation components that are used (i.e., the particular orthogonal aminoacyl-tRNA synthetase or the particular orthogonal suppressor tRNA). Furthermore, in some embodiments, the invention provides improved compositions and methods that find broad use in bacterial expression vector systems that are not limited to the expression of orthogonal aminoacyl-tRNA synthetases or suppressor tRNAs.

The invention provides novel expression vector features that result in significantly improved efficiency in the incorporation of unnatural amino acids into proteins in eubacteria (e.g., *E. coli*), and result in high-yield expression of mutant proteins containing the unnatural amino acids at specific sites genetically designated by selector codons. The improved efficiency in the incorporation of unnatural amino acids into a protein of interest is presumably due (at least in part) to the improved expression of the orthogonal aminoacyl-tRNA synthetase and suppressor tRNA, although an understanding of the mechanism of the improved efficiency is not required to made or use the invention.

The novel expression vector features of the invention are broadly compatible with a variety of E. coli expression vector backbones and E. coli strains, and are also readily adapted for the expression of other proteins or tRNAs of interest, in addition to the expression of orthogonal aminoacyl-tRNA synthetases or orthogonal suppressor tRNAs.

In some aspects, the novel expression vector features provided by the invention are used independently on separate plasmids. In other aspects, a single novel feature or combination of features are used in a plurality of plasmids. In still other embodiments, a plurality of these features are used in combination on the same plasmid. The invention provides a number of improvements to bacterial expression vector systems that can be used to improve expression of mutant proteins comprising one or more unnatural amino acid, and in some cases, can be used more broadly to improve expression of any particular polypeptide or tRNA of interest.

The invention provides, for example, the following improvements to bacterial expression vector systems:

(A) The invention provides expression vectors where the orthogonal aminoacyl-tRNA synthetase gene and orthogonal suppressor tRNA gene are carried on the same plasmid. This simplifies the expression of these orthogonal components, where previously, these two components were each carried on separate plasmids;

(B) The invention provides improved promoter and terminator sequences derived from E. coli proline tRNA operons to expresses a heterologous tRNA sequence, e.g., an orthogonal MjtRNA-Tyr(CUA) gene or any other orthogonal tRNA gene. The E. coli proline tRNA gene used to derive the promoter and terminator sequences can be the E. coli proK, proL or proM tRNA genes.

(C) The invention provides improved recombinant polycistronic operons for the expression of tRNA genes, where any two tRNA genes in the operon are separated by a heterologous linker sequence derived from a linker of a naturally occurring tRNA polycistronic operon, for example, the linker that occurs naturally between the E. coli valU and valX genes, or alternately, e.g., between the ileT and alaT genes.

(D) The invention provides a novel promoter sequence derived from the E. coli glnS promoter for the improved expression of an open reading frame, e.g., an open reading frame encoding an orthogonal aminoacyl-tRNA synthetase.

Vector Systems for Coexpression of O-tRNA and O-RS Genes

In some aspects, the invention provides expression vectors where the orthogonal aminoacyl-tRNA synthetase gene and orthogonal suppressor tRNA gene are carried on the same plasmid. This feature is an improvement over the art, where previously it was necessary to co-transform a host cell with two separate expression vectors that independently carried the O-tRNA and the O-RS genes.

As described in the Examples, a series of related expression vectors are constructed that are suitable for the co-expression of O-tRNA and O-RS species. These plasmids include:

pYR-BpaRS1
pYR-BpaRS5
pYR-BpaRS5(D286R)
pYR-BpaRS-TRN
pYR-BpaRS-TRN(D286R)
pYR-BpaRS-3TRN(D286R)
pYR-BpaRS-6TRN(D286R)
pSup-BpaRS-6TRN(D286R)
pSup-pAcPheRS-6TRN
pSup-pAzPheRS-6TRN
pSup-pIPheRS-6TRN

Each of these plasmids is a feature of the invention. However, it is not intended that the invention be limited to these plasmids, as one of skill will recognize that construction of variants of these plasmids are well within the scope of the invention.

For example, it is not intended that any plasmid of the invention be limited to the expression any particular O-tRNA or O-RS species to produce a protein comprising any particular unnatural amino acid. The Examples provided herein describe the successful use of a MjtRNA-Tyr(CUA) (SEQ ID NO: 1) and four different O-RS species that have tRNA charging specificity for p-benzoyl-L-phenylalanine (Bpa), para-acetyl-L-phenylalanine (pAcPhe), para-azido-L-phenylalanine (pAzPhe) and para-iodo-L-phenylalanine (pIPhe) (see FIG. 1, and FIG. 8, SEQ ID NOS: 4, 6, 8 and 10).

These working examples above serve to illustrate the broader applicability of the invention to be used with other O-tRNA and O-RS species. Indeed, the invention finds use in the expression of any O-tRNA or any O-RS of interest, and in particular, orthogonal translation components that optimally operate in eubacterial cells. In some aspects, the invention finds particular use with O-RS species that are derived from naturally occurring Archaea (e.g., *Methanococcus jannaschii*) aminoacyl-tRNA synthetases or O-tRNA species derived from Archaea tRNA. The wide variety of O-tRNA and O-RS species that find use with the invention are known in the art and are described in numerous sources. See, for example, International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; WO 2005/007624, filed Jul. 7, 2004 and WO 2006/110182, filed Oct. 27, 2005, entitled "ORTHOGONAL TRANSLATION COMPONENTS FOR THE IN VIVO INCORPORATION OF UNNATURAL AMINO ACIDS." Each of these applications is incorporated herein by reference in its entirety. For further discussion of orthogonal translation systems that incorporate unnatural amino acids, and methods for their production and use, see also, Wang and Schultz "Expanding the Genetic Code," *Angewandte Chemie Int. Ed.*, 44(1):34-66 (2005), Xie and Schultz, "An Expanding Genetic Code," *Methods* 36(3):227-238 (2005); Xie and Schultz, "Adding Amino Acids to the Genetic Repertoire," *Curr. Opinion in Chemical Biology* 9(6):548-554; and Wang et al., "Expanding the Genetic Code," *Annu. Rev. Biophys. Biomol. Struct.*, epub Jan. 13, 2006; the contents of which are each incorporated by reference in their entirety.

The prior art (e.g., the art cited herein) also provides guidance for the construction and use of numerous variants (e.g., conservative variants) and fragments of known O-RS and O-tRNA species. These variants and fragments also find use with the expression vectors of the invention. The art also provides guidance for the identification and construction of new O-RS and O-tRNA species, which also find use with the invention.

Plasmid Constructions and Eubacterial Host Cells

As described and used in Example 6, the plasmids provided in the specification are based on a pACYC184 vector backbone. However, it is not intended that plasmids of the invention be limited to the use of that particular backbone vector. One of skill in the art recognizes that any one of a variety of plasmids (including other publicly or commercially available plasmids) can be used to construct the plasmids of the invention. For example, the plasmids pACYC177 and pRARE2 vector (Novagen; see inNovations, No. 12, June 2001) can also be used in conjunction with the invention. In some aspects, any plasmid carrying a compatible origin of replication (e.g., the p15A origin of replication) and at least one selection marker can be used in conjunction with the invention. Derivatives of the plasmid pSC101 can also be used with the invention.

Also as described in Example 6, the plasmids provided by the invention were used to transform One Shot® TOP-10 electrocompetent E. coli (Invitrogen™). However, it is not intended that the eubacterial strain used as a host cell to produce proteins comprising one or more unnatural amino acids be limited to the use of that particular host cell. One of skill in the art recognizes that any one of a variety of host cells (including other commercially available plasmids as ell as strains produced by the user) can be readily used to produce proteins comprising unnatural amino acids. For example, other host cells such as E. coli strain DH10B™ (Invitrogen™), Electrocomp™ GeneHogs® (Invitrogen™), BL21 One Shot® (Invitrogen™), and BL21(DE3) One Shot® (Invitrogen™). Indeed, any E. coli strains without any endogenous tRAN suppressor gene is a suitable host cell. Other species of eubacteria in addition to E. coli also find use with the invention. For example, it is contemplated that strains of Bacillus subtilus can also be used as host cells for the vectors of the invention.

Improved Promoter and Terminator Sequences for Expression of O-tRNA

In order to improve the suppression efficiency of the orthogonal translation system, a new amber suppressor tRNA operon with a naturally occurring E. coli tRNA promoter and terminator was constructed. A survey of E. coli tRNA genes revealed that E. coli proline tRNAs have the same C1-G72 pair as Archaea tRNAs; this base pair is a major identity determinant for the selective recognition of MjtRNA-Tyr (CUA) by MjTyrRS in E. coli (Wang and Schultz, Chem. Biol., 8:883-890 (2001)).

In view of this observation, a synthetic amber suppressor tRNA gene was constructed such that a heterologous O-tRNA gene replaces the same length (77-nucleotide) E. coli proK gene in the monocistronic proK operon. An improved expression vector (pYR-BpaRS5) was generated by substituting the original suppressor tRNA operon in pYR-BpaRS1 with the MjtRNA-Tyr(CUA) gene under control of the proK promoter (SEQ ID NO: 32) and proK terminator (SEQ ID NO: 33). This expression construct showed a 2-fold increase in the expression of the O-tRNA (see FIG. 3), and resulted in significantly improved suppression efficiency (see FIG. 2), both relative to the activities of the pYR-BpaRS1 vector.

Thus, the invention provides improved expression vectors for the expression of a tRNA of interest, where the expression of a polycistronic tRNA is driven by promoter and terminator nucleotide sequences derived from the E. coli proline tRNA gene proK.

As described in Example 1, the particular tRNA used to demonstrate this improved expression vector was an orthogonal tRNA (O-tRNA), more specifically, MjtRNA-Tyr(CUA). However, it is not intended that the improved efficiency of tRNA expression be limited to MjtRNA-Tyr(CUA), nor limited to an O-tRNA. Indeed, this feature of the invention can be used to improve the expression of any tRNA of interest.

In E. coli, three species of tRNA are charged with proline during translation. In addition to the proK tRNA gene, E. coli also uses two additional prolyl-tRNA genes. These are proL and proM. In view of their similar structure to the proK locus, it is contemplated that the promoter sequence of proL (SEQ ID NO: 34) and the terminator sequences of proL and proM (SEQ ID NOS: 35 and 36, respectively) also find use in the construction of improved expression vectors of the invention. It is also a feature of the invention that combinations of promoters and terminators from different E. coli prolyl-tRNA genes can also be used to achieve improved expression. For example, the promoter sequence of proK (SEQ ID NO: 32) can be used in conjunction with the terminator sequence of proL (SEQ ID NO: 35).

Improved Polycistronic Operon Structures

The invention provides improved recombinant polycistronic operons for the expression of tRNA genes. These polycistronic operons comprise multiple copies (e.g., three copies) of tRNA genes of interest, where the tRNA sequences are separated by a heterologous linker sequence derived from a linker of a naturally occurring tRNA polycistronic operon, for example, the linker that occurs naturally between the E. coli valU and valX genes (SEQ ID NO: 14), or alternatively, e.g., between the E. coli ileT and alaT tRNA genes (SEQ ID NO: 15).

Thus, the invention provides improved expression vectors for the expression of polycistronic tRNA operons, where the operon comprises at least one heterologous tRNA linker that separates at least two expressed tRNA sequences. In some embodiments, as described in Example 3, multiple tRNA linkers are used to separate three or more expressed tRNA sequences in the operon. In that case, the tRNA linker used between each expressed tRNA pair can be different (as in Example 3), or can be the same linker between each tRNA gene.

It is not intended that the invention be limited to the use of the E. coli valU and valX gene linker (SEQ ID NO: 14), or the E. coli ileT and alaT tRNA gene linker (SEQ ID NO: 15). Indeed, additional naturally occurring tRNA linkers also find use with the invention. For example, each of the following linkers located between the native E. coli tRNA genes listed below finds use with the invention, where the linker that is used in the recombinant system is heterologous to whatever expressed tRNA sequences are in the recombinant operon. These useful tRNA linkers include:

| Native E. coli tRNA linker | Sequence | SEQ ID NO: |
|---|---|---|
| valU and valX | ACTACTTTATGTAGTCTCCGCCGTGTAGCAAGAAATTGAGAAGT | 14 |
| ileT and alaT | AATTTGCACGGCAAATTTGAAGAGGTTTTAACTACATGTTAT | 15 |
| serV and argV | TTT | 16 |
| valV and valW | TCCT | 17 |
| glyT and thrT | AGATGT | 18 |
| metT and leuW | TCTTTTTTT | 19 |
| glnW and metU | TCGAAGAAACAATCT | 20 |

-continued

| Native E. coli tRNA linker | Sequence | SEQ ID NO: |
|---|---|---|
| hisR and leuT | TTATTAGAAGTTGTGACAAT | 21 |
| glnU and glnW | TCTTCTTCGAGTAAGCGGTTCACCGCCCGGTTAT | 22 |
| leuP and leuV | AACGAGGCGATATCAAAAAAAGTAAGATGACTGT | 23 |
| glnV and glnX | ATTTATTCAAGACGCTTACCTTGTAAGTGCACCC AGT | 24 |
| alaW and alaX | AATTTTGCACCCAGCAAACTTGGTACGTAAACGC ATCGT | 25 |
| ileU and alaU | AATTTGCACGGCAAATTTGAAGAGGTTTTAACTA CATGTTAT | 26 |
| ileV and alaV | AATTTGCACGGCAAATTTGAAGAGGTTTTAACTA CATGTTAT | 27 |
| metU and glnV | AATTCTGAATGTATCGAATATGTTCGGCAAATTC AAAACCAATTTGT | 28 |
| glyW and cysT | GTTTAAAAGACATCGGCGTCAAGCGGATGTCTGG CTCAAAGGCCTGAAGAATTT | 29 |
| argX and hisR | TTTAGTCCCGGCGCTTGAGCTGCGGTGGTAGTAA TACCGCGTAACAAGATTTGTAGT | 30 |
| argY and argZ | TCTCTTACTTGATATGGCTTTAGTAGCGGTATCA ATATCAGCAGTAAAATAAATTTCCCGAT | 31 |

In some embodiments, preferred tRNA linkers that find use with the invention contain either or both T(−1) and A(77) nucleotides. These two nucleotide positions in tRNA linkers have been shown to be optimal for efficient 5' and 3'-processing of tRNA precursors when in their native (i.e., endogenous) context. See, for example, Li and Deutscher, "Maturation pathways for *E. coli* tRNA precursors: A random multienzyme process in vivo," *Cell* 86:503-512 (1996); and Zahler et al., "Recognition of the 5' leader of pre-tRNA substrates by the active site of ribonuclease P," *RNA* 9:734-745 (2003). In other embodiments, the tRNA linkers finding use with the invention comprise restriction sites (naturally occurring or engineered).

In some embodiments, the invention provides constructs that comprise a plurality of the same polycistronic operon, optionally in tandem. Thus, if a single polycistronic operon comprises three copies of an expressible nucleotide sequence (such as a tRNA gene), then two of the operons will result in a total of six tRNA gene sequences being expressed. This type of gene cluster configuration is demonstrated in Example 3 and FIG. 5.

The improved recombinant polycistronic operon described in Example 3 expresses the orthogonal tRNA MjtRNA-Tyr (CUA). However, it is not intended that the invention be limited to the expression of MjtRNA-Tyr(CUA). Nor is the invention limited to the expression of orthogonal tRNA species. Indeed, the improved polycistronic operons of the invention can be used to express any desired tRNA species.

An Improved *E. coli* glnS Promoter for Polypeptide Expression

The invention provides a novel promoter sequence derived from the *E. coli* glnS promoter for the improved expression of an open reading frame. As described in Example 2, mutant glnS promoter (SEQ ID NO: 12) described in Plumbridge and Söll (*Biochimie* 69:539-541 (1987)) was subcloned into an expression vector of the invention. Sequencing of the subcloned glnS promoter region revealed the inadvertent introduction of a deletion to the promoter sequence (in addition to the substitution described in Plumbridge and Söll). This further modified novel glnS promoter variant was termed glnS-TNR (provided in SEQ ID NO: 13). Surprisingly, this mutation resulted in an improvement in the translational efficiency of the system compared to the wild-type glnS promoter activity as determined by Western blotting (see FIG. 4).

As described in Examples 2 and 5, the glnS-TNR promoter was used to express the orthogonal synthetases BpaRS, pAcPheRS, pAzPheRS and pIPheRS. However, it is not intended that the invention be limited to the expression of any particular orthogonal aminoacyl-tRNA synthetase, or limited to any aminoacyl-tRNA synthetase in general. This improved promoter find broad use in the bacterial expression of any desired polypeptide open reading frame.

Orthogonal tRNA/Aminoacyl-tRNA Synthetase Technology

An understanding of the novel compositions and methods of the present invention is facilitated by an understanding of the activities associated with orthogonal tRNA and orthogonal aminoacyl-tRNA synthetase pairs. In order to add additional unnatural amino acids to the genetic code, new orthogonal pairs comprising an aminoacyl-tRNA synthetase and a suitable tRNA are needed that can function efficiently in the host translational machinery, but that are "orthogonal" to the translation system at issue, meaning that it functions independently of the synthetases and tRNAs endogenous to the translation system. Desired characteristics of the orthologous pair include tRNA that decode or recognize only a specific codon, e.g., a selector codon, that is not decoded by any endogenous tRNA, and aminoacyl-tRNA synthetases that preferentially aminoacylate (or "charge") its cognate tRNA with only one specific unnatural amino acid. The O-tRNA is also not typically aminoacylated by endogenous synthetases. For example, in *E. coli*, an orthogonal pair will include an aminoacyl-tRNA synthetase that does not cross-react with any of the endogenous tRNA, e.g., which there are 40 in *E. coli*, and an orthogonal tRNA that is not aminoacylated by any of the endogenous synthetases, e.g., of which there are 21 in *E. coli*. To date, a wide variety of structurally diverse unnatural amino acids have been incorporated into proteins using orthogonal translation technology, as known in the art.

The ability to incorporate an unnatural amino acid site-specifically into a polypeptide can facilitate the study of proteins by enabling the highly selective post-translational modification of those proteins, as well as enable the engineering of proteins with novel properties. For example, expression of proteins containing one or more unnatural amino acids can facilitate the study of proteins by specific labeling, alter catalytic function of enzymes, improve biological activity or reduce cross-reactivity to a substrate, crosslink a protein with other proteins, small molecules or biomolecules, reduce or eliminate protein degradation, improve half-life of proteins in vivo (e.g., by pegylation or other modifications of introduced reactive sites), etc.

Orthogonal translation systems that are suitable for making proteins that comprise one or more unnatural amino acid are known in the art, as are the general methods for producing orthogonal translation systems. For example, see International Publication Numbers WO 2002/086075, entitled "METHODS AND COMPOSITIONS FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; WO 2005/007624, filed Jul. 7, 2004 and WO 2006/110182, filed Oct. 27, 2005, entitled "ORTHOGONAL TRANSLATION COMPONENTS FOR THE IN VIVO INCORPORATION OF UNNATURAL AMINO ACIDS." Each of these applications is incorporated herein by reference in its entirety. For discussion of orthogonal translation systems that incorporate unnatural amino acids, and methods for their production and use, see also, Wang and Schultz "Expanding the Genetic Code," *Angewandte Chemie Int. Ed.,* 44(1):34-66 (2005), Xie and Schultz, "An Expanding Genetic Code," *Methods* 36(3): 227-238 (2005); Xie and Schultz, "Adding Amino Acids to the Genetic Repertoire," *Curr. Opinion in Chemical Biology* 9(6):548-554; Wang et al., "Expanding the Genetic Code," *Annu. Rev. Biophys. Biomol. Struct.,* 35:225-249 (2006); and Xie and Schultz, "A chemical toolkit for proteins—an expanded genetic code," *Nat. Rev. Mol. Cell Biol.,* 7(10):775-782 (2006; epub Aug. 23, 2006), the contents of which are each incorporated by reference in their entirety.

Such translation systems generally comprise cells (which can be prokaryotic cells such as *E. coli*, or eukaryotic cells such as yeast) that include an orthogonal tRNA (O-tRNA), an orthogonal aminoacyl tRNA synthetase (O-RS), and an unnatural amino acid, where the O-RS aminoacylates the O-tRNA with the unnatural amino acid. An orthogonal pair of the invention can include an O-tRNA, e.g., a suppressor tRNA, a frameshift tRNA, or the like, and a cognate O-RS.

In general, when an orthogonal pair recognizes a selector codon and loads an amino acid in response to the selector codon, the orthogonal pair is said to "suppress" the selector codon. That is, a selector codon that is not recognized by the translation system's (e.g., the cell's) endogenous machinery is not ordinarily charged, which results in blocking production of a polypeptide that would otherwise be translated from the nucleic acid. In an orthogonal pair system, the O-RS aminoacylates the O-tRNA with a specific unnatural amino acid. The charged O-tRNA recognizes the selector codon and suppresses the translational block caused by the selector codon. The cell uses the O-tRNA/O-RS pair to incorporate the unnatural amino acid into a growing polypeptide chain, e.g., via a nucleic acid that comprises a polynucleotide that encodes a polypeptide of interest, where the polynucleotide comprises a selector codon that is recognized by the O-tRNA. In certain desirable aspects, the cell can include an additional O-tRNA/O-RS pair, where the additional O-tRNA is loaded by the additional O-RS with a different unnatural amino acid. For example, one of the O-tRNAs can recognize a four base codon and the other can recognize a stop codon. Alternately, multiple different stop codons or multiple different four base codons can specifically recognize different selector codons.

In certain embodiments, systems comprise a cell such as an *E. coli* cell or a yeast cell that includes an orthogonal tRNA (O-tRNA), an orthogonal aminoacyl-tRNA synthetase (O-RS), an unnatural amino acid and a nucleic acid that comprises a polynucleotide that encodes a polypeptide of interest, where the polynucleotide comprises the selector codon that is recognized by the O-tRNA. The translation system can also be a cell-free system, e.g., any of a variety of commercially available "in vitro" transcription/translation systems in combination with an O-tRNA/ORS pair and an unnatural amino acid as described herein.

As noted, in some embodiments, there exists multiple O-tRNA/O-RS pairs in a cell or other translation system, which allows incorporation of more than one unnatural amino acid into a polypeptide. For example, the cell can further include an additional different O-tRNA/O-RS pair and a second unnatural amino acid, where this additional O-tRNA recognizes a second selector codon and this additional O-RS preferentially aminoacylates the O-tRNA with the second unnatural amino acid. For example, a cell that includes an O-tRNA/O-RS pair (where the O-tRNA recognizes, e.g., an amber selector codon), can further comprise a second orthogonal pair, where the second O-tRNA recognizes a different selector codon, e.g., an opal codon, a four-base codon, or the like. Desirably, the different orthogonal pairs are derived from different sources, which can facilitate recognition of different selector codons.

The O-tRNA and/or the O-RS can be naturally occurring or can be, e.g., derived by mutation of a naturally occurring tRNA and/or RS, e.g., by generating libraries of tRNAs and/or libraries of RSs, from any of a variety of organisms and/or by using any of a variety of available mutation strategies. For example, one strategy for producing an orthogonal tRNA/aminoacyl-tRNA synthetase pair involves importing a heterologous (to the host cell) tRNA/synthetase pair from, e.g., a source other than the host cell, or multiple sources, into the host cell. The properties of the heterologous synthetase candidate include, e.g., that it does not charge any host cell tRNA, and the properties of the heterologous tRNA candidate include, e.g., that it is not aminoacylated by any host cell synthetase. In addition, the heterologous tRNA is orthogonal to all host cell synthetases.

A second strategy for generating an orthogonal pair involves generating mutant libraries from which to screen and/or select an O-tRNA or O-RS. These strategies can also be combined.

Orthogonal tRNA (O-tRNA)

An orthogonal tRNA (O-tRNA) desirably mediates incorporation of an unnatural amino acid into a protein that is encoded by a polynucleotide that comprises a selector codon that is recognized by the O-tRNA, e.g., in vivo or in vitro, with a high suppression efficiency. Suppression efficiency can be determined by any of a number of assays known in the art. For example, a β-galactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

O-tRNAs can also be derived from conservative variations of known O-tRNAs. For example, conservative variations of O-tRNA include those molecules that function like the particular O-tRNAs, e.g., as in the sequence listing herein and that maintain the tRNA L-shaped structure by virtue of appropriate self-complementarity, but that do not have a sequence identical to those, e.g., in the sequence listing, figures or examples herein (and, desirably, are other than wild type tRNA molecules).

The composition comprising an O-tRNA can further include an orthogonal aminoacyl-tRNA synthetase (O-RS), where the O-RS preferentially aminoacylates the O-tRNA with an unnatural amino acid. In certain embodiments, a composition including an O-tRNA can further include a translation system (e.g., in vitro or in vivo). A nucleic acid that comprises a polynucleotide that encodes a polypeptide of interest, where the polynucleotide comprises a selector codon that is recognized by the O-tRNA, or a combination of one or more of these can also be present in the cell.

Methods of producing an orthogonal tRNA (O-tRNA) are known. In certain embodiments of the invention, the O-tRNAs can be produced by generating a library of mutants. The library of mutant tRNAs can be generated using various mutagenesis techniques known in the art. For example, the mutant tRNAs can be generated by site-specific mutations, random point mutations, homologous recombination, DNA shuffling or other recursive mutagenesis methods, chimeric construction or any combination thereof.

Additional mutations can be introduced at a specific position(s), e.g., at a nonconserved position, or at a conserved position, at a randomized position(s), or a combination of both in a desired loop or region of a tRNA, e.g., an anticodon loop, the acceptor stem, D arm or loop, variable loop, TPC arm or loop, other regions of the tRNA molecule, or a combination thereof. Typically, mutations in a tRNA include mutating the anticodon loop of each member of the library of mutant tRNAs to allow recognition of a selector codon. The method can further include adding additional sequences to the O-tRNA. Typically, an O-tRNA possesses an improvement of orthogonality for a desired organism compared to the starting material, e.g., the plurality of tRNA sequences, while preserving its affinity towards a desired RS.

The methods optionally include analyzing the similarity (and/or inferred homology) of sequences of tRNAs and/or aminoacyl-tRNA synthetases to determine potential candidates for an O-tRNA, O-RS and/or pairs thereof, that appear to be orthogonal for a specific organism. Computer programs known in the art and described herein can be used for the analysis, e.g., BLAST and pileup programs can be used. In one example, to choose potential orthogonal translational components for use in *E. coli*, a synthetase and/or a tRNA is chosen that does not display close sequence similarity to eubacterial organisms.

Typically, an O-tRNA is obtained by subjecting to, e.g., negative selection, a population of cells of a first species, where the cells comprise a member of the plurality of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species.

In certain embodiments, in the negative selection, a selector codon(s) is introduced into a polynucleotide that encodes a negative selection marker, e.g., an enzyme that confers antibiotic resistance, e.g., β-lactamase, an enzyme that confers a detectable product, e.g., β-galactosidase, chloramphenicol acetyltransferase (CAT), e.g., a toxic product, such as barnase, at a nonessential position (e.g., still producing a functional barnase), etc. Screening/selection is optionally done by growing the population of cells in the presence of a selective agent (e.g., an antibiotic, such as ampicillin). In one embodiment, the concentration of the selection agent is varied.

For example, to measure the activity of suppressor tRNAs, a selection system is used that is based on the in vivo suppression of selector codon, e.g., nonsense (e.g., stop) or frameshift mutations introduced into a polynucleotide that encodes a negative selection marker, e.g., a gene for β-lactamase (bla). For example, polynucleotide variants, e.g., bla variants, with a selector codon at a certain position (e.g., A184), are constructed. Cells, e.g., bacteria, are transformed with these polynucleotides. In the case of an orthogonal tRNA, which cannot be efficiently charged by endogenous *E. coli* synthetases, antibiotic resistance, e.g., ampicillin resistance, should be about or less than that for a bacteria transformed with no plasmid. If the tRNA is not orthogonal, or if a heterologous synthetase capable of charging the tRNA is co-expressed in the system, a higher level of antibiotic, e.g., ampicillin, resistance is be observed. Cells, e.g., bacteria, are chosen that are unable to grow on LB agar plates with antibiotic concentrations about equal to cells transformed with no plasmids.

In the case of a toxic product (e.g., ribonuclease or barnase), when a member of the plurality of potential tRNAs is aminoacylated by endogenous host, e.g., *Escherichia coli* synthetases (i.e., it is not orthogonal to the host, e.g., *Escherichia coli* synthetases), the selector codon is suppressed and the toxic polynucleotide product produced leads to cell death. Cells harboring orthogonal tRNAs or non-functional tRNAs survive.

In one embodiment, the pool of tRNAs that are orthogonal to a desired organism are then subjected to a positive selection in which a selector codon is placed in a positive selection marker, e.g., encoded by a drug resistance gene, such a β-lactamase gene. The positive selection is performed on a cell comprising a polynucleotide encoding or comprising a member of the pool of tRNAs that are orthogonal to the cell, a polynucleotide encoding a positive selection marker, and a polynucleotide encoding a cognate RS. In certain embodiments, the second population of cells comprises cells that were not eliminated by the negative selection. The polynucleotides are expressed in the cell and the cell is grown in the presence of a selection agent, e.g., ampicillin. tRNAs are then selected for their ability to be aminoacylated by the coexpressed cognate synthetase and to insert an amino acid in response to this selector codon. Typically, these cells show an enhancement in suppression efficiency compared to cells harboring non-functional tRNA(s), or tRNAs that cannot efficiently be recognized by the synthetase of interest. The cell harboring the non-functional tRNAs or tRNAs that are not efficiently recognized by the synthetase of interest, are sensitive to the antibiotic. Therefore, tRNAs that: (i) are not substrates for endogenous host, e.g., *Escherichia coli*, synthetases; (ii) can be aminoacylated by the synthetase of interest; and (iii) are functional in translation, survive both selections.

Accordingly, the same marker can be either a positive or negative marker, depending on the context in which it is screened. That is, the marker is a positive marker if it is screened for, but a negative marker if screened against.

The stringency of the selection, e.g., the positive selection, the negative selection or both the positive and negative selection, in the above described-methods, optionally includes varying the selection stringency. For example, because barnase is an extremely toxic protein, the stringency of the negative selection can be controlled by introducing different numbers of selector codons into the barnase gene and/or by using an inducible promoter. In another example, the concentration of the selection or screening agent is varied (e.g., ampicillin concentration). In some aspects of the invention, the stringency is varied because the desired activity can be low during early rounds. Thus, less stringent selection criteria are applied in early rounds and more stringent criteria are applied in later rounds of selection. In certain embodiments, the negative selection, the positive selection or both the negative and positive selection can be repeated multiple times. Multiple different negative selection markers, positive selection markers or both negative and positive selection markers can be used. In certain embodiments, the positive and negative selection marker can be the same.

Other types of selections/screening can be used in the invention for producing orthogonal translational components, e.g., an O-tRNA, an O-RS, and an O-tRNA/O-RS pair that loads an unnatural amino acid in response to a selector codon. For example, the negative selection marker, the positive selection marker or both the positive and negative selection markers can include a marker that fluoresces or catalyzes a luminescent reaction in the presence of a suitable reactant. In another embodiment, a product of the marker is detected by fluorescence-activated cell sorting (FACS) or by luminescence. Optionally, the marker includes an affinity based screening marker. See also, Francisco, J. A., et al., (1993) *Production and fluorescence-activated cell sorting of Escherichia coli expressing a functional antibody fragment on the external surface.* Proc Natl Acad Sci USA. 90:10444-8.

Additional methods for producing a recombinant orthogonal tRNA can be found, e.g., in International Application Publications WO 2002/086075, entitled "METHODS AND COMPOSITIONS FOR THE PRODUCTION OF ORTHOGONAL tRNA AMINOACYL-tRNA SYNTHETASE PAIRS;" WO 2004/094593, entitled "EXPANDING THE EUKARYOTIC GENETIC CODE;" and WO 2005/019415, filed Jul. 7, 2004. See also Forster et al., (2003) *Programming peptidomimetic synthetases by translating genetic codes designed de novo* PNAS 100(11):6353-6357; and, Feng et al., (2003), *Expanding tRNA recognition of a tRNA synthetase by a single amino acid change*, PNAS 100 (10): 5676-5681.

Orthogonal Aminoacyl-tRNA Synthetase (O-RS)

An O-RS finding use with the invention preferentially aminoacylates an O-tRNA with an unnatural amino acid, in vitro or in vivo. An O-RS can be provided to the translation system, e.g., a cell, by a polypeptide that includes an O-RS and/or by a polynucleotide that encodes an O-RS or a portion thereof. For example, an O-RS comprises an amino acid sequence as known in the art, or a conservative variation thereof. In another example, an O-RS, or a portion thereof, is encoded by a polynucleotide sequence that encodes an amino acid comprising sequence in the sequence listing or examples herein, or a complementary polynucleotide sequence thereof. See, e.g., FIG. 8 for sequences of useful O-RS molecules.

Methods for identifying an orthogonal aminoacyl-tRNA synthetase (O-RS), e.g., an O-RS, for use with an O-tRNA, are known. For example, a method includes subjecting to selection, e.g., positive selection, a population of cells of a first species, where the cells individually comprise: 1) a member of a plurality of aminoacyl-tRNA synthetases (RSs), (e.g., the plurality of RSs can include mutant RSs, RSs derived from a species other than the first species or both mutant RSs and RSs derived from a species other than the first species); 2) the orthogonal tRNA (O-tRNA) (e.g., from one or more species); and 3) a polynucleotide that encodes an (e.g., positive) selection marker and comprises at least one selector codon. Cells are selected or screened for those that show an enhancement in suppression efficiency compared to cells lacking or with a reduced amount of the member of the plurality of RSs. Suppression efficiency can be measured by techniques known in the art and as described herein. Cells having an enhancement in suppression efficiency comprise an active RS that aminoacylates the O-tRNA. A level of aminoacylation (in vitro or in vivo) by the active RS of a first set of tRNAs from the first species is compared to the level of aminoacylation (in vitro or in vivo) by the active RS of a second set of tRNAs from the second species. The level of aminoacylation can be determined by a detectable substance (e.g., a labeled unnatural amino acid). The active RS that more efficiently aminoacylates the second set of tRNAs compared to the first set of tRNAs is typically selected, thereby providing an efficient (optimized) orthogonal aminoacyl-tRNA synthetase for use with the O-tRNA. An O-RS, identified by the method, is also a feature of the invention.

Any of a number of assays can be used to determine aminoacylation. These assays can be performed in vitro or in vivo. For example, in vitro aminoacylation assays are described in, e.g., Hoben and Soll (1985) *Methods Enzymol.* 113:55-59. Aminoacylation can also be determined by using a reporter along with orthogonal translation components and detecting the reporter in a cell expressing a polynucleotide comprising at least one selector codon that encodes a protein. See also, WO 2002/085923, entitled "IN VIVO INCORPORATION OF UNNATURAL AMINO ACIDS;" and WO 2004/094593, entitled "EXPANDING THE EUKARYOTIC GENETIC CODE."

Identified O-RS can be further manipulated to alter substrate specificity of the synthetase, so that only a desired unnatural amino acid, but not any of the common 20 amino acids, are charged to the O-tRNA. Methods to generate an orthogonal aminoacyl tRNA synthetase with a substrate specificity for an unnatural amino acid include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

A library of mutant O-RSs can be generated using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant RSs can be produced from two or more other, e.g., smaller, less diverse "sub-libraries." Chimeric libraries of RSs are also included in the invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

Once the synthetases are subject to the positive and negative selection/screening strategy, these synthetases can then be subjected to further mutagenesis. For example, a nucleic acid that encodes the O-RS can be isolated; a set of polynucleotides that encode mutated O-RSs (e.g., by random mutagenesis, site-specific mutagenesis, recombination or any combination thereof) can be generated from the nucleic acid; and, these individual steps or a combination of these steps can be repeated until a mutated O-RS is obtained that preferentially aminoacylates the O-tRNA with the unnatural amino acid. In some aspects of the invention, the steps are performed multiple times, e.g., at least two times.

Additional levels of selection/screening stringency can also be used in the methods of the invention, for producing O-tRNA, O-RS, or pairs thereof. The selection or screening stringency can be varied on one or both steps of the method to produce an O-RS. This could include, e.g., varying the amount of selection/screening agent that is used, etc. Additional rounds of positive and/or negative selections can also be performed. Selecting or screening can also comprise one or more of a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Additional general details for producing O-RS, and altering the substrate specificity of the synthetase can be found in Internal Publication Number WO 2002/086075, entitled "METHODS AND COMPOSITIONS FOR THE PRODUCTION OF ORTHOGONAL tRNA AMINOACYL-tRNA SYNTHETASE PAIRS;" and WO 2004/094593, entitled "EXPANDING THE EUKARYOTIC GENETIC CODE." See also, Wang and Schultz "Expanding the Genetic Code," *Angewandte Chemie Int. Ed.,* 44(1):34-66 (2005), the content of which is incorporated by reference in its entirety.

Source and Host Organisms

The orthogonal translational components (O-tRNA and O-RS) finding use with the invention can be derived from any organism (or a combination of organisms) for use in a host translation system from any other species, with the caveat that the O-tRNA/O-RS components and the host system work in an orthogonal manner. It is not a requirement that the O-tRNA and the O-RS from an orthogonal pair be derived from the same organism. In some aspects, the orthogonal components are derived from Archaea genes (i.e., archaebacteria) for use in a eubacterial host system.

For example, the orthogonal O-tRNA can be derived from an Archae organism, e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium,* or the like, or a eubacterium, such as *Escherichia coli, Thermus thermophilus, Bacillus stearothermphilus,* or the like, while the orthogonal O-RS can be derived from an organism or combination of organisms, e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium,* or the like, or a eubacterium, such as *Escherichia coli, Thermus thermophilus, Bacillus stearothermphilus,* or the like. In one embodiment, eukaryotic sources, e.g., plants, algae, protists, fungi, yeasts, animals (e.g., mammals, insects, arthropods, etc.), or the like, can also be used as sources of O-tRNAs and O-RSs.

The individual components of an O-tRNA/O-RS pair can be derived from the same organism or different organisms. In one embodiment, the O-tRNA/O-RS pair is from the same organism. Alternatively, the O-tRNA and the O-RS of the O-tRNA/O-RS pair are from different organisms.

The O-tRNA, O-RS or O-tRNA/O-RS pair can be selected or screened in vivo or in vitro and/or used in a cell, e.g., a eubacterial cell, to produce a polypeptide with an unnatural amino acid. The eubacterial cell used is not limited, for example, *Escherichia coli, Thermus thermophilus, Bacillus stearothermophilus,* or the like. Compositions of eubacterial cells comprising translational components of the invention are also a feature of the invention.

See also, International Application Publication Number WO 2004/094593, entitled "EXPANDING THE EUKARYOTIC GENETIC CODE," filed Apr. 16, 2004, for screening O-tRNA and/or O-RS in one species for use in another species.

In some aspects, the O-tRNA, O-RS or O-tRNA/O-RS pair can be selected or screened in vivo or in vitro and/or used in a cell, e.g., a eukaryotic cell, to produce a polypeptide with an unnatural amino acid. The eukaryotic cell used is not limited; for example, any suitable yeast cell, such as *Saccharomyces cerevisiae* (*S. cerevisiae*) or the like, can be used. Compositions of eukaryotic cells comprising translational components of the invention are also a feature of the invention.

Although orthogonal translation systems (e.g., comprising an O-RS, an O-tRNA and an unnatural amino acid) can utilize cultured host cells to produce proteins having unnatural amino acids, it is not intended that an orthogonal translation system of the invention require an intact, viable host cell. For example, a orthogonal translation system can utilize a cell-free system in the presence of a cell extract. Indeed, the use of cell free, in vitro transcription/translation systems for protein production is a well established technique. Adaptation of these in vitro systems to produce proteins having unnatural amino acids using orthogonal translation system components described herein is well within the scope of the invention.

Selector Codons

Selector codons in orthogonal translation systems expand the genetic codon framework of protein biosynthetic machinery. For example, a selector codon includes, e.g., a unique three base codon, a nonsense codon, such as a stop codon, e.g., an amber codon (UAG), or an opal codon (UGA), an unnatural codon, at least a four base codon, a rare codon, or the like. A number of selector codons can be introduced into a desired gene, e.g., one or more, two or more, more than three, etc. By using different selector codons, multiple orthogonal tRNA/synthetase pairs can be used that allow the simultaneous site-specific incorporation of multiple unnatural amino acids e.g., including at least one unnatural amino acid, using these different selector codons.

In one embodiment, the methods involve the use of a selector codon that is a stop codon for the incorporation of an unnatural amino acid in vivo in a cell into a polypeptide. For example, an O-tRNA is produced that recognizes the stop codon and is aminoacylated by an O-RS with an unnatural amino acid. This O-tRNA is not recognized by the naturally occurring host's aminoacyl-tRNA synthetases. Conventional site-directed mutagenesis can be used to introduce the stop codon at the site of interest in a polynucleotide encoding a polypeptide of interest. See, e.g., Sayers et al. (1988), 5',3' *Exonuclease in phosphorothioate-based oligonucleotide-directed mutagenesis. Nucleic Acids Res,* 791-802. When the O-RS, O-tRNA and the nucleic acid that encodes a polypeptide of interest are combined, e.g., in vivo, the unnatural amino acid is incorporated in response to the stop codon to give a polypeptide containing the unnatural amino acid at the specified position. In one embodiment of the invention, the stop codon used as a selector codon is an amber codon, UAG, and/or an opal codon, UGA. In one example, a genetic code in which UAG and UGA are both used as a selector codon can encode 22 amino acids while preserving the ochre nonsense codon, UAA, which is the most abundant termination signal.

The incorporation of unnatural amino acids in vivo can be done without significant perturbation of the host cell. For example in non-eukaryotic cells, such as *Escherichia coli*, because the suppression efficiency for the UAG codon depends upon the competition between the O-tRNA, e.g., the amber suppressor tRNA, and the release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. In eukaryotic cells, because the suppression efficiency for the UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA. In addition, additional compounds can also be present, e.g., reducing agents such as dithiothretiol (DTT).

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry*, 32:7939 (1993). In this case, the synthetic tRNA competes with the naturally occurring tRNA$^{Arg}$, which exists as a minor species in *Escherichia coli*. In addition, some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.* 25:4685 (1997). Components of the invention can be generated to use these rare codons in vivo.

Selector codons can also comprise extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC and the like. Methods of the invention include using extended codons based on frameshift suppression. Four or more base codons can insert, e.g., one or multiple unnatural amino acids, into the same protein. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See also, Anderson et al., (2002) *Exploring the Limits of Codon and Anticodon Size, Chemistry and Biology*, 9:237-244; and, Magliery, (2001) *Expanding the Genetic Code: Selection of Efficient Suppressors of Four-base Codons and Identification of "Shifty" Four-base Codons with a Library Approach in Escherichia coli*, *J. Mol. Biol.* 307: 755-769.

For example, four-base codons have been used to incorporate unnatural amino acids into proteins using in vitro biosynthetic methods. See, e.g., Ma et al., (1993) *Biochemistry*, 32:7939; and Hohsaka et al., (1999) *J. Am. Chem. Soc.*, 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.*, 121:12194. In an in vivo study, Moore et al. examined the ability of tRNA$^{Leu}$ derivatives with NCUA anticodons to suppress UAGN codons (N can be U, A, G, or C), and found that the quadruplet UAGA can be decoded by a tRNA$^{Leu}$ with a UCUA anticodon with an efficiency of 13 to 26% with little decoding in the 0 or −1 frame. See Moore et al., (2000) *J. Mol. Biol.*, 298:195. In one embodiment, extended codons based on rare codons or nonsense codons can be used in invention, which can reduce missense readthrough and frameshift suppression at other unwanted sites. Four base codons have been used as selector codons in a variety of orthogonal systems. See, e.g., WO 2005/019415; WO 2005/007870 and WO 2005/07624. See also, Wang and Schultz "Expanding the Genetic Code," *Angewandte Chemie Int. Ed.*, 44(1):34-66 (2005), the content of which is incorporated by reference in its entirety. While the examples below utilize an amber selector codon, four or more base codons can be used as well, by modifying the examples herein to include four-base O-tRNAs and synthetases modified to include mutations similar to those previously described for various unnatural amino acid O-RSs.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein*, Nature Biotechnology, 20:177-182. See also Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.*, 111:8322; and Piccirilli et al., (1990) *Nature*, 343:33; Kool, (2000) *Curr. Opin. Chem. Biol.*, 4:602. These bases in general mispair to some degree with natural bases and cannot be enzymatically replicated. Kool and co-workers demonstrated that hydrophobic packing interactions between bases can replace hydrogen bonding to drive the formation of base pair. See Kool, (2000) *Curr. Opin. Chem. Biol.*, 4:602; and Guckian and Kool, (1998) *Angew. Chem. Int. Ed. Engl.*, 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of

*Escherichia coli* DNA polymerase I (KF). See, e.g., McMinn et al., (1999) *J. Am. Chem. Soc.* 121:11586; and Ogawa et al., (2000) *J. Am. Chem. Soc.*, 122:3274. A 3MN:3MN self-pair can be synthesized by KF with efficiency and selectivity sufficient for biological function. See, e.g., Ogawa et al., (2000) *J. Am. Chem. Soc.*, 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.*, 123:7439. A novel metallobase pair, Dipic:Py, has also been developed, which forms a stable pair upon binding Cu(II). See Meggers et al., (2000) *J. Am. Chem. Soc.*, 122:10714. Because extended codons and unnatural amino acids are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Unnatural Amino Acids

As used herein, an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

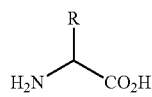

I

An unnatural amino acid is typically any structure having Formula I where the R group is any substituent other than one used in the twenty natural amino acids. See e.g., *Biochemistry* by L. Stryer, 3$^{rd}$ ed. 1988, Freeman and Company, New York, for structures of the twenty natural amino acids. Note that, the unnatural amino acids of the invention can be naturally occurring compounds other than the twenty alpha-amino acids above.

Because the unnatural amino acids of the invention typically differ from the natural amino acids in side chain, the unnatural amino acids form amide bonds with other amino acids, e.g., natural or unnatural, in the same manner in which they are formed in naturally occurring proteins. However, the unnatural amino acids have side chain groups that distinguish them from the natural amino acids.

FIG. 1 provides the structures of unnatural amino acids that are used in the working examples of the present invention. These unnatural amino acids can be incorporated into proteins using suitable O-RS and O-tRNA pairs. For example, p-benzoyl-L-phenylalanine (Bpa) can be incorporated using an orthogonal translation pair comprising the O-tRNA of SEQ ID NO: 1 and the cognate O-RS of SEQ ID NO: 4. para-acetyl-L-phenylalanine (pAcPhe) can be incorporated using an orthogonal translation pair comprising the O-tRNA of SEQ ID NO: 1 and the cognate O-RS of SEQ ID NO: 6. para-azido-L-phenylalanine (pAzPhe) can be incorporated using an orthogonal translation pair comprising the O-tRNA of SEQ ID NO: 1 and the cognate O-RS of SEQ ID NO: 8. para-iodo-L-phenylalanine (pIPhe) can be incorporated using an orthogonal translation pair comprising the O-tRNA of SEQ ID NO: 1 and the cognate O-RS of SEQ ID NO: 10.

However, the unnatural amino acids used herein serve only to illustrate the broader applicability of the invention, and the invention is not limited to the use of these amino acids shown in FIG. 1.

A plurality of different unnatural amino acids can be simultaneously incorporated into a polypeptide of interest, e.g., using an appropriate second O-RS/O-tRNA pair in conjunction with the first orthogonal pair, and where the first and second orthogonal pairs use different selector codons.

In other unnatural amino acids, for example, R in Formula I optionally comprises an alkyl-, aryl-, acyl-, hydrazine, cyano-, halo-, hydrazide, alkenyl, ether, borate, boronate, phospho, phosphono, phosphine, enone, imine, ester, hydroxylamine, amine, and the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, biotin or biotin-analogue containing amino acids, keto containing amino acids, glycosylated amino acids, a saccharide moiety attached to the amino acid side chain, amino acids comprising polyethylene glycol or polyether, heavy atom substituted amino acids, chemically cleavable or photocleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, amino thioacid containing amino acids, and amino acids containing one or more toxic moiety.

In another aspect, the invention provides unnatural amino acids having the general structure illustrated by Formula IV below:

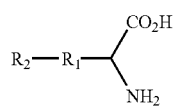

IV

An unnatural amino acid having this structure is typically any structure where $R_1$ is a substituent used in one of the twenty natural amino acids (e.g., tyrosine or phenylalanine) and $R_2$ is a substituent. Thus, this type of unnatural amino acid can be viewed as a natural amino acid derivative.

Unnatural amino acids can also optionally comprise modified backbone structures, e.g., as illustrated by the structures of Formula II and III:

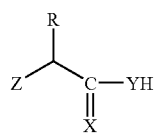

II

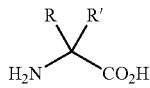

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8 and 9 membered ring proline analogues, β and γ amino acids such as substituted β-alanine and γ-amino butyric acid.

In some aspects, the invention utilizes unnatural amino acids in the L-configuration. However, it is not intended that the invention be limited to the use of L-configuration unnatural amino acids. It is contemplated that the D-enantiomers of these unnatural amino acids also find use with the invention.

Tyrosine analogs include para-substituted tyrosines, ortho-substituted tyrosines, and meta substituted tyrosines, wherein the substituted tyrosine comprises an alkynyl group, acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenyalanines, and meta-substituted phenylalanines, wherein the substituent comprises an alkynyl group, a hydroxy group, a methoxy group, a methyl group, an allyl group, an aldehyde, a nitro, a thiol group, or keto group, or the like. Specific examples of unnatural amino acids include, but are not limited to, p-ethylthiocarbonyl-L-phenylalanine, p-(3-oxobutanoyl)-L-phenylalanine, 1,5-dansyl-alanine, 7-amino-coumarin amino acid, 7-hydroxy-coumarin amino acid, nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridyl alanine, p-(2-amino-1-hydroxyethyl)-L-phenylalanine, p-isopropylthiocarbonyl-L-phenylalanine, 3-nitro-L-tyrosine and p-nitro-L-phenylalanine. Also, a p-propargyloxyphenylalanine, a 3,4-dihydroxy-L-phenyalanine (DHP), a 3,4,6-trihydroxy-L-phenylalanine, a 3,4,5-trihydroxy-L-phenylalanine, 4-nitro-phenylalanine, a p-acetyl-L-phenylalanine, O-methyl-L-tyrosine, an L-3-(2-naphthyl) alanine, a 3-methyl-phenylalanine, an O-4-allyl-L-tyrosine, a 4-propyl-L-tyrosine, a 3-nitro-tyrosine, a 3-thiol-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of unnatural amino acids that can be incorporated using orthogonal translation systems are known. See the references cited herein, each of which is incorporated herein by reference in its entirety.

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King and Kidd (1949) *A New Synthesis of Glutamine and of γ-Dipeptides of Glutamic Acid from Phthylated Intermediates. J. Chem. Soc.*, 3315-3319; Friedman and Chatterrji (1959) *Synthesis of Derivatives of Glutamine as Model Substrates for Anti-Tumor Agents. J. Am. Chem. Soc.* 81, 3750-3752; Craig et al. (1988) *Absolute Configuration of the Enantiomers of 7-Chloro-4 [[4-(diethylamino)-1-methylbutyl]amino]quinoline (Chloroquine). J. Org. Chem.* 53, 1167-1170; Azoulay et al., (1991) *Glutamine analogues as Potential Antimalarials. Eur. J. Med. Chem.* 26, 201-5; Koskinen and Rapoport (1989) *Synthesis of 4-Substituted Prolines as Conformationally Constrained Amino Acid Analogues. J. Org. Chem.* 54, 1859-1866; Christie and Rapoport (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 1989:1859-1866; Barton et al. (1987) *Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives. Tetrahedron Lett.* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also, International Publication WO 2004/058946, entitled "PROTEIN ARRAYS," filed on Dec. 22, 2003.

Cellular Uptake of Unnatural Amino Acids

Unnatural amino acid uptake by a cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the cell via a collection of protein-based transport systems often displaying varying degrees of amino acid specificity. A rapid screen can be done which assesses which unnatural amino acids, if any, are taken up by cells. See, e.g., the toxicity assays in, e.g., International Publication WO 2004/058946, entitled "PROTEIN ARRAYS," filed on Dec. 22, 2003; and Liu and Schultz (1999) *Progress toward the evolution of an organism with an*

*expanded genetic code. PNAS* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923, supra) relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in GenBank. Artificially evolved enzymes are also optionally added into a cell in the same manner. In this manner, the cellular machinery and resources of a cell are manipulated to produce unnatural amino acids.

Indeed, any of a variety of methods can be used for producing novel enzymes for use in biosynthetic pathways, or for evolution of existing pathways, for the production of unnatural amino acids, in vitro or in vivo. Many available methods of evolving enzymes and other biosynthetic pathway components can be applied to the present invention to produce unnatural amino acids (or, indeed, to evolve synthetases to have new substrate specificities or other activities of interest). For example, DNA shuffling is optionally used to develop novel enzymes and/or pathways of such enzymes for the production of unnatural amino acids (or production of new synthetases), in vitro or in vivo. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA,* 91:10747-10751. A related approach shuffles families of related (e.g., homologous) genes to quickly evolve enzymes with desired characteristics. An example of such "family gene shuffling" methods is found in Crameri et al. (1998) "DNA shuffling of a family of genes from diverse species accelerates directed evolution" *Nature,* 391(6664): 288-291. New enzymes (whether biosynthetic pathway components or synthetases) can also be generated using a DNA recombination procedure known as "incremental truncation for the creation of hybrid enzymes" ("ITCHY"), e.g., as described in Ostermeier et al. (1999) "A combinatorial approach to hybrid enzymes independent of DNA homology" *Nature Biotech* 17:1205. This approach can also be used to generate a library of enzyme or other pathway variants which can serve as substrates for one or more in vitro or in vivo recombination methods. See, also, Ostermeier et al. (1999) "Combinatorial Protein Engineering by Incremental Truncation," *Proc. Natl. Acad. Sci. USA,* 96: 3562-67, and Ostermeier et al. (1999), "Incremental Truncation as a Strategy in the Engineering of Novel Biocatalysts," *Biological and Medicinal Chemistry,* 7: 2139-44. Another approach uses exponential ensemble mutagenesis to produce libraries of enzyme or other pathway variants that are, e.g., selected for an ability to catalyze a biosynthetic reaction relevant to producing an unnatural amino acid (or a new synthetase). In this approach, small groups of residues in a sequence of interest are randomized in parallel to identify, at each altered position, amino acids which lead to functional proteins. Examples of such procedures, which can be adapted to the present invention to produce new enzymes for the production of unnatural amino acids (or new synthetases) are found in Delegrave and Youvan (1993) *Biotechnology Research* 11:1548-1552. In yet another approach, random or semi-random mutagenesis using doped or degenerate oligonucleotides for enzyme and/or pathway component engineering can be used, e.g., by using the general mutagenesis methods of e.g., Arkin and Youvan (1992) "Optimizing nucleotide mixtures to encode specific subsets of amino acids for semi-random mutagenesis" *Biotechnology* 10:297-300; or Reidhaar-Olson et al. (1991) "Random mutagenesis of protein sequences using oligonucleotide cassettes" *Methods Enzymol.* 208:564-86. Yet another approach, often termed a "non-stochastic" mutagenesis, which uses polynucleotide reassembly and site-saturation mutagenesis can be used to produce enzymes and/or pathway components, which can then be screened for an ability to perform one or more synthetase or biosynthetic pathway function (e.g., for the production of unnatural amino acids in vivo). See, e.g., WO 2000/046344, entitled "NON-STOCHASTIC GENERATION OF GENETIC VACCINES AND ENZYMES" to Short.

An alternative to such mutational methods involves recombining entire genomes of organisms and selecting resulting progeny for particular pathway functions (often referred to as "whole genome shuffling"). This approach can be applied to the present invention, e.g., by genomic recombination and selection of an organism (e.g., an *E. coli* or other cell) for an ability to produce an unnatural amino acid (or intermediate thereof). For example, methods taught in the following publications can be applied to pathway design for the evolution of existing and/or new pathways in cells to produce unnatural amino acids in vivo: Patnaik et al. (2002) "Genome shuffling of *lactobacillus* for improved acid tolerance" *Nature Biotechnology,* 20(7): 707-712; and Zhang et al. (2002) "Genome shuffling leads to rapid phenotypic improvement in bacteria" Nature, February 7, 415(6872): 644-646.

Other techniques for organism and metabolic pathway engineering, e.g., for the production of desired compounds are also available and can also be applied to the production of unnatural amino acids. Examples of publications teaching useful pathway engineering approaches include: Nakamura and White (2003) "Metabolic engineering for the microbial production of 1,3 propanediol" *Curr. Opin. Biotechnol.* 14(5):454-9; Berry et al. (2002) "Application of Metabolic Engineering to improve both the production and use of Biotech Indigo" *J. Industrial Microbiology and Biotechnology* 28:127-133; Banta et al. (2002) "Optimizing an artificial metabolic pathway: Engineering the cofactor specificity of *Corynebacterium* 2,5-diketo-D-gluconic acid reductase for use in vitamin C biosynthesis" *Biochemistry,* 41(20), 6226-36; Selivonova et al. (2001) "Rapid Evolution of Novel Traits in Microorganisms" *Applied and Environmental Microbiology,* 67:3645, and many others.

Regardless of the method used, typically, the unnatural amino acid produced with an engineered biosynthetic pathway of the invention is produced in a concentration sufficient for efficient protein biosynthesis, e.g., a natural cellular amount, but not to such a degree as to significantly affect the concentration of other cellular amino acids or to exhaust cellular resources. Typical concentrations produced in vivo in this manner are about 10 mM to about 0.05 mM. Once a cell is engineered to produce enzymes desired for a specific pathway and an unnatural amino acid is generated, in vivo selections are optionally used to further optimize the production of the unnatural amino acid for both ribosomal protein synthesis and cell growth.

Orthogonal Components Finding Use with the Invention

The incorporation of the unnatural amino acid into protein is accomplished by orthogonal pairs that incorporate the unnatural amino acid in response the selector codon genetic signal in *E. coli*, where the orthogonal components do not cross-react with endogenous *E. coli* components of the translational machinery of the host cell, but recognize the desired unnatural amino acid and incorporate it into proteins in response to the selector codon (e.g., an amber nonsense codon, TAG). The orthogonal components finding use with the invention include orthogonal aminoacyl-tRNA synthetases derived from *Methanococcus jannaschii* tyrosyl tRNA-synthetase, and the mutant tyrosyl tRNA$_{CUA}$ amber suppressor, which function as an orthogonal pair in a eubacterial host cell such as *E. coli*. In this system, the mutant aminoacyl-tRNA synthetases aminoacylate the suppressor tRNA with its respective unnatural amino acid and not with any of the common twenty amino acids.

Methods of producing orthogonal components find use with the invention, where these methods result in the incorporation of unnatural amino acids, for example but not limited to the unnatural amino acids provided in FIG. 1, into a growing polypeptide chain in response to a selector codon, e.g., an amber stop codon, a nonsense codon, a four or more base codon, etc., e.g., in vivo. For example, orthogonal-tRNAs (O-tRNAs), orthogonal aminoacyl-tRNA synthetases (O-RSs) and pairs thereof find use with the invention.

In some embodiments, these pairs can be used to incorporate an unnatural amino acid into growing polypeptide chains, and subsequently the polypeptide is post-translationally modified. For additional information regarding unnatural amino acids that can be post-translationally modified, see, for example, the unnatural amino acid orthogonal systems described in Chin et al., *Science* (2003) 301:964-967; Zhang et al., *Proc. Natl. Acad. Sci. U.S.A.* 2004, 101:8882-8887; Anderson et al., *Proc. Natl. Acad. Sci. U.S.A.* 2004, 101:7566-7571; Wang et al., (2001) *Science* 292:498-500; Chin et al., (2002) *Journal of the American Chemical Society* 124:9026-9027; Chin and Schultz, (2002) *ChemBioChem* 11:1135-1137; Chin, et al., (2002) *PNAS United States of America* 99:11020-11024; Wang and Schultz, (2002) *Chem. Comm.*, 1-10; Wang and Schultz "Expanding the Genetic Code," *Angewandte Chemie Int. Ed.*, 44(1):34-66 (2005); Xie and Schultz, "An Expanding Genetic Code," *Methods* 36:227-238 (2005); and Deiters et al, *Bioorganic & Medicinal Chemistry Letters* 15:1521-1524 (2005), each of which is incorporated by reference in its entirety.

See also the unnatural amino acid orthogonal systems described in International Publications WO 2002/086075, entitled "METHODS AND COMPOSITIONS FOR THE PRODUCTION OF ORTHOGONAL tRNA AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO2005/007870, filed Jul. 7, 2004; WO 2005/007624, filed Jul. 7, 2004; WO 2006/034332, filed on Sep. 20, 2005; and WO 2006/110182 entitled "ORTHOGONAL TRANSLATION COMPONENTS FOR THE IN VIVO INCORPORATION OF UNNATURAL AMINO ACIDS" filed Oct. 27, 2005 by Schultz et al.

In certain embodiments, the O-RS finding use with the invention preferentially aminoacylates the O-tRNA over any endogenous tRNA with an the particular unnatural amino acid, where the O-RS has a bias for the O-tRNA, and where the ratio of O-tRNA charged with an unnatural amino acid to the endogenous tRNA charged with the same unnatural amino acid is greater than 1:1, and more preferably where the O-RS charges the O-tRNA exclusively or nearly exclusively.

The invention also makes use of orthogonal tRNAs (O-tRNA), where the O-tRNA recognizes a selector codon. Typically, an O-tRNA includes at least about, e.g., a 45%, a 50%, a 60%, a 75%, an 80%, or a 90% or more suppression efficiency in the presence of a cognate synthetase in response to a selector codon as compared to the suppression efficiency of an O-tRNA comprising or encoded by a polynucleotide sequence as set forth in the sequence listings (e.g., SEQ ID NO: 1). In one embodiment, the suppression efficiency of the O-RS and the O-tRNA together is, e.g., 5 fold, 10 fold, 15 fold, 20 fold, 25 fold or more greater than the suppression efficiency of the O-tRNA in the absence of an O-RS. In some aspects, the suppression efficiency of the O-RS and the O-tRNA together is at least 45% of the suppression efficiency of an orthogonal tyrosyl-tRNA synthetase pair derived from *Methanococcus jannaschii*.

The invention makes use of cells (e.g., *E. coli*) comprising a translation system and nucleotide sequences that program protein production, where the translation system includes an orthogonal-tRNA (O-tRNA), an orthogonal aminoacyl-tRNA synthetase (O-RS), and, an unnatural amino acid. Typically, the O-RS preferentially aminoacylates the O-tRNA over any endogenous tRNA with the unnatural amino acid, where the O-RS has a bias for the O-tRNA, and where the ratio of O-tRNA charged with the unnatural amino acid to the endogenous tRNA charged with the unnatural amino acid is greater than 1:1, and more preferably where the O-RS charges the O-tRNA exclusively or nearly exclusively. The O-tRNA recognizes the first selector codon, and the O-RS preferentially aminoacylates the O-tRNA with an unnatural amino acid.

Various polynucleotides also find use with the invention. These polynucleotides include an artificial (e.g., man-made, and not naturally occurring, e.g., recombinant) polynucleotide comprising a nucleotide sequence encoding an O-RS. A polynucleotide finding use with the invention can also includes a nucleic acid that hybridizes to a polynucleotide described above, under highly stringent conditions, over substantially the entire length of the nucleic acid. Vectors comprising polynucleotides also find use with the invention. For example, a vector can include a plasmid, a cosmid, a phage, a virus, an expression vector, and/or the like. Methods for producing components of an O-tRNA/O-RS pair are known and find use with the invention. See the present disclosure and the reference cited herein.

Nucleic Acid and Polypeptide Sequences and Variants

As described herein, polynucleotide sequences encoding, e.g., O-tRNAs and O-RSs, find use with the invention, as do the respective amino acid sequences encoded by the polynucleotides. The disclosure provides and references examples of polynucleotide and polypeptide sequences that find use with the invention. However, it will be appreciated that use of the invention is not limited to those sequences disclosed herein. One of skill will appreciate that the invention also provides many related sequences with the functions described herein, e.g., polynucleotides and polypeptides encoding conservative variants of an O-RS disclosed herein.

A polynucleotide finding use with the invention also includes an artificial polynucleotide that is, e.g., at least 75%, at least 80%, at least 90%, at least 95%, at least 98% or more identical to that of a naturally occurring tRNA, (but is other than a naturally occurring tRNA). A polynucleotide finding use with the invention also includes an artificial polynucleotide that is, e.g., at least 75%, at least 80%, at least 90%, at least 95%, at least 98% or more identical (but not 100% identical) to that of a naturally occurring tRNA.

In certain embodiments, a vector finding use with the invention (e.g., a plasmid, a cosmid, a phage, a virus, etc.) comprises a polynucleotide that finds use with the invention. In some embodiments, the vector is an expression vector. In other embodiments, the expression vector includes a promoter operably linked to one or more of the polynucleotides of the invention. In other embodiments, a cell comprises a vector that includes a polynucleotide finding use with the invention.

One of skill will appreciate that many variants of the disclosed sequences also find use with the invention. For example, conservative variations of the disclosed sequences that yield a functionally identical sequence find use with the invention. Variants of the nucleic acid polynucleotide sequences, wherein the variants hybridize to at least one disclosed sequence, find use with the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional sequence, is a conservative variation of the basic nucleic acid.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

TABLE 1

Conservative Amino Acid Substitutions

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Nucleic Acid Hybridization

Comparative hybridization can be used to identify nucleic acids that find use with the invention, including conservative variations of nucleic acids provided herein, and this comparative hybridization method is a preferred method of distinguishing nucleic acids that find use with the invention. Target nucleic acids which hybridize to nucleic acids provided or referenced herein under high, ultra-high and ultra-ultra high stringency conditions also find use with the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in *Current Protocols in Molecular Biology*, Ausubel et al., eds., *Current Protocols*, a joint venture between Greene Publishing Associates, Inc. and John Wiley & Sons, Inc., (supplemented through 2004) ("Ausubel"); Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher)

than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In some aspects, the invention utilizes a nucleic acid that comprises a unique subsequence in a nucleic acid selected from the sequences of O-tRNAs and O-RSs disclosed or referenced herein. The unique subsequence is unique as compared to a nucleic acid corresponding to any known O-tRNA or O-RS nucleic acid sequence. Alignment can be performed using, e.g., BLAST set to default parameters. Any unique subsequence is useful, e.g., as a probe to identify the nucleic acids of the invention.

Similarly, the invention utilizes a polypeptide which comprises a unique subsequence in a polypeptide selected from the sequences of O-RSs disclosed or referenced herein. Here, the unique subsequence is unique as compared to a polypeptide corresponding to any of known polypeptide sequence.

The invention also provides for target nucleic acids which hybridizes under stringent conditions to a unique coding oligonucleotide which encodes a unique subsequence in a polypeptide selected from the sequences of O-RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2004).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

Polynucleotide and polypeptides of the invention and used in the invention can be manipulated using molecular biological techniques. General texts which describe molecular biological techniques include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through 2004) ("Ausubel"). These texts describe mutagenesis, the use of vectors, promoters and many other relevant topics related to, e.g., the generation of genes that include selector codons for production of proteins that include unnatural amino acids, orthogonal tRNAs, orthogonal synthetases, and pairs thereof.

Various types of mutagenesis can be used in conjunction with the invention, e.g., to mutate tRNA molecules, to produce libraries of tRNAs, to produce libraries of synthetases, to insert selector codons that encode an unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Host cells are genetically engineered (e.g., transformed, transduced or transfected) with the polynucleotides of the invention or constructs which include a polynucleotide, e.g., a vector, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman and Smith, *Gene* 8:81 (1979); Roberts, et al., *Nature*, 328:731 (1987); Schneider, B., et al., *Protein Expr. Purif.* 6435:10 (1995); Ausubel, Sambrook, Berger (all supra). The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)), and/or the like.

A highly efficient and versatile single plasmid system was developed for site-specific incorporation of unnatural amino acids into proteins in response to the amber stop codon (UAG) in *E. coli*. In the new system, the pair of *M. jannaschii* suppressor tRNAtyr(CUA) and tyrosyl-tRNA synthetase are encoded in a single plasmid, which is compatible with most *E. coli* expression vectors. Monocistronic tRNA operon under control of proK promoter and terminator was constructed for optimal secondary structure and tRNA processing. Introduction of a mutated form of glnS promoter for the synthetase resulted in a significant increase in both suppression efficiency and fidelity. Increases in suppression efficiency were also obtained by multiple copies of tRNA gene as well as by a specific mutation (D286R) on the synthetase (Kobayashi et al., "Structural basis for orthogonal tRNA specificities of tyrosyl-tRNA synthetases for genetic code expansion," Nat. Struct. Biol., 10(6):425-432 [2003]). The generality of the optimized system was also demonstrated by highly efficient and accurate incorporation of several different unnatural amino acids, whose unique utilities in studying protein function and structure were previously proven.

A catalogue of Bacteria and Bacteriophages useful for cloning is provided, e.g., by the ATCC, e.g., *The ATCC Catalogue of Bacteria and Bacteriophage* (1996) Gherna et al. (eds) published by the ATCC. Additional basic procedures for sequencing, cloning and other aspects of molecular biology and underlying theoretical considerations are also found in Sambrook (supra), Ausubel (supra), and in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex.), The Great American Gene Company (Ramona, Calif.), ExpressGen Inc. (Chicago, Ill.), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Proteins and Polypeptides of Interest

Methods of producing a protein comprising an unnatural amino acid at a specified position are also a feature of the invention. For example, a method can include growing, in an appropriate medium, a cell (e.g., in an *E. coli* cell), where the cell comprises a nucleic acid that comprises at least one selector codon and encodes a protein; and, providing the unnatural amino acid; where the cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the unnatural amino acid. The protein so produced in the *E. coli* comprises an unnatural amino acid at the position corresponding to the selector codon. That protein can then optionally be reacted under conditions where the unnatural amino acid undergoes covalent modification, thereby producing a post-translationally protein.

In certain embodiments, the O-RS comprises a bias for the aminoacylation of the cognate O-tRNA over any endogenous tRNA in an expression system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The protein comprising an unnatural amino acid at a specified position that is post-translationally modified is also a feature of the invention. The protein is produced in a cell, e.g., an *E. coli* cell. The O-tRNA/O-RS pairs also reside in the cell and utilize the host cell's translation machinery, which results in the in vivo incorporation of an unnatural amino acid into a fusion protein in response to a selector codon. The ability of an O-tRNA/O-RS system to function in a host cell to incorporate a wide variety of unnatural amino acids that can be post-translationally modified is known. See, e.g., Chin et al., *Science* (2003) 301:964-967; Zhang et al., *Proc. Natl. Acad. Sci. U.S.A.* 2004, 101:8882-8887; Anderson et al., *Proc. Natl. Acad. Sci. U.S.A.* 2004, 101:7566-7571; Wang et al., (2001) *Science* 292:498-500; Chin et al., (2002) *Journal of the American Chemical Society* 124:9026-9027; Chin and Schultz, (2002) *ChemBioChem* 11:1135-1137; Chin, et al., (2002) *PNAS United States of America* 99:11020-11024; Wang and Schultz, (2002) *Chem. Comm.,* 1-10; Wang and Schultz "Expanding the Genetic Code," *Angewandte Chemie Int. Ed.,* 44(1):34-66 (2005); Xie and Schultz, "An Expanding Genetic Code," *Methods* 36:227-238 (2005); and Deiters et al, *Bioorganic & Medicinal Chemistry Letters* 15:1521-1524 (2005), each of which is incorporated by reference in its entirety.

See also the unnatural amino acid orthogonal systems described in International Publications WO 2002/086075, entitled "METHODS AND COMPOSITIONS FOR THE PRODUCTION OF ORTHOGONAL tRNA AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO2005/007870, filed Jul. 7, 2004; WO 2005/007624, filed Jul. 7, 2004; WO 2006/034332, filed on Sep. 20, 2005; and WO 2006/110182 entitled "ORTHOGONAL TRANSLATION COMPONENTS FOR THE IN VIVO INCORPORATION OF UNNATURAL AMINO ACIDS," filed Oct. 27, 2005 by Schultz et al. Each of these references is incorporated by reference in its entirety.

The incorporation of an unnatural amino acid can be done to, e.g., tailor changes in protein structure and/or function, e.g., to change size, acidity, nucleophilicity, hydrogen bonding, hydrophobicity, accessibility of protease target sites, target to a moiety (e.g., for a protein array), incorporation of labels or reactive groups, etc. Proteins that include an unnatural amino acid can have enhanced or even entirely new catalytic or physical properties. For example, the following properties are optionally modified by inclusion of an unnatural amino acid into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one unnatural amino acid are useful for, e.g., novel therapeutics, diagnostics, catalytic enzymes, industrial enzymes, binding proteins (e.g., antibodies), and e.g., the study of protein structure and function. See, e.g., Dougherty, (2000) *Unnatural Amino Acids as Probes of Protein Structure and Function, Current Opinion in Chemical Biology*, 4:645-652. Proteins that comprise an unnatural amino acid that can be selectively post-translationally modified (e.g., by a [3+2]cycloaddition or a Staudinger modification) can be engineered to contain any desired functionality that can be coupled to the reaction partner. The nature of the reaction partner is not limited in any way, except only that it comprise a suitable reactive moiety that results in a covalent attachment to the unnatural amino acid residue in the polypeptide.

In some aspects, a composition includes a protein with at least one, e.g., at least two, at least three, at least four, at least five, at least six, at least seven, at least eight, at least nine, or at least ten or more unnatural amino acids. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is an unnatural amino acid. For a given protein with more than one unnatural amino acid, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Essentially any protein (or portion thereof) that includes an unnatural amino acid (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Examples of therapeutic, diagnostic, and other proteins that can be modified to comprise one or more unnatural amino acid can be found, but not limited to, those in International Publications WO 2004/094593, filed Apr. 16, 2004, entitled "Expanding the Eukaryotic Genetic Code;" and, WO 2002/085923, entitled "IN VIVO INCORPORATION OF UNNATURAL AMINO ACIDS." Examples of therapeutic, diagnostic, and other proteins that can be modified to comprise one or more unnatural amino acids include, but are not limited to, e.g., Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, I309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO"), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

One class of proteins that can be made using the compositions and methods for in vivo incorporation of unnatural amino acids in proteins described herein includes transcriptional modulators or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of proteins of the invention (e.g., proteins with one or more unnatural amino acids) include biologically active proteins such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes) or portions thereof with at least one unnatural amino acid are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many of these proteins are commercially available (See, e.g., the Sigma BioSciences catalogue), and the corresponding protein sequences and genes and, typically, many variants thereof, are well-known (see, e.g., Genbank). Any of them can be modified by the insertion of one or more unnatural amino acid according to the invention, e.g., to alter the protein with respect to one or more therapeutic, diagnostic or enzymatic properties of interest. Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids), reduction of $LD_{50}$ or other side effects, ability to enter the body through the gastric tract (e.g., oral availability), or the like. Examples of diagnostic properties include shelf half-life, stability, diagnostic activity, detectability, or the like. Examples of relevant enzymatic properties include shelf half-life, stability, enzymatic activity, production capability, or the like.

A variety of other proteins can also be modified to include one or more unnatural amino acid using compositions and methods of the invention. For example, the invention can include substituting one or more natural amino acids in one or more vaccine proteins with an unnatural amino acid, e.g., in proteins from infectious fungi, e.g., *Aspergillus, Candida* species; bacteria, particularly *E. coli*, which serves a model for pathogenic bacteria, as well as medically important bacteria such as *Staphylococci* (e.g., *aureus*), or *Streptococci* (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., *vaccinia*; Picornaviruses, e.g. *polio*; Togaviruses, e.g., *rubella*; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for unnatural amino acid modification.

In certain embodiments, the protein of interest (or portion thereof) is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of an unnatural amino acid. For example, a nucleic acid for a protein of interest is mutagenized to include one or more selector codon, providing for the insertion of the one or more unnatural amino acids. The invention includes any such variant, e.g., mutant, versions of any protein, e.g., including at least one unnatural amino acid. Similarly, the invention also includes corresponding nucleic acids, i.e., any nucleic acid with one or more selector codon that encodes one or more unnatural amino acid.

To make a protein that includes a post-translationally modified unnatural amino acid, one can use host cells and organisms that are adapted for the in vivo incorporation of the unnatural amino acid via orthogonal tRNA/RS pairs. Host cells are genetically engineered (e.g., transformed, transduced or transfected) with one or more vectors that express the orthogonal tRNA, the orthogonal tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

Defining Polypeptides by Immunoreactivity

Because the polypeptides of the invention provide a variety of new polypeptide sequences (e.g., polypeptides comprising unnatural amino acids in the case of proteins synthesized in the translation systems herein, or, e.g., in the case of the novel synthetases, novel sequences of standard amino acids), the polypeptides also provide new structural features which can be recognized, e.g., in immunological assays. The generation of antisera, which specifically bind the polypeptides of the invention, as well as the polypeptides which are bound by such antisera, are a feature of the invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology*, 4th Ed., 1999, Raven Press, New York, for antibody structure and terminology.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity.

Additional details on proteins, antibodies, antisera, etc. can be found in International Publication Numbers WO 2004/094593, entitled "EXPANDING THE EUKARYOTIC GENETIC CODE;" WO 2002/085923, entitled "IN VIVO INCORPORATION OF UNNATURAL AMINO ACIDS;" WO 2004/035605, entitled "GLYCOPROTEIN SYNTHESIS;" and WO 2004/058946, entitled "PROTEIN ARRAYS."

Kits

Kits are also a feature of the invention. For example, a kit for producing a polypeptide comprising at least one unnatural amino acid is a feature of the invention, where the kit comprises at least one construct of the invention. For example, such kits can comprise various components selected from: a container to hold the kit components, instructional materials for producing the polypeptide, nucleic acid comprising a polynucleotide sequence encoding an O-tRNA, nucleic acid comprising a polynucleotide encoding an O-RS, an unnatural amino acid, reagents for post-translational modification of the unnatural amino acid, and a suitable strain of E. coli host cells for expression of the O-tRNA/O-RS.

EXAMPLES

The following examples are offered to illustrate, but not to limit the claimed invention. One of skill will recognize a variety of non-critical parameters that may be altered without departing from the scope of the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example 1

The Construction of a Single-Plasmid System for the Expression of Polypeptides Comprising Unnatural Amino Acids The present Example describes the construction of a plasmid encoding both members of an orthogonal aminoacyl-tRNA and aminoacyl-tRNA synthetase pair for the incorporation of p-benzoyl-L-phenylalanine.

A plasmid was constructed (called pYR-BpaRS1) containing nucleotide sequences that encode both components of an orthogonal translation pair that function in an E. coli host cell. Namely, these two components are the orthogonal tRNA MjtRNA-Tyr(CUA) and the mutant MjTyrRS synthetase (BpaRS) that specifically aminoacylates the orthogonal tRNA with the photocrosslinking amino acid, p-benzoyl-L-phenylalanine (Bpa, see FIG. 1). See, Chin et al., Proc. Natl. Acad. Sci. USA 99:11020-11024 (2002).

Figure 2:
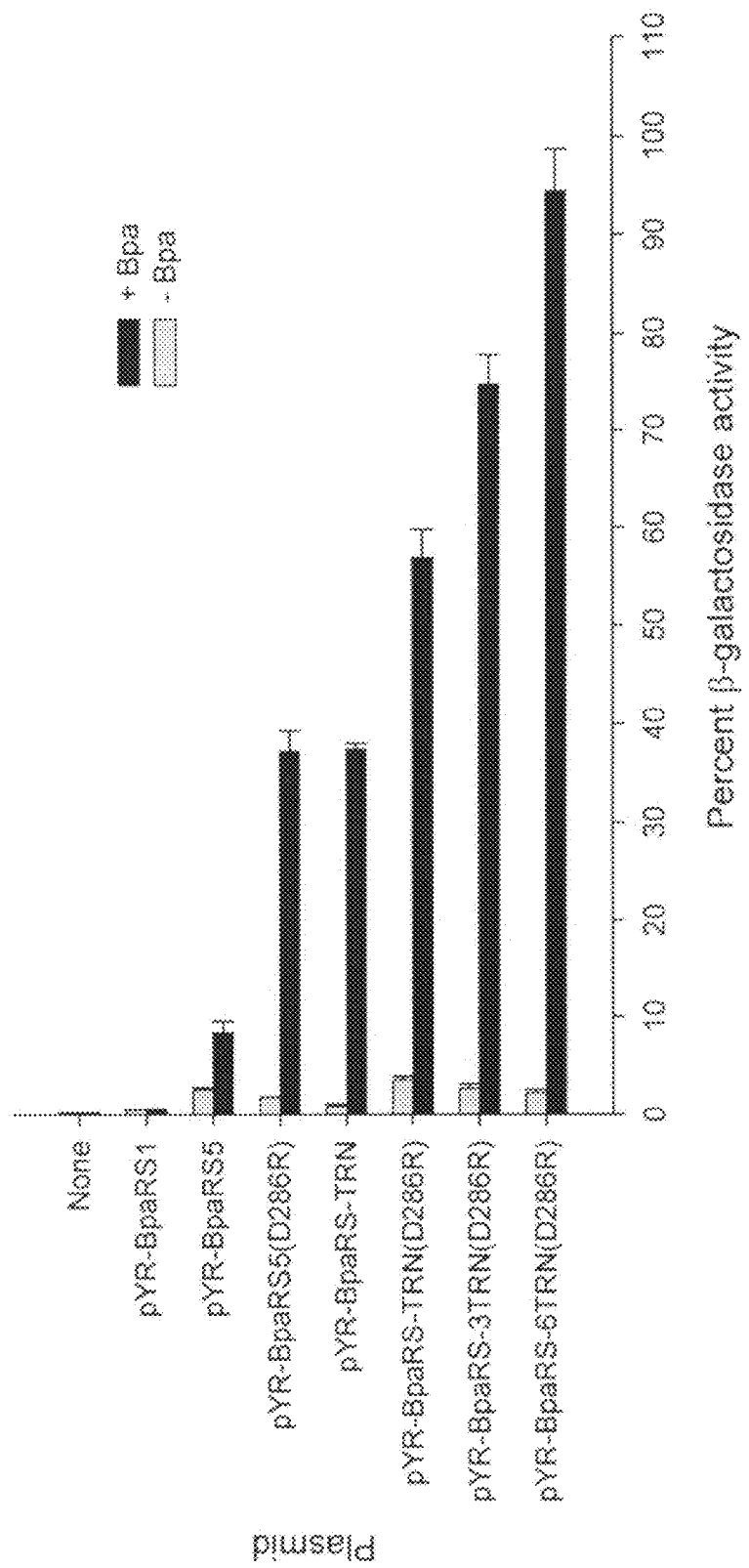
FIG. 2 provides a histogram showing the suppression efficiencies of plasmids (relative to wild-type β-galactosidase) with the proK promoter and terminator for the MjtRNA-Tyr (CUA) gene, the D286R mutation in the BpaRS gene, a mutated form of glnS promoter for the BpaRS gene, and/or multiple copies of the tRNA gene. Error bars indicate standard deviation and n=3.
Figure 3:
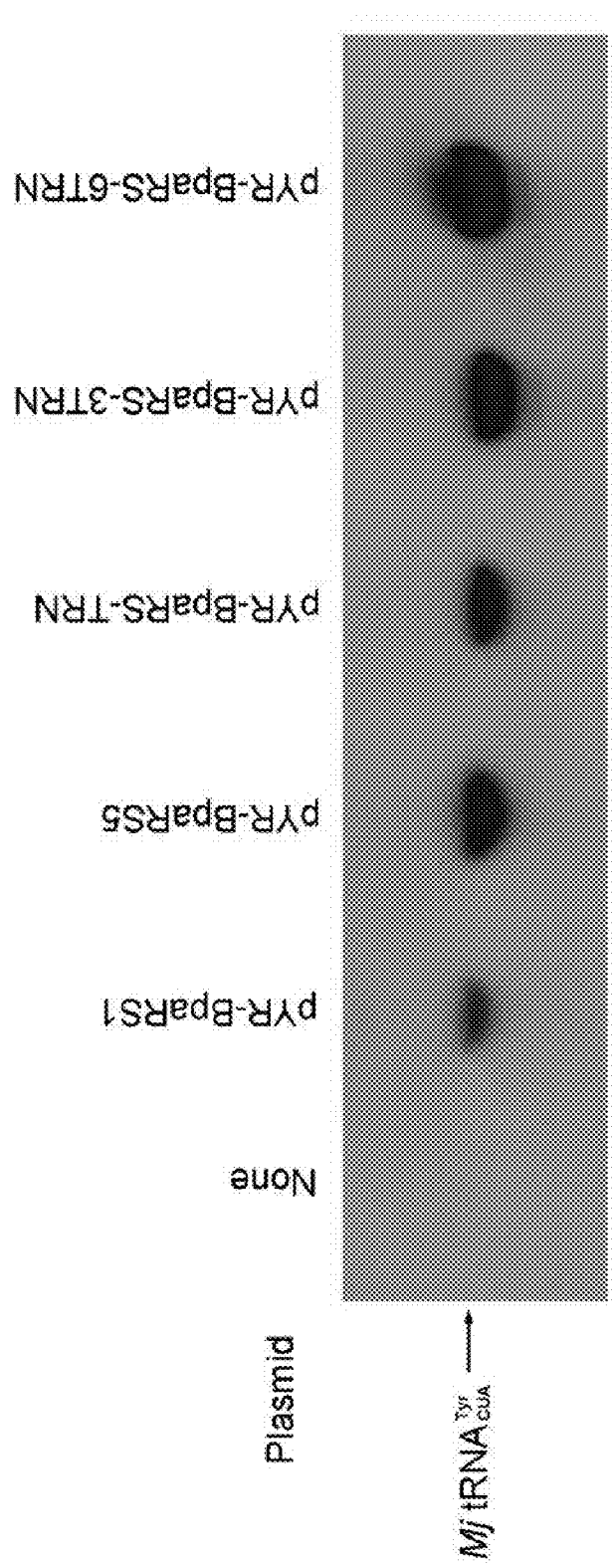
FIG. 3 provides a chemiluminescence image of a northern blot analysis of amber suppressor MjtRNA-Tyr(CUA) expressed from the listed suppression plasmids.

To determine the suppression efficiency of this pYR-BpaRS1 PLASMID system, β-galactosidase activity was measured for TOP10 E. coli cells (Invitrogen™) co-transformed with pYR-BpaRS1 and a lacZ reporter plasmid which encodes β-galactosidase with an amber mutation at a permissive site in the leader sequence of the lacZ gene. Unfortunately, when cells were grown in the presence of 1 mM Bpa, very low levels of β-galactosidase activity were observed (FIG. 2). Attempts to increase suppression efficiency by modifying the flanking sequences of the tRNA gene were unsuccessful.

In order to improve this suppression efficiency, a new amber suppressor tRNA operon with a naturally occurring E. coli tRNA promoter and terminator was constructed. A survey of E. coli tRNA genes revealed that E. coli prolyl tRNAs have the same C1-G72 pair as Archaea tRNAs; this base pair is a major identity determinant for the selective recognition of MjtRNA-Tyr(CUA) by MjTyrRS in E. coli (Wang and Schultz, Chem. Biol. 8:883-890 (2001)). In view of this observation, a synthetic amber suppressor tRNA gene was constructed such that the MjtRNA-Tyr(CUA) gene replaces the same length (77-nucleotide) E. coli proK gene in the monocistronic proK operon. Since the proK gene encodes the tRNA that recognizes the most frequently used proline codon (CCG) in E. coli (Nakamura et al., Nucleic Acids Res. 28:292 (2000)), we expected the MjtRNA-Tyr(CUA) gene to be efficiently transcribed under control of the proK promoter. A FIS binding site naturally located upstream of the proK promoter was also included in the synthetic gene construct to enhance tRNA transcription (Muskhelishvili et al., EMBO J. 16:3655-3665 (1997)). The final expression vector pYR-BpaRS5 was generated by substituting the original suppressor tRNA operon in pYR-BpaRS1 with the MjtRNA-Tyr(CUA) gene under control of the proK promoter and terminator. When transformed into E. coli, this plasmid led to a 2-fold increase (relative to the original tRNA gene under control of the lpp promoter and the rrnC terminator) in the expression of MjtRNA-Tyr(CUA) as observed by northern analysis (see FIG. 3). This increase in expression corresponds to 8% suppression efficiency (relative to wild-type β-galactosidase expression) as determined by β-galactosidase activity assay (FIG. 2).

Example 2

The Generation of Improved Synthetase Genes and Promoters

The present Example describes the construction of improved systems for the expression of orthogonal translation system components, where the effects of mutations in the synthetase gene and the synthetase promoter are determined.

Kobayashi et al. previously reported that a single amino acid substitution of Asp286 to Arg (D286R) in MjTyrRS significantly increased the overall aminoacylation rate (67-fold higher kcat/Km) of MjtRNA-Tyr(CUA) in vitro, mainly due to enhanced recognition (57-fold lower Km) of the anticodon (CUA) in the amber suppressor tRNA by the cognate synthetase (Kobayashi et al., Nat. Struct. Biol. 10:425-432 (2003)). Using this information, this same D286R mutation was introduced into the BpaRS gene in pYR-BpaRS5 by site-directed mutagenesis. Indeed, the D286R mutant of BpaRS led to a 4.5-fold increase in β-galactosidase activity (see FIG. 2).

A mutant glnS promoter (SEQ ID NO: 12), which has a TATC sequence in place of GATC at the −10 region was previously shown to increase gene expression (Plumbridge and Söll, Biochimie 69:539-541 (1987)). Knowing this, the wild type glnS promoter in pYR-BpaRS5 was replaced with the mutated form of the glnS promoter described in Plumbridge and Söll in an attempt to improve efficiency of the system. However, following the insertion of this promoter sequence into pYR-BpaRS5, sequencing revealed that in addition to the intended mutation, additional unintended deletion mutations were also identified. Of the deletion mutants assayed for β-galactosidase activity, one particular mutant, pYR-BpaRS-TRN, which has a single nucleotide deletion (residue A at the −15 position) in addition to the intended one-nucleotide substitution (G to T at the −11 position) in the glnS promoter, exhibited a 5-fold increase in β-galactosidase activity compared to pYR-BpaRS5 (see FIG. 2). The complete nucleotide sequence of this new mutant glnS promoter domain, termed glnS-TRN identified following our sequencing is provided in SEQ IN NO: 13.

| Description | Sequence | SEQ ID NO: |
|---|---|---|
| mutant glnS promoter descirbed in Plumbridge and Söll | CGATTATCAATTTTAAAAAACTAACAGTT GTCAGCCTGTCCCGCTTATAATATCATAC GCC | 12 |
| glnS promoter TRN | CGATTATCAATTTTAAAAAACTAACAGTT GTCAGCCTGTCCCGCTTTAATATCATACG CC | 13 |

Figure 4:
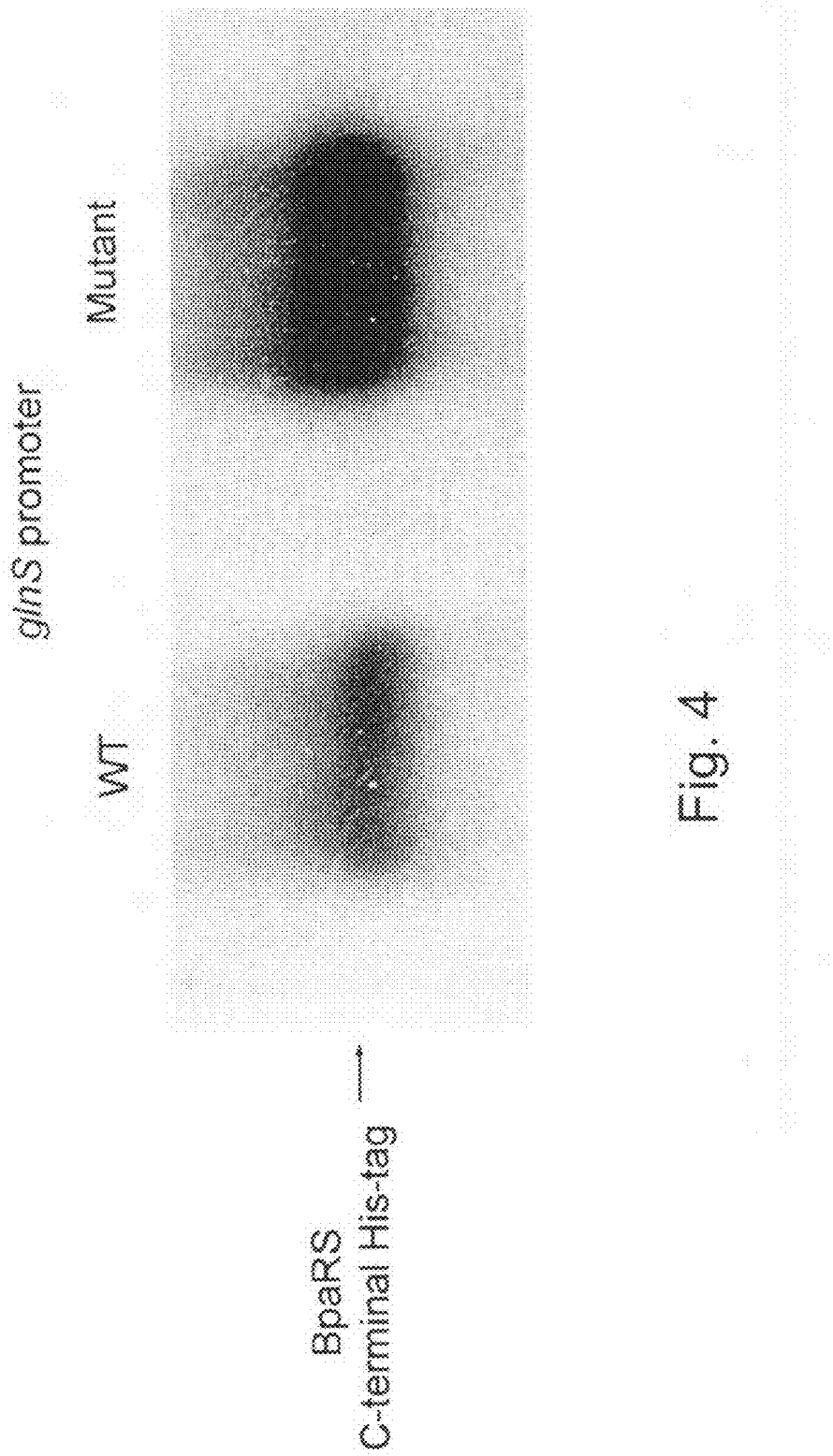
FIG. 4 provides a chemiluminescence image following a western blot analysis of BpaRS expressed under control of the wild-type glnS promoter and the mutated form of the glnS promoter. The blot used an anti-His(C-term) antibody-HRP conjugate (Invitrogen).

BpaRS expression under control of the mutated form of the glnS promoter was improved 2-fold as determined in Western blotting analysis (see FIG. 4). A further 1.5-fold increase in β-galactosidase activity was observed by combination of the D286R substitution of BpaRS and the new mutant glnS promoter, corresponding to an overall suppression efficiency of 57% for pYR-BpaRS-TRN(D286R).

Example 3

The Generation of Improved tRNA Expression Systems

The present Example describes the construction of improved systems for the expression of orthogonal translation system components, where the effects of placing multiple copies of the MjtRNA-Tyr(CUA) in a polycistronic operon are determined.

The effect of multiple copies of the amber suppressor tRNA on suppression efficiency was observed. A polycistronic MjtRNA-Tyr(CUA) operon containing three copies of the amber suppressor tRNA gene under control of a single proK promoter and terminator was constructed.

The three tandem O-tRNA sequences in the polycistronic operon were separated from each other by tRNA linker sequences derived from naturally occurring E. coli tRNA linker sequences. These particular linker sequences were chosen because they contain T(−1) and A(77) nucleotides. These two nucleotide positions in tRNA linkers have been shown to be optimal for efficient 5' and 3'-processing of tRNA precursors when in their native (i.e., endogenous) context.

The first and second MjtRNA-Tyr(CUA) genes in the recombinant polycistronic operon are separated by a tRNA linker derived from the linker that occurs naturally between the E. coli valU and valX tRNA genes (SEQ ID NO: 14). The second and third MjtRNA-Tyr(CUA) genes in the recombinant polycistronic operon are separated by a tRNA linker derived from the linker that occurs naturally between the E. coli ileT and alaT tRNA genes (SEQ ID NO: 15). Use of these linkers has a further practical advantage in that these polynucleotides contain convenient restriction sites.

Two identical copies of the synthetic polycistronic tRNA operon containing three copies of the suppressor tRNA gene were ligated to generate gene clusters with six copies of the MjtRNA-Tyr(CUA) gene. The assembled gene clusters with three and six copies of the tRNAs were cloned into pYR-BpaRS-TRN(D286R) to generate pYR-BpaRS-3TRN (D286R) and pYR-BpaRS-6TRN(D286R), respectively. When expressed in E. coli, these plasmids provided a 30% and 50% increase in MjtRNA-Tyr(CUA) expression, respectively, as determined by northern analysis (see FIG. 3). This increase in message expression afforded a 30-40% increase in β-galactosidase activity (see FIG. 2).

Figure 5:
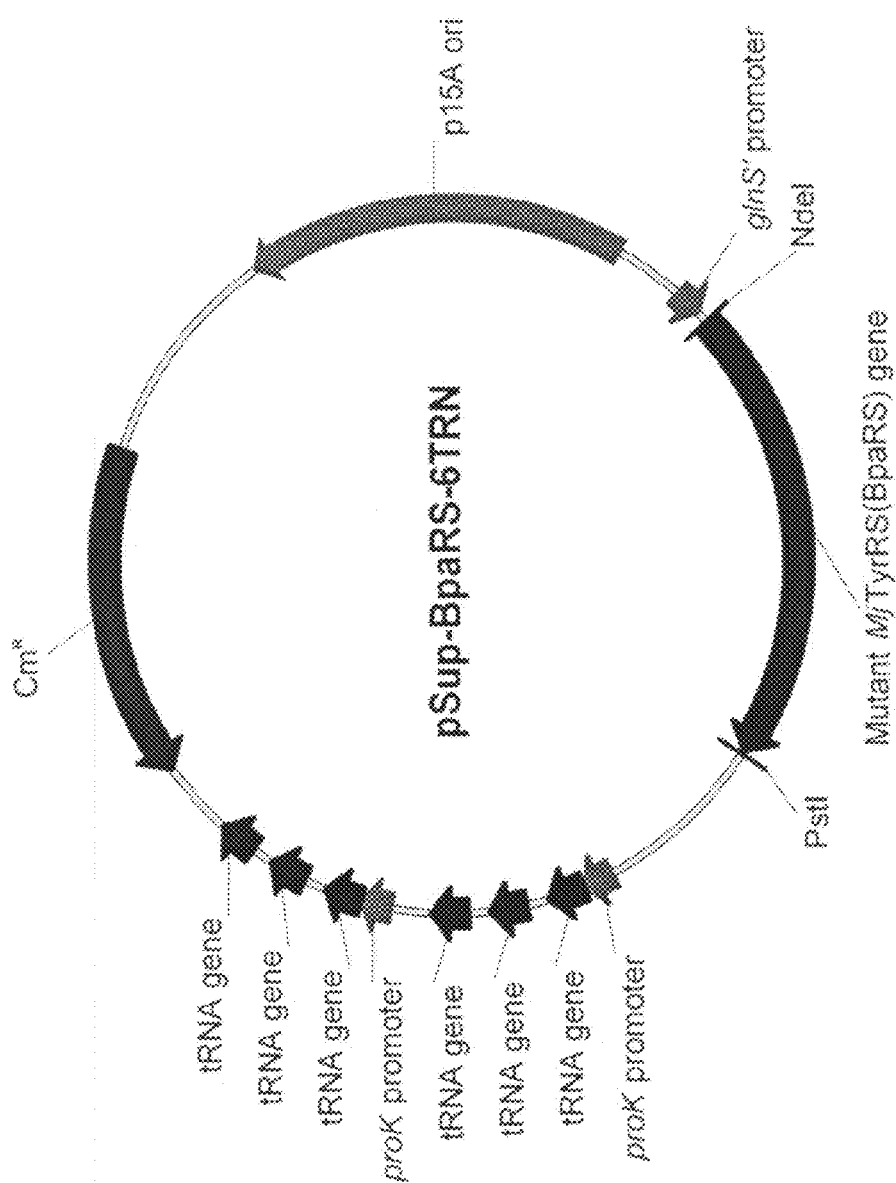
FIG. 5 shows a plasmid map of pSup-BpaRS-6TRN. Other synthetase genes were sub-cloned from their corresponding pBK plasmids into the NdeI/PstI sites of this plasmid.

Because the E. coli rare codon tRNAs encoded in these plasmids may be unnecessary for expression of most proteins, these E. coli tRNA genes were removed from the plasmid pYR-BpaRS-6TRN(D286R) to afford pSup-BpaRS-6TRN (D268R) (shown in FIG. 5). As expected, the suppression efficiency of this plasmid determined by in vivo β-galactosidase activity assay remained the same as that of its parent plasmid (see FIG. 6).

Example 4

Expression of a Model Protein Comprising an Unnatural Amino Acid Using Improved Expression Systems The present Example describes the expression of a model protein sperm whale myoglobin comprising an unnatural amino acid using the improved expression systems of the invention.

Figure 6:
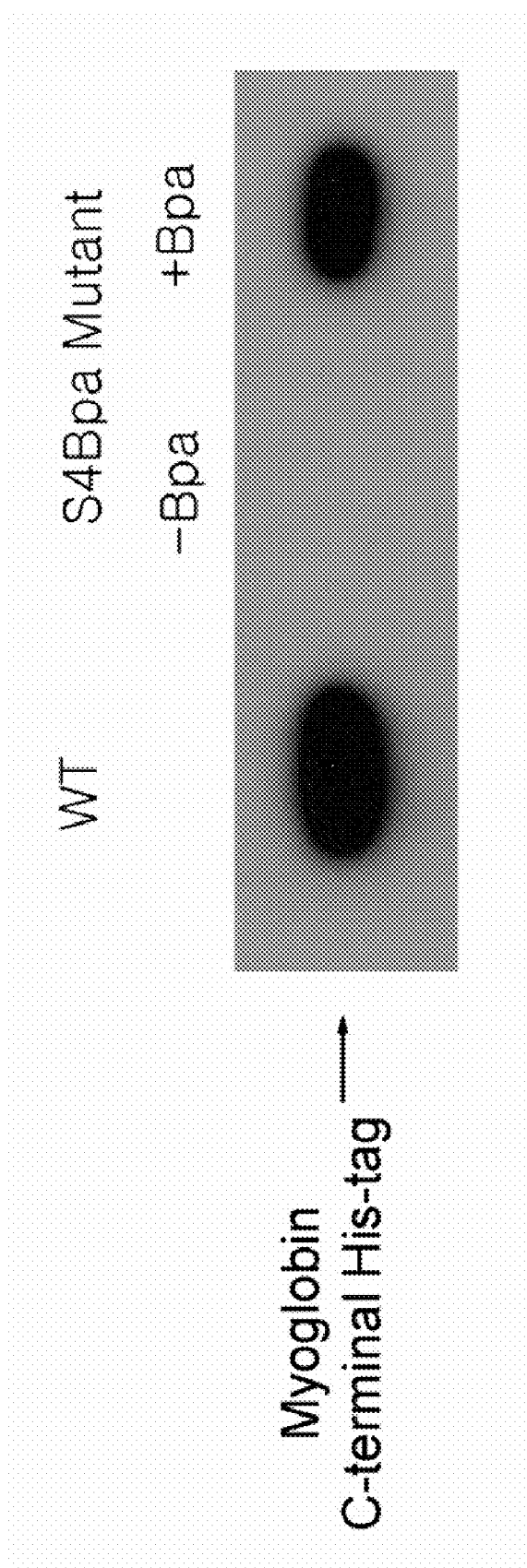
FIG. 6 shows the suppression efficiencies of the new system for Bpa, pAcPhe, pAzPhe and pIPhe incorporation. Error bars indicate standard deviation and n=3.

To further examine improvements in yield and fidelity of unnatural amino acid incorporation into proteins using the systems of the invention, a Ser-4 to Bpa mutant of sperm whale myoglobin (described in Chin et al., Proc. Natl. Acad. Sci. USA 99:11020-11024 (2002)) was expressed in E. coli. TOP10 E. coli cells (Invitrogen™) co-transformed with pBAD/Myc-His/MB(S4TAG) and pSup-BpaRS-6TRN (D286R) were grown in Luria-Bertani media at 37° C. in the presence of 1 mM Bpa. Consistent with the above in vivo β-galactosidase assay data, the full length mutant myoglobin was produced in an overall purified yield of 40 mg/L, whereas the previous system provided 2 mg/L of mutant protein (Chin et al., Proc. Natl. Acad. Sci. USA 99:11020-11024 (2002)). No mutant protein was observed by SDS-PAGE gel in the absence of the amino acid (FIG. 6). MALDI-TOF mass spectrometry of the mutant myoglobin containing Bpa in place of Ser-4 gave an average mass of 18521, which is in good agreement with the calculated predicted mass of 18520. No evidence of any natural amino acid incorporation at position 4 was detected in the mass spectrum.

Example 5

Broad Applicability of the Improved Expression Systems of the Invention

The present Example describes the expression of β-galactosidase comprising four different unnatural amino acids where the expressions systems use different mutant synthetases that have charging specificities for different unnatural amino acids.

Figure 7:
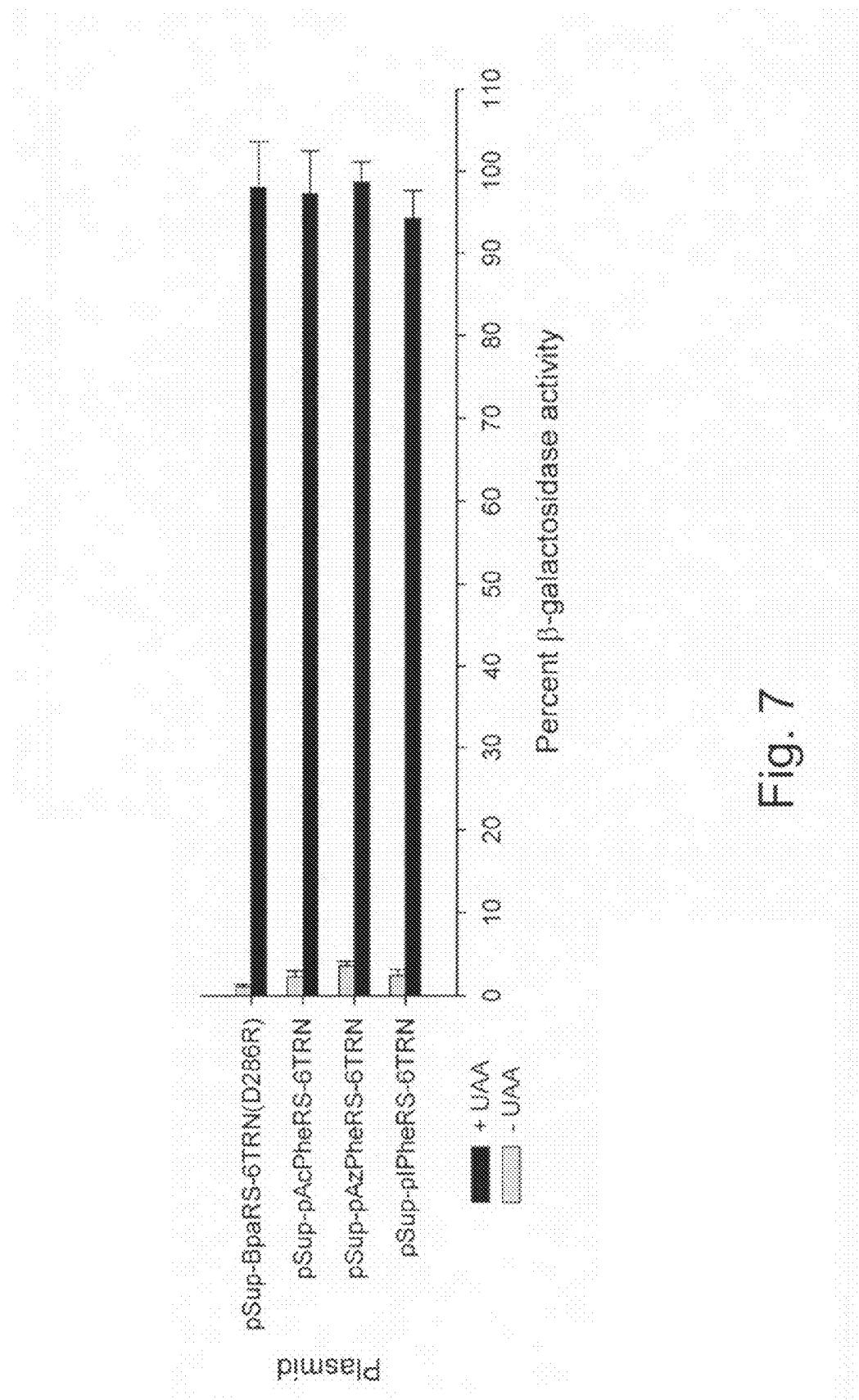
FIG. 7 provides a chemiluminescence image following western blotting of a mutant myoglobin containing Bpa in place of Ser-4 expressed in the absence or presence of Bpa. The blot used an anti-His(C-term) antibody-HRP conjugate (Invitrogen).

To test the generality of this expression systems of the invention, three additional orthogonal aminoacyl-tRNA synthetases were tested in the system. These O-RSs specifically aminoacylate (i.e., charge) the O-tRNA MjtRNA-Tyr(CUA) with, alternatively, p-acetyl-L-phenylalanine (pAcPhe), p-azido-L-phenylalanine (pAzPhe) and p-iodo-L-phenylalanine (pIPhe) (FIG. 1). These unnatural amino acids are useful for chemical-labeling (Wang et al., Proc. Natl. Sci. Acad. USA 100:56-61 (2003)), photo-crosslinking (Chin et al., J. Am. Chem. Soc., 124:9026-9027 (2002)), and X-ray crystallographic phasing (Xie et al., Nat. Biotechnol., 22:1297-1301 (2004)) experiments. Expression vectors of the invention encoding these mutant MjTyrRS genes were constructed by sub-cloning the respective O-RS into the NdeI/PstI sites of pSup-BpaRS-6TRN(D286R), to yield the vectors pSuppAcPheRS-6TRN, pSup-pAzPheRS-6TRN and pSup-pIPheRS-6TRN. As was the case with Bpa, when *E. coli* cells harboring these plasmids are grown in the presence of these amino acids (1 mM), the β-galactosidase activity level is similar to that from wild type β-galactosidase (FIG. 7), indicating production of the β-galactosidase comprising the respective unnatural amino acid.

Example 6

Plasmid Constructions pYR-BpaRS1 pYR-BpaRS1, a p15A replicon which contains a chloramphenicol resistance marker, MjtRNA-Tyr(CUA) under control of the lpp promoter and rrnC terminator, and BpaRS under control of the glnS promoter, was generated by inserting the BpaRS and MjtRNA-Tyr(CUA) genes into the SacI and SpeI sites of the pRARE2 plasmid (Novagen).

MjtRNA-Tyr(CUA) Gene with the proK Promoter and Terminator

A monocistronic MjtRNA-Tyr(CUA) operon containing the proK promoter and terminator was constructed by PCR using four synthetic oligonucleotides in an overlapping PCR strategy to construct the entire tRNA operon in a single PCR reaction:

| Primer | Sequence | SEQ ID NO: |
|---|---|---|
| proK P1 | GTGCACGGCTAACTAAGCGGCCTGCTGACTTTCTCGCCGATCAAAAGGC | 37 |
| proK T1 | CTTTCTCGCCGATCAAAAGGCATTTTGCTATTAAGGGATTGACGAGGGCGTATCTGCGCAGTAAGATGCGCCCCGCATTCCGGCGGTAGTTCAGCAGGGC | 38 |
| proK T2 | CTTTCTCGCCGATCAAAAGGCATTTTGCTATTAAGGGATTGACGAGGGCGTATCTGCGCAGTAAGATGCGCCCCGCATTCCGGCGGTAGTTCAGCAGGGC | 39 |
| proK P2 | GCATAAGCTTATGCAAAAAAGCCTGCTCGTTGAGCAGGCTTTTCG | 40 |

The PCR amplicon was subsequently amplified by PCR using two primers:

| Primer | Sequence | SEQ ID NO: |
|---|---|---|
| proK-F | AGTC<u>TGATCA</u>GTGCACGGCTAACTAAGCGG | 41 |
| proK-R | GCAT<u>CTCGAG</u>ATGCAAAAAAGCCTGCTCGTTG | 42 |

The resulting amplicon was inserted between the BclI and XhoI sites (underlined) of pYR-BpaRS1 to generate the plasmid pYR-BpaRS5.

Mutant glnS Promoter

A mutant glnS promoter was constructed by PCR using four synthetic oligonucleotides:

| Primer | Sequence | SEQ ID NO: |
|---|---|---|
| glnS P1 | CCGAGCTCCCGGGTCATC | 43 |
| glnS T1 | CCGAGCTCCCGGGTCATCAATCATCCCCATAATCCTTGTTAGATTATCAATTTTAAAAAACTAACAGTTGTCAGCCTGTC | 44 |
| glnS T2 | GTCCATATGGGATTCCTCAAAGCGTAAACAACGTATAACGGCGTATGATATTATAAGCGGGACAGGCTGACAACTGTTAG | 45 |
| glnS P2 | GTCCATATGGGATTCCTC | 46 |

The product was inserted between the XmaI and NdeI sites of pYR-BpaRS5. A number of clones were screened with an in vivo LacZ activity assay and one particular single-base deletion mutant with improved activity was identified and sequenced (termed pYR-BpaRS-TRN).

Tandem tRNA Gene Cassettes

Two tRNA linker sequences that naturally occur between the valU and valX genes (SEQ ID NO: 14) and between the ileT and alaT genes (SEQ ID NO: 15) in the *E. coli* genome were used as spacers between the MjtRNA-Tyr(CUA) genes. These linker sequences contain BsmAI and EarI restriction sites to which the MjtRNA-Tyr(CUA) genes were ligated. These flanking sequences also contain T(−1) and A(77) residues, which are optimal for efficient 5' and 3'-processing of the tRNA precursors. The tRNA gene cassette was amplified by PCR using three sets of primers:

| Primer | Sequence | SEQ ID NO: |
|---|---|---|
| Set 1 | | |
| Linker P1 | GTGCACGGCTAACTAAGCGGCCTGCTGACTTTCTCGCCGATCAAAAGGC | 47 |
| Linker P2 | TACACGGCGGAGACTACATAAAGTAGTTGGTCCGGCGGGCCGGATTTG | 48 |
| Set 2 | | |
| Linker P3 | GTAGTCTCCGCCGTGTAGCAAGAAATTGAGAAGTCCGGCGGTAGTTCAGCAG | 49 |
| Linker P4 | AAACCTCTTCAAATTTGCCGTGCAAATTTGGTCCGGCGGGCCGGATTTG | 50 |
| Set 3 | | |
| Linker P5 | GCAAATTTGAAGAGGTTTTAACTACATGTTATCCGGCGGTAGTTCAGCAG | 51 |
| proK-R | GCATCTCGAGATGCAAAAAAGCCTGCTCGTTG | 52 |

The product from each set was digested with BsmAI (Set 1), EarI (Set 2) or both (Set 3). Ligation of these three restriction fragments produced a polycistronic tRNA operon containing three copies of the tRNA gene connected by two different naturally occurring linker sequences. The resulting gene cluster was amplified by PCR using two sets of primers:

| Primer | Sequence | SEQ ID NO: |
|---|---|---|
| Set 4 | | |
| Tandem P1 | ATCAGTGCACGGCTAACTAAGCGG | 53 |
| Tandem P2 | GCTGGCATGCATGCAAAAAAGCCTGCTCGTTGAGC | 54 |
| Set 5 | | |
| Tandem P3 | ATCAGCATGCGGCTAACTAAGCGGCCTGCTG | 55 |
| Tandem P4 | GCTGCTCGAGATGCAAAAAAGCCTGC | 56 |

PCR products from Sets 4 and 5 were digested with SphI and ligated with each other to generate a unidirectional tandem tRNA gene assembly, which consists of two identical polycistronic tRNA operons, each encoding three tRNA genes under control of a single proK promoter and terminator. Each tRNA gene cluster containing one or two identical copies of the polycistronic tRNA operon was cloned into the ApaLI and XhoI sites of pYR-BpaRS-TRN to afford pYR-BpaRS-3TRN and pYR-BpaRS-6TRN, respectively.

pSup Plasmids

Each of the twelve E. coli tRNA genes, which were originally encoded in pRARE2 plasmid, were removed from pYR-BpaRS-6TRN(D286R) by digestion with SpeI and DrdI followed by treatment with Mung bean nuclease. Religation of the linearized vectors generated pSup-BpaRS-6TRN (D286R). Mutant MjTyrRS genes for p-acetyl-L-phenylalanine, p-azido-L-phenylalanine and p-iodo-L-phenylalanine were sub-cloned from their corresponding pBK plasmids into the NdeI and PstI sites of pSup-BpaRS-6TRN(D286R) to generate pSup-pAcPheRS-6TRN, pSup-pAzPheRS-6TRN and pSup-pIodoPheRS-6TRN, respectively.

lacZ Reporter Plasmid and In Vivo β-Galactosidase Activity Assay

The phenylalanine codon (TTC) at residue 13 (underlined) of the leader sequence (MDPLVTAASVLEFGLFET; SEQ ID NO: 57) located upstream of the lacZ gene of pBAD/Myc-His/LacZ (Invitrogen™) was mutated to an amber codon (TAG) by site-directed mutagenesis to produce a LacZ reporter plasmid pBAD/Myc-His/LacZ(TAG). This plasmid was co-transformed with each suppressor plasmid into E. coli TOP10 cells (Invitrogen™). Cells were incubated at 37° C. overnight in Luria-Bertani (LB) medium containing 0.02% arabinose and 1 mM unnatural amino acid. LacZ (β-galactosidase) activity was measured according to the method described by Miller (Miller, J. H. Experiments in Molecular Genetics. (Cold Spring Harbor Laboratory, New York, 1972)).

Example 7

General Methodologies

XL1-Blue E. coli cells (Stratagene) were used for cloning and maintaining plasmids. PfuUltra™ High-Fidelity DNA polymerase (Stratagene®) was used for polymerase chain reaction (PCR). QuikChange® II site-directed mutagenesis kit (Stratagene®) was used for site-directed mutagenesis. Sequences of all plasmids constructed were verified by sequencing.

Protein Expression

A C-terminal hexahistidine tagged mutant sperm whale myoglobin gene with an amber codon at position four (Ser-4) was inserted from pBAD-JYAMB-4TAG between the NcoI and KpnI sites of pBAD/Myc-His (Invitrogen™) to generate pBAD/Myc-His/MB(S4TAG). The plasmid was co-transformed with pSup-BpaRS-6TRN(D286R) into E. coli TOP10 (Invitrogen™). Cells were incubated at 37° C. in LB containing 100 mg/ml carbenicillin, 50 mg/ml chloramphenicol and 1 mM Bpa. At OD600=0.6, cells were induced by the addition of 0.2% arabinose and incubated for 12 h. Cells were harvested by centrifugation and lysed with BugBuster® reagent (Novagen®). Protein obtained from inclusion bodies was purified with TALON® metal affinity resin (Clontech®) under denaturing conditions according to the manufacturer's protocol. Purified protein was concentrated by ultrafiltration and analyzed by MALDI-TOF mass spectrometry. Protein concentration was measured by the Bradford method.

Northern Analysis

E. coli TOP10 cells (Invitrogen™) transformed with each suppression plasmid were incubated in LB at 37° C. At OD600=0.8, cells were harvested. Total tRNA was isolated by phenol extraction and isopropanol fractionation as previously described (Deutscher and Hilderman, "Isolation and partial characterization of Escherichia coli mutants with low levels of transfer ribonucleic acid nucleotidyltransferase," J. Bacteriol., 118:621-627 (1974)). The RNA samples were separated on a 15% denaturing polyacrylamide gel and transferred to GeneScreen Plus® membrane (PerkinElmer®). The membrane was hybridized overnight at 55° C. with:

(SEQ ID NO: 58)
5'-biotin-CCCTGCTGAACTACCGCC-3'.

The hybridized biotinylated probe was detected using the North2South chemiluminescence hybridization and detection kit (Pierce) according to the manufacturer's protocol.

Western Analysis of Bpa Expression

A C-terminal hexahistidine tagged BpaRS gene was constructed by PCR and inserted between the NdeI and PstI sites of pYR-BpaRS5 and pYR-BpaRS-TRN to generate pYR-BpaRS5(C-His) and pYR-BpaRS-TRN(C-His), respectively. E. coli Top 10 cells transformed with each plasmid were incubated in LB at 37° C. Cells were harvested at OD600=1 and lysed with Bugbuster reagent. Total protein was separated on 10% polyacrylamide gel and transferred to PVDF membrane (Invitrogen). The membrane was hybridized with Anti-His(C-term) antibody-HRP conjugate (Invitrogen) and detected by chemiluminescence.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A composition comprising a nucleic acid construct, said construct comprising:
   (a) promoter and terminator nucleotide sequences from an *Escherichia coli* proline tRNA gene and a heterologous expressible nucleotide sequence, wherein said promoter and terminator sequences are both operatively linked to said heterologous expressible nucleotide sequence, and wherein said heterologous expressible nucleotide sequence encodes an Archaea tRNA; or
   (b) a promoter nucleotide sequence corresponding to a modified *E. coli* glnS promoter having a nucleotide sequence of SEQ ID NO: 13 and an expressible nucleotide sequence, wherein said modified *E. coli* glnS promoter nucleotide sequence is operatively linked to said expressible nucleotide sequence.

2. The composition of claim 1, wherein said construct comprises both (a) and (b), wherein said expressible nucleotide sequences in (a) and (b) are different.

3. The composition of claim 1, wherein said construct comprises (a) and (b), wherein said expressible nucleotide sequence in (a) encodes an orthogonal tRNA (O-tRNA), wherein said expressible nucleotide sequence in (b) encodes an orthogonal aminoacyl tRNA synthetase (O-RS), and wherein said O-RS preferentially aminoacylates said O-tRNA with an unnatural amino acid.

4. The composition of claim 1, wherein said *E. coli* proline tRNA gene is selected from *E. coli* proK, proL and proM tRNA genes.

5. The composition of claim 1, wherein said *E. coli* proline tRNA promoter and terminator sequences are the promoter and terminator sequences of *E. coli* proK provided in SEQ ID NO: 32 (promoter) and SEQ ID NO: 33 (terminator), respectively.

6. The composition of claim 1, wherein said expressible nucleotide sequence in (a) is a polycistronic operon comprising a plurality of one or more nucleotide sequences.

7. The composition of claim 1, wherein said Archaea tRNA is encoded by a nucleotide sequence of SEQ ID NO: 1 (MjtRNA-Tyr(CUA)).

8. The composition of claim 1, wherein said expressible nucleotide sequence is a polycistronic operon comprising a plurality of the nucleotide sequence of SEQ ID NO: 1 (MjtRNA-Tyr(CUA)).

9. The composition of claim 8, wherein said expressible nucleotide sequence is a plurality of said polycistronic operon.

10. The composition of claim 1, wherein said expressible nucleotide sequence of (b) encodes a polypeptide.

11. The composition of claim 1, wherein said expressible nucleotide sequence of (b) encodes an aminoacyl-tRNA synthetase.

12. The composition of claim 1, wherein said expressible nucleotide sequence of (b) encodes an orthogonal aminoacyl-tRNA synthetase (O-RS) derived from a *Methanococcus jannaschii* tyrosyl-tRNA synthetase, and wherein said O-RS has an aspartic acid to arginine substitution at amino acid position 286 or at a position analogous to position 286, relative to the amino acid sequence of wild-type *Methanococcus jannaschii* tyrosyl-tRNA synthetase provided in SEQ ID NO: 2.

13. A host cell comprising the composition of claim 1.

14. The host cell of claim 13, wherein said host cell is a eubacterial host cell.

15. The host cell of claim 13, wherein said host cell is an *E. coli* cell.

16. The composition of claim 8, wherein said polycistronic operon comprises a plurality of heterologous polynucleotide linkers.

17. The composition of claim 8, wherein said polycistronic operon comprises a plurality of heterologous polynucleotide linkers, wherein at least two of the heterologous polynucleotide linkers are different.

18. The composition of claim 16, wherein said heterologous polynucleotide linkers comprise a 5' terminal thymidine nucleotide, a 3' terminal adenosine nucleotide, or both a 5' terminal thymidine nucleotide and a 3' terminal adenosine nucleotide.

19. The composition of claim 16, wherein said heterologous polynucleotide linkers are from the naturally occurring polynucleotide linkers located between the endogenous *Escherichia coli* tRNA genes selected from: valU and valX; ileT and alaT; serV and argV; valV and valW; glyT and thrT; metT and leuW; glnW and metU; hisR and leuT; glnU and glnW; leuP and leuV; glnV and glnX; alaW and alaX; ileU and alaU; ileV and alaV; metU and glnV; glyW and cysT; argX and hisR; and argY and argZ.

20. The composition of claim 16, wherein said heterologous polynucleotide linkers are from the nucleotide sequence of SEQ ID NO: 14 (valU/valX linker) or 15 (ileT/alaT linker).

* * * * *